US011426128B1

(12) United States Patent
Ruby et al.

(10) Patent No.: US 11,426,128 B1
(45) Date of Patent: Aug. 30, 2022

(54) PATIENT EXAMINATION SYSTEM

(71) Applicant: Krug Inc., Kitchener (CA)

(72) Inventors: Leonard Ruby, Kitchener (CA); Paul Crossland, Kitchener (CA); Cesar Fernandes, Kitchener (CA); Kyunghun Park, Kitchener (CA)

(73) Assignee: Krug Inc., Kitchener (CA)

( * ) Notice: Subject to any disclaimer, the term of this patent is extended or adjusted under 35 U.S.C. 154(b) by 0 days.

(21) Appl. No.: 17/136,327

(22) Filed: Dec. 29, 2020

Related U.S. Application Data

(63) Continuation-in-part of application No. 16/287,264, filed on Feb. 27, 2019, now Pat. No. 10,874,574.

(60) Provisional application No. 62/635,599, filed on Feb. 27, 2018.

(51) Int. Cl.
*A61G 5/12* (2006.01)
*A61B 5/00* (2006.01)
*A61G 5/00* (2006.01)
*A61G 5/10* (2006.01)
*A61G 7/018* (2006.01)

(52) U.S. Cl.
CPC .............. *A61B 5/704* (2013.01); *A61G 5/006* (2013.01); *A61G 5/1091* (2016.11); *A61G 5/128* (2016.11); *A61G 7/018* (2013.01)

(58) Field of Classification Search
CPC ...... A61G 5/125; A61G 15/12; A61G 5/1253; A61G 5/128; A47C 20/023; A47C 20/128; A47C 7/5068; A47C 1/0308; A47C 7/543
See application file for complete search history.

(56) References Cited

U.S. PATENT DOCUMENTS

| 583,136 A | 5/1897 | Anderson |
| 3,083,996 A | 4/1963 | Caldemeyer et al. |
| 3,845,945 A | 11/1974 | Lawley et al. |
| 4,494,259 A | 1/1985 | Miller et al. |
| 4,612,679 A | 9/1986 | Mitchell |
| 4,660,883 A | 4/1987 | Kowalski |
| 4,941,709 A | 7/1990 | Moller |
| D379,409 S | 5/1997 | Schwaegerle et al. |
| 5,836,645 A * | 11/1998 | Sakaue ................ A47C 1/0342 297/68 |
| 5,862,549 A | 1/1999 | Morton et al. |

(Continued)

FOREIGN PATENT DOCUMENTS

| DE | 102005002182 A1 * | 7/2006 | ........... A47C 7/5068 |
| WO | WO-2017155069 A1 * | 9/2017 | ............... B60N 2/80 |

*Primary Examiner* — Timothy J Brindley

(57) ABSTRACT

A patient examination system including a frame assembly, one or more motion-controlling assemblies connected to the frame assembly for moving one or more selected movable portions of the frame assembly, and a patient support assembly. The patient support assembly includes a seat subassembly including a seat cushion, a back subassembly, a footrest subassembly including a footrest cushion, and a cover element covering a top side of the seat cushion and an external side of the footrest cushion. The cover element has an exposed surface for engagement with the patient. The seat subassembly includes the seat cushion and is secured to the upper element of the frame assembly. The frame assembly is configured to support the seat subassembly relative to the floor in a lowered position thereof, in a raised position thereof, in intermediate seat positions therebetween, and in Trendelenburg positions.

2 Claims, 59 Drawing Sheets

(56) References Cited

U.S. PATENT DOCUMENTS

| | | | |
|---|---|---|---|
| 6,039,402 A | 3/2000 | Nemoto | |
| 6,089,593 A | 7/2000 | Hanson et al. | |
| 6,135,559 A | 10/2000 | Kowalski | |
| 6,336,235 B1 | 1/2002 | Ruehl | |
| 6,460,930 B2 | 10/2002 | Thornton | |
| 6,572,185 B1 * | 6/2003 | Tseng | A47C 1/0355 |
| | | | 297/69 |
| 6,637,812 B2 | 10/2003 | Laughlin et al. | |
| 6,886,196 B2 | 5/2005 | Nygren et al. | |
| 6,928,673 B2 | 8/2005 | Risk, Jr. | |
| 7,024,711 B1 | 4/2006 | Stasney et al. | |
| 7,475,944 B2 | 1/2009 | Griepentrog et al. | |
| 7,644,991 B2 | 1/2010 | Davis et al. | |
| 7,708,347 B2 | 5/2010 | Griepentrog et al. | |
| 9,150,129 B2 * | 10/2015 | Suhre | B60N 3/002 |
| 9,848,704 B1 | 12/2017 | Pollard et al. | |
| 10,874,574 B1 | 12/2020 | Ruby et al. | |
| 10,939,770 B2 * | 3/2021 | Lopez | A47C 7/5068 |
| 2010/0102612 A1 * | 4/2010 | Walters | A47C 7/5068 |
| | | | 297/354.1 |
| 2013/0002001 A1 * | 1/2013 | Allen | B60N 2/77 |
| | | | 297/411.3 |
| 2013/0307308 A1 | 11/2013 | Hankins et al. | |
| 2015/0082537 A1 * | 3/2015 | Ohta | A61G 5/125 |
| | | | 5/2.1 |
| 2015/0342805 A1 | 12/2015 | Harris, Jr. | |
| 2016/0135602 A1 | 5/2016 | Smith | |
| 2017/0252242 A1 * | 9/2017 | Young | A61G 5/1059 |
| 2017/0318971 A1 * | 11/2017 | Kim | A47C 7/5068 |
| 2018/0279797 A1 * | 10/2018 | Havell | A47C 1/0242 |
| 2019/0104855 A1 * | 4/2019 | Iles | A47C 7/5066 |
| 2020/0216179 A1 * | 7/2020 | Last | B64D 11/0647 |
| 2020/0229998 A1 * | 7/2020 | Paz | A61G 5/1067 |

\* cited by examiner

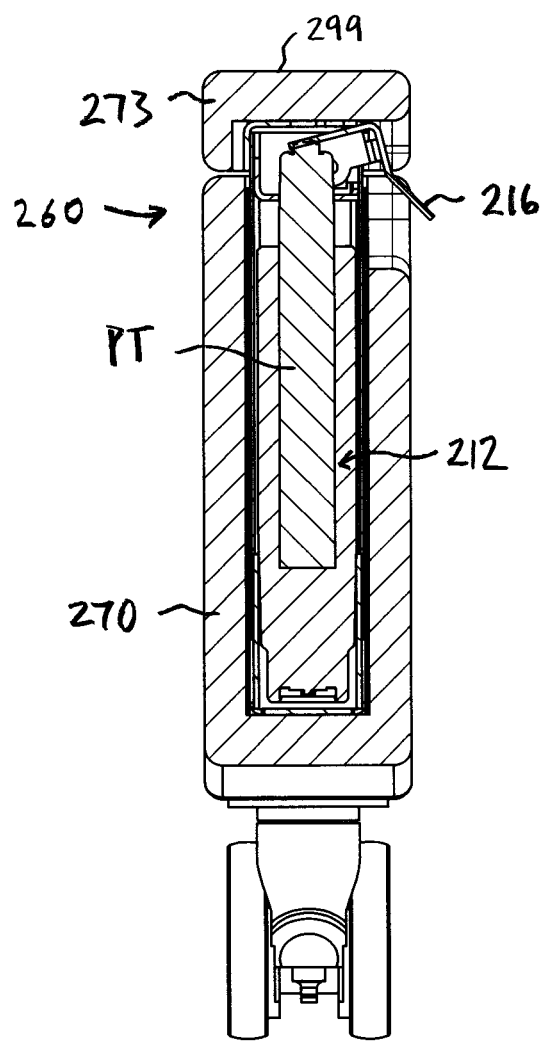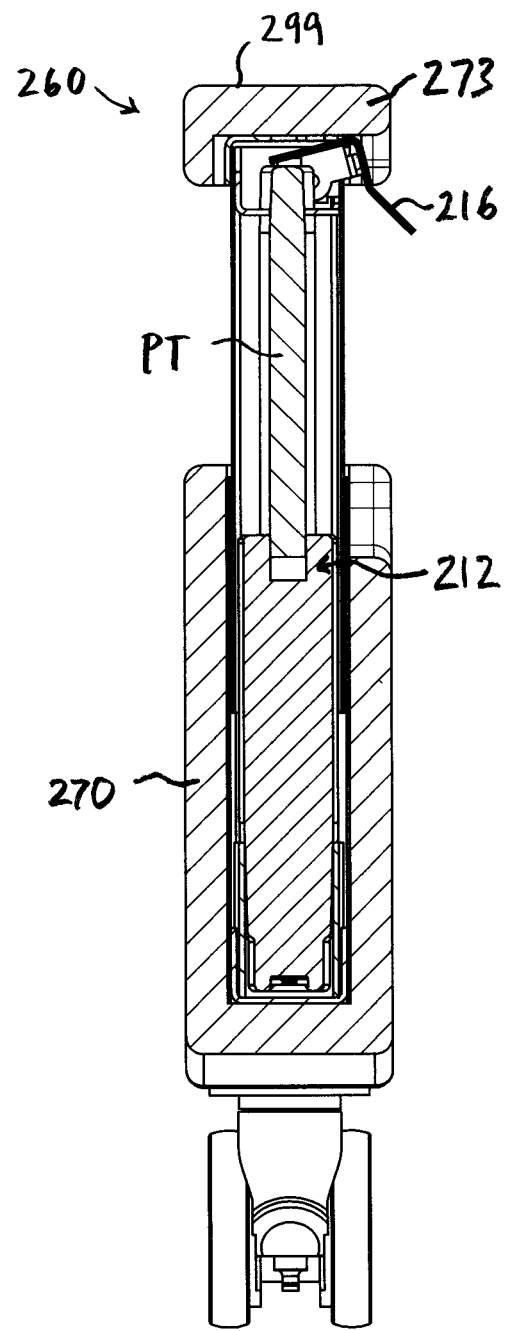
FIG. 24B  FIG. 24C

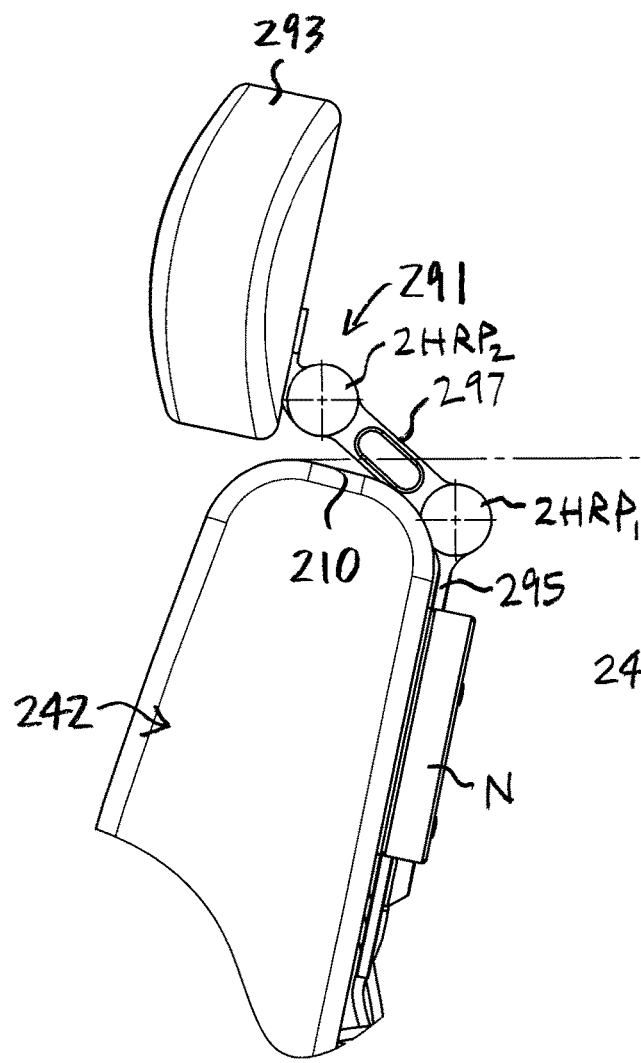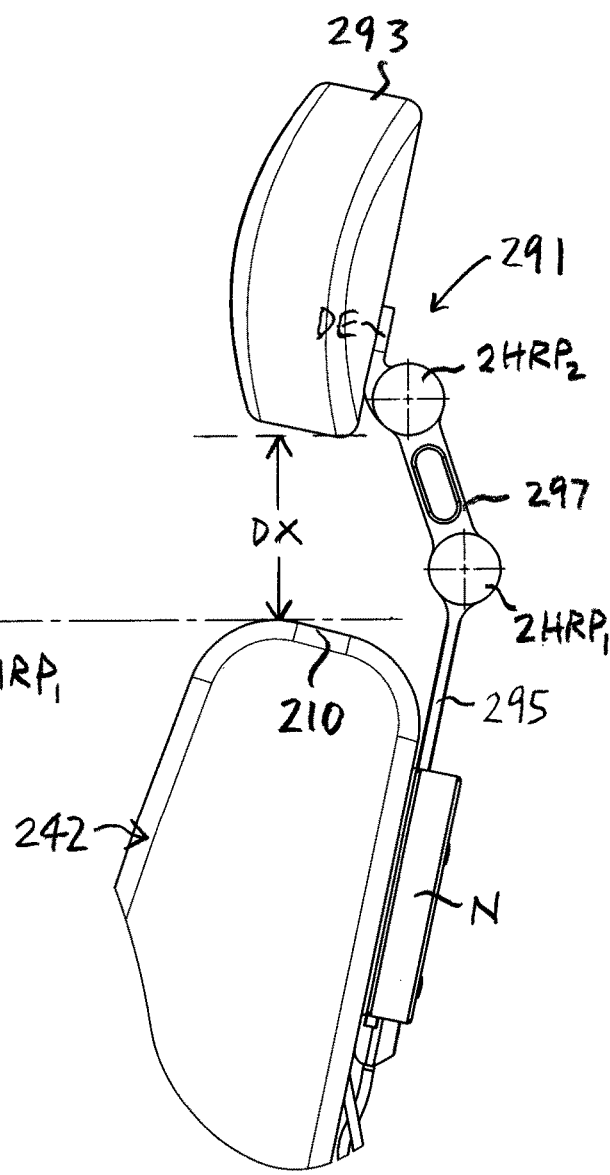
FIG. 27A  FIG. 27B

PATIENT EXAMINATION SYSTEM

CROSS-REFERENCE TO RELATED APPLICATIONS

This application is a continuation-in-part of U.S. patent application Ser. No. 16/287,264, filed on Feb. 27, 2019, and claims the benefit of U.S. Provisional Patent Application No. 62/635,599, filed on Feb. 27, 2018, the entirety of each of which is hereby incorporated by reference.

FIELD OF THE INVENTION

The present invention is a patient examination system.

BACKGROUND OF THE INVENTION

As is well known in the art, two separate items of clinical furniture are needed in order to accommodate the variety of positions which may be requested of a patient. In the prior art, an examination table is used to support the patient in prone, supine, or side-lying positions. An examination chair typically is used to support the patient in a seated or semi-supine position. The need to have two separate items of furniture has a number of disadvantages, e.g., a room in which the patient is examined is usually required to be sufficiently large to accommodate the two furniture items, as well as other equipment.

Legislation in various jurisdictions has imposed a number of requirements on furniture and equipment used in connection with medical care. For example, in the United States, the Americans with Disabilities Act ("ADA") imposes a number of requirements, and in the prior art, compliance with certain of the requirements in regard to clinical furniture has been found to be challenging.

SUMMARY OF THE INVENTION

For the foregoing reasons, there is a need for a patient examination system that overcomes or mitigates one or more of the defects or disadvantages of the prior art. Such defects or disadvantages are not necessarily included in those described above.

In its broad aspect, the invention provides a patient examination system including a frame assembly, one or more motion-controlling assemblies connected to the frame assembly for moving one or more selected movable portions of the frame assembly, and a patient support assembly. The patient support assembly includes a seat subassembly including a seat cushion, a back subassembly, a footrest subassembly including a footrest cushion, and a cover element covering a top side of the seat cushion and an external side of the footrest cushion. The cover element has an exposed surface for engagement with the patient. The seat subassembly includes the seat cushion and is secured to the upper element of the frame assembly. The frame assembly is configured to support the seat subassembly relative to the floor in a lowered position thereof, in a raised position thereof, in intermediate seat positions therebetween, and in Trendelenburg positions.

BRIEF DESCRIPTION OF THE DRAWINGS

The invention will be better understood with reference to the attached drawings, in which:

FIG. 24B is a cross-section of the armrest assembly of FIG. 23A, in which the armrest element is in the engaged position thereof and the activation lever is in the activating position thereof, drawn at a smaller scale;

FIG. 24C is a cross-section of the armrest assembly of FIG. 23C in which the activation lever is in an activating position thereof;

FIG. 27A is a side view of an embodiment of a headrest assembly of the invention including a head rest thereof in a first position thereof; and FIG. 27B is a side view of the headrest assembly of FIG. 27A in which the head rest is in a second position thereof.

DETAILED DESCRIPTION

Figure 1A:
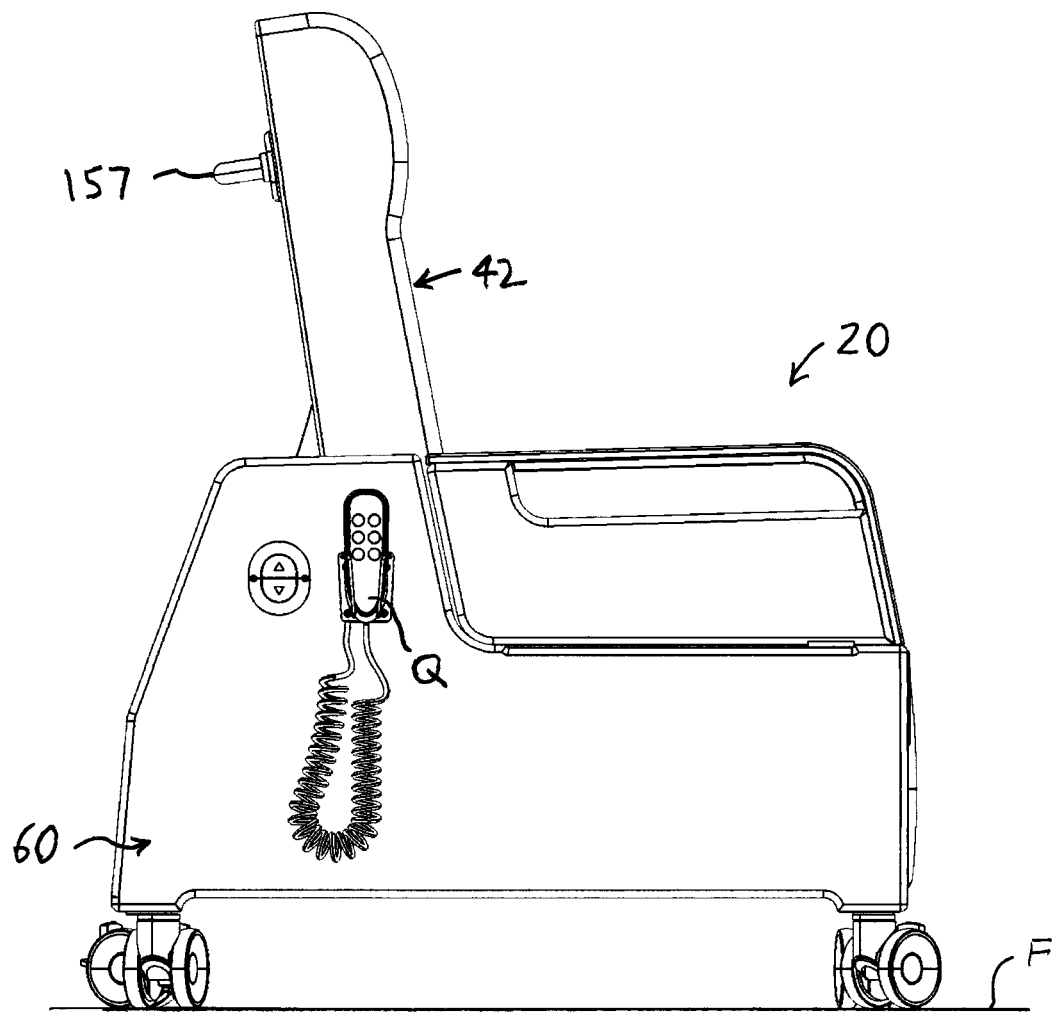
FIG. 1A is a right side view of an embodiment of the patient examination system of the invention.
Figure 1B:
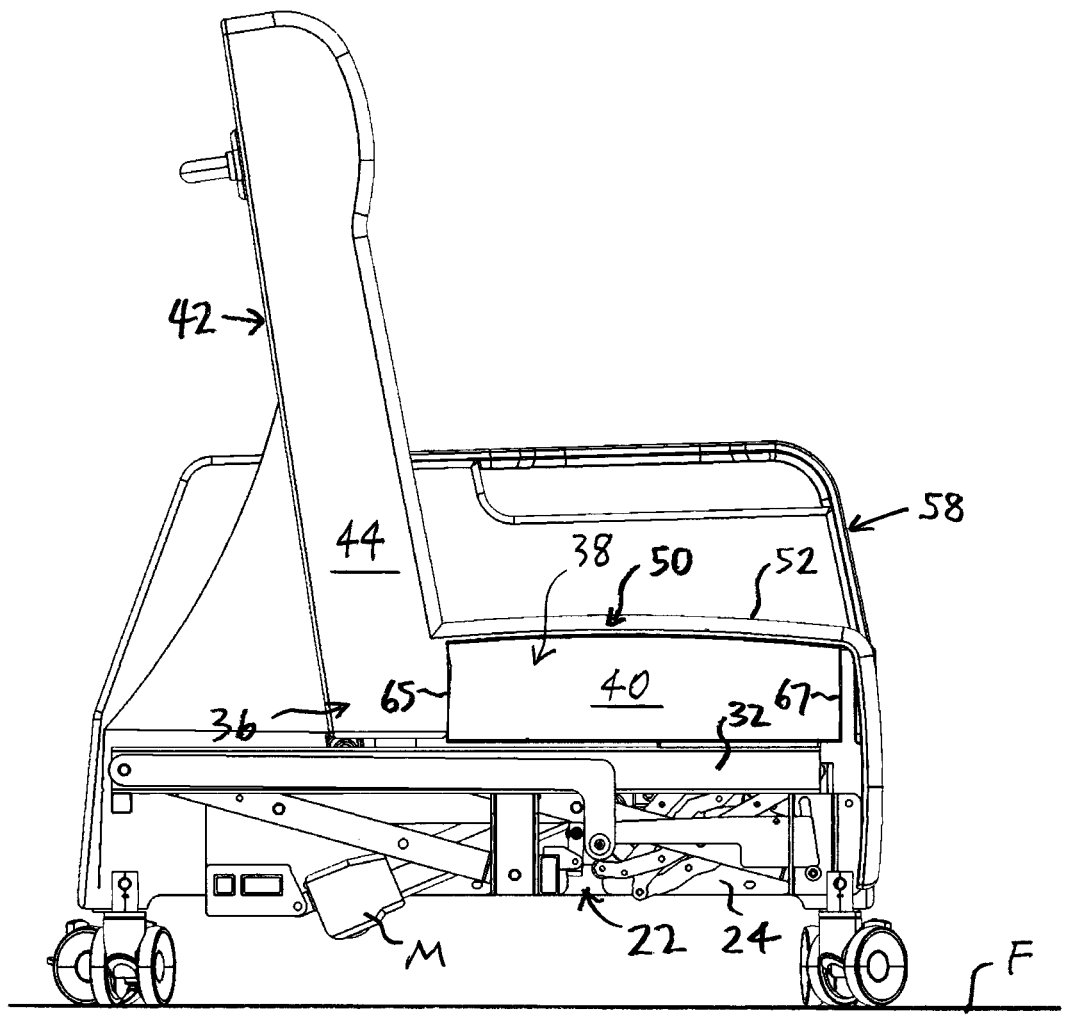
FIG. 1B is a right side view of the patient examination system of FIG. 1A, with certain elements omitted in order to show an embodiment of the frame assembly of the invention in a retracted condition thereof.

In the attached drawings, like reference numerals designate corresponding elements throughout. Reference is first made to FIGS. 1A-18 to describe an embodiment of a patient examination system of the invention indicated generally by the numeral 20. As will be described, the patient examination system for locating a patient (not shown) above a floor "F" supporting the patient examination system 20. In one embodiment, the patient examination system 20 preferably includes a frame assembly 22 (FIGS. 1B, 3B, 3C, 5B, 5C) having one or more lower elements 24 (FIGS. 3B, 5B) at least partially defining a lower side 26 of the frame assembly 22 that is located proximal to the floor "F". Preferably, the patient examination system 20 also includes one or more motion-controlling assemblies 28 (FIG. 5B) connected to the frame assembly 22 for moving one or more selected movable portions 30 of the frame assembly 22 relative to the floor "F". It is also preferred that the selected movable portions 30 include an upper element 32 defining an upper side 34 of the frame assembly 22 that is located distal to the floor "F". As will be described, the upper element 32 preferably is movable by the motion-controlling assembly 28, relative to the lower element 24.

Figure 3A:
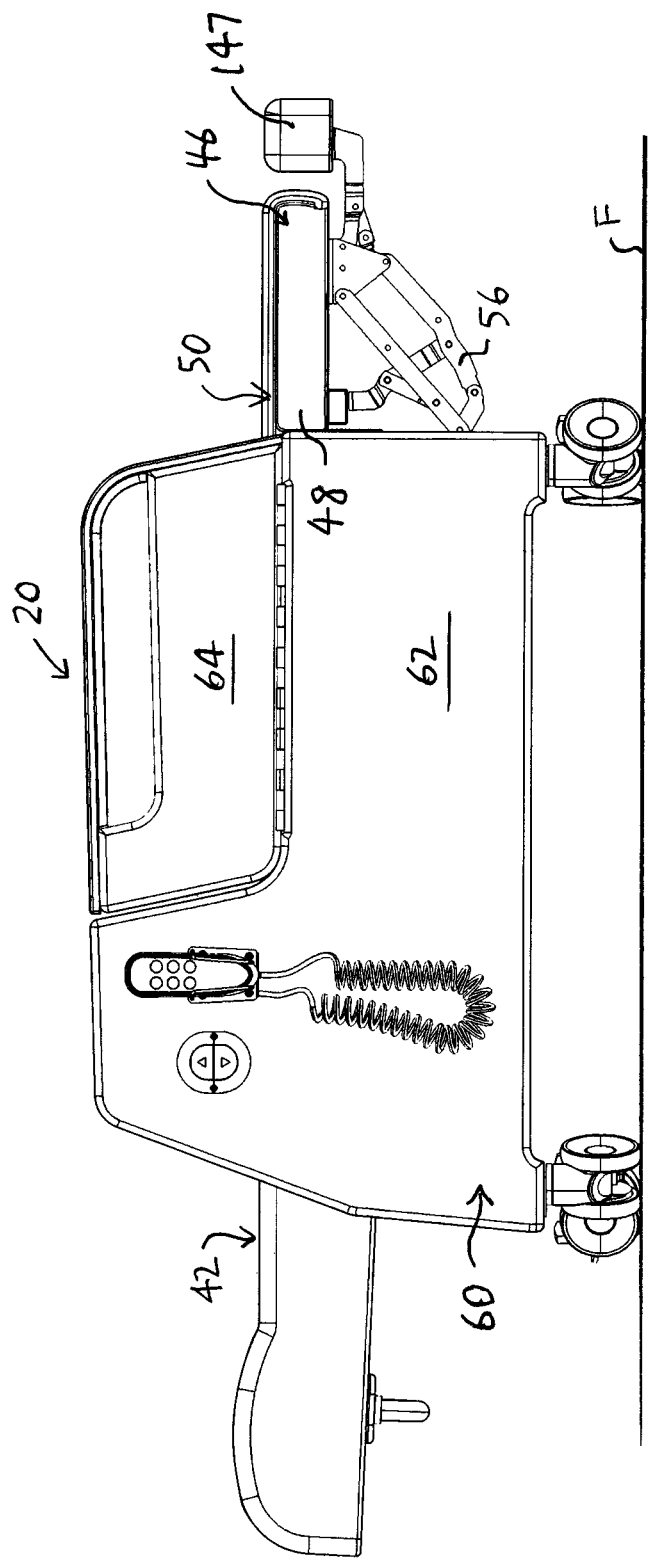
FIG. 3A is a right side view of the patient examination system of FIG. 1A in which the frame assembly is in the retracted condition and a back subassembly is in a substantially horizontal position, drawn at a smaller scale.
Figure 3B:
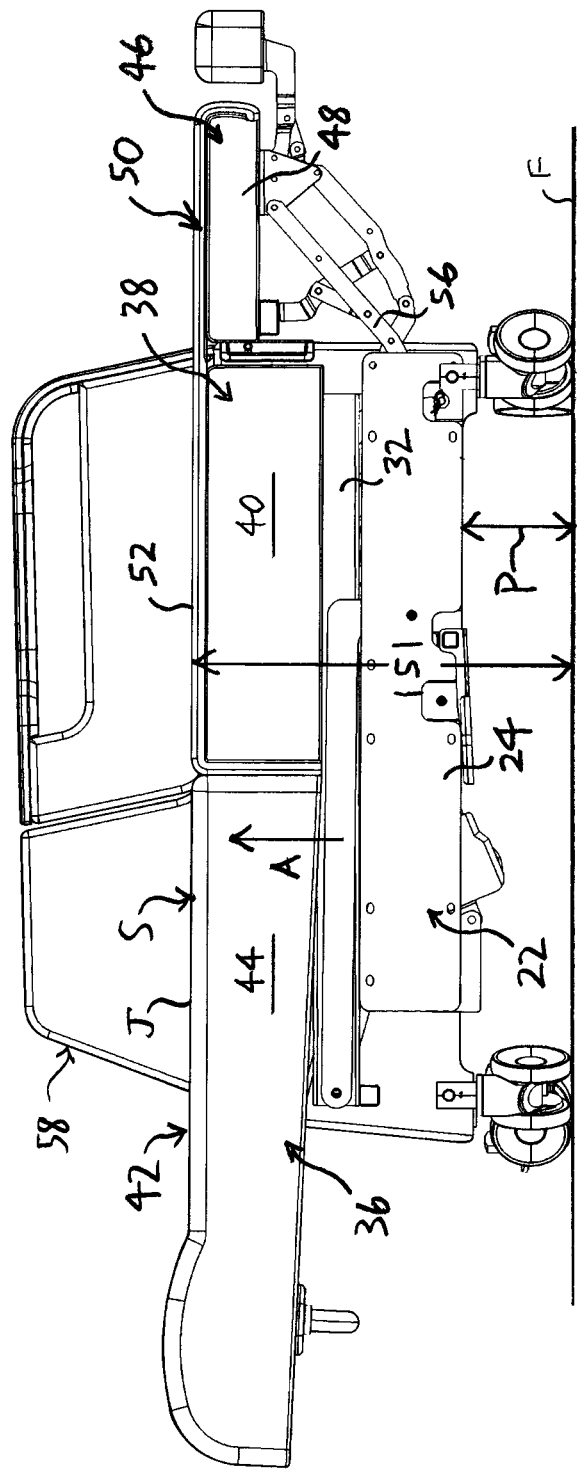
FIG. 3B is a right side view of the patient examination system of FIG. 3A in which certain elements are omitted in order to show the frame assembly in the retracted condition thereof.
Figure 5A:
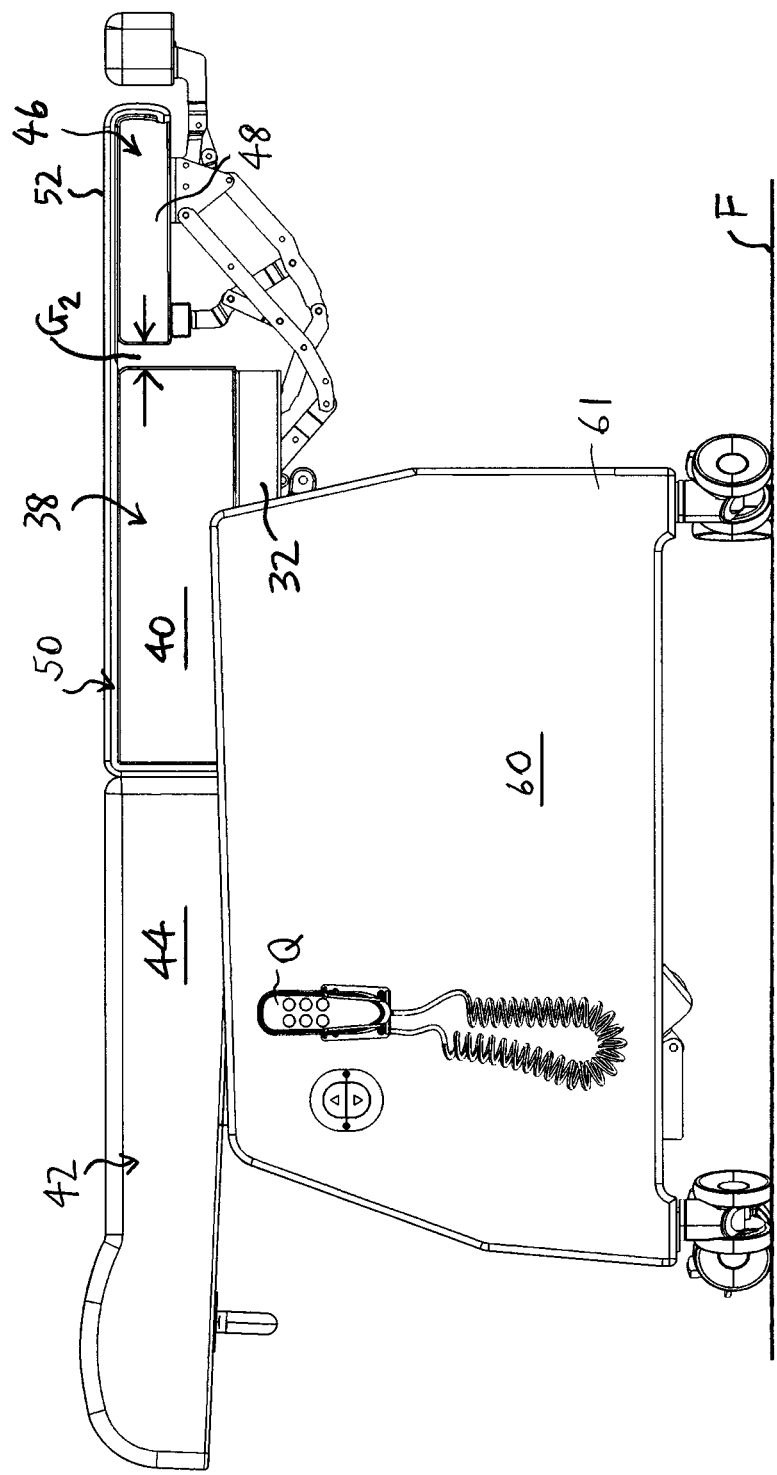
FIG. 5A is a right side view of the patient examination system of FIG. 1A in which the back subassembly is in the horizontal position and the frame assembly is in the extended condition.
Figure 5B:
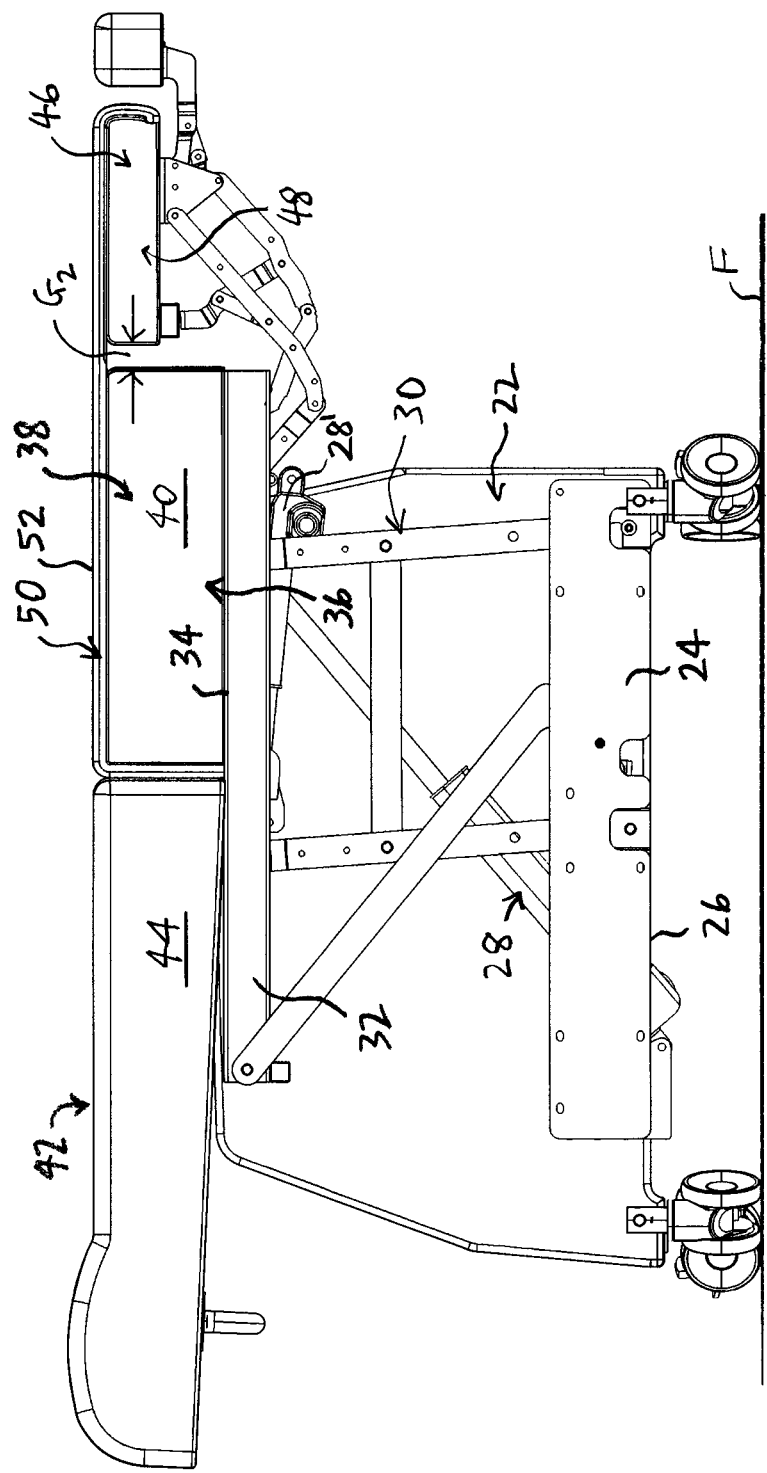
FIG. 5B is a right side view of the patient examination system of FIG. 5A, with certain elements omitted to show the frame assembly in the extended condition.

As can be seen in FIGS. 3B and 5B, the patient examination system 20 preferably also includes a patient support assembly 36 including a seat subassembly 38 having a seat cushion 40 with a top side 59 thereof, a back subassembly 42 having a back cushion 44, and a footrest subassembly 46 having a footrest cushion 48 with an external side 63 thereof. The patient examination system 20 preferably also includes a cover element 50 that covers the top side 59 of the seat cushion 40 and the external side 63 of the footrest cushion 48. The cover element 50 preferably has an exterior surface 52 facing away from the top side 59 and the external side 63, when the cover element 50 is positioned on the seat cushion 40 and on the footrest cushion 48. It will be understood that the patient engages the exterior surface 52 of the cover element 50 when supported by the patient examination system 20, unless an additional layer of material, e.g., paper (not shown), is located between the patient and the exterior surface 52.

Figure 9A:
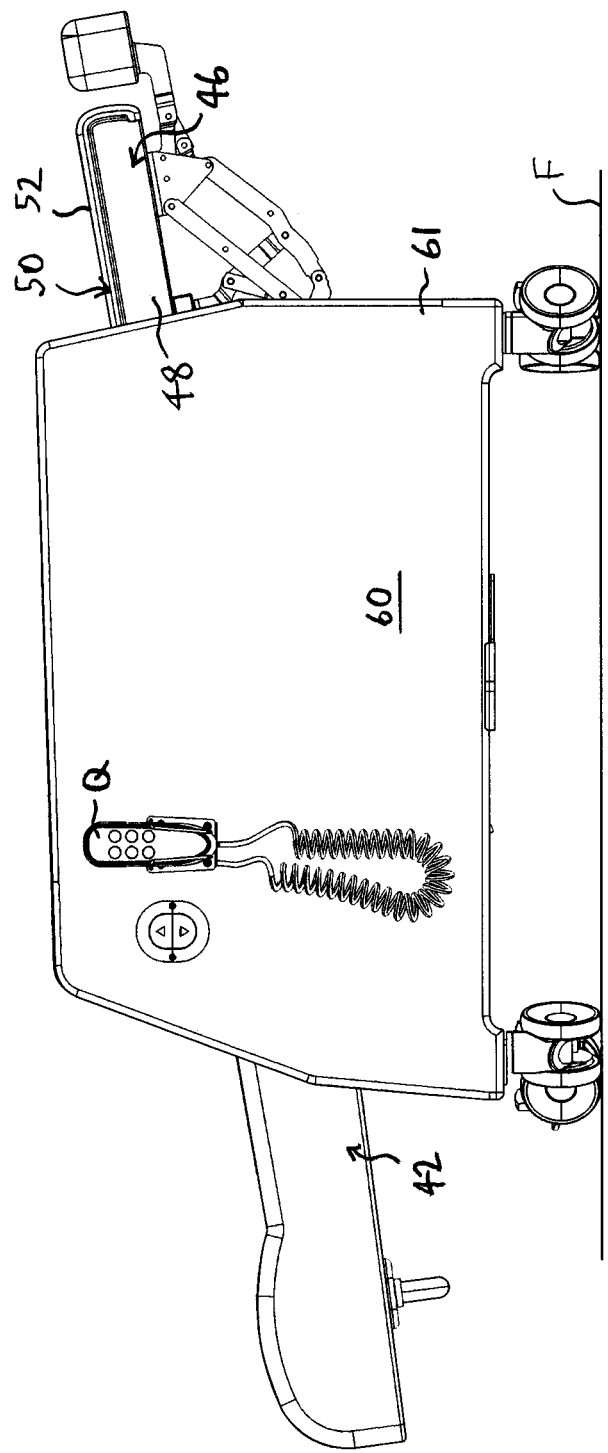
FIG. 9A is a right side view of the patient examination system of FIG. 1A in a Trendelenburg position.
Figure 9B:
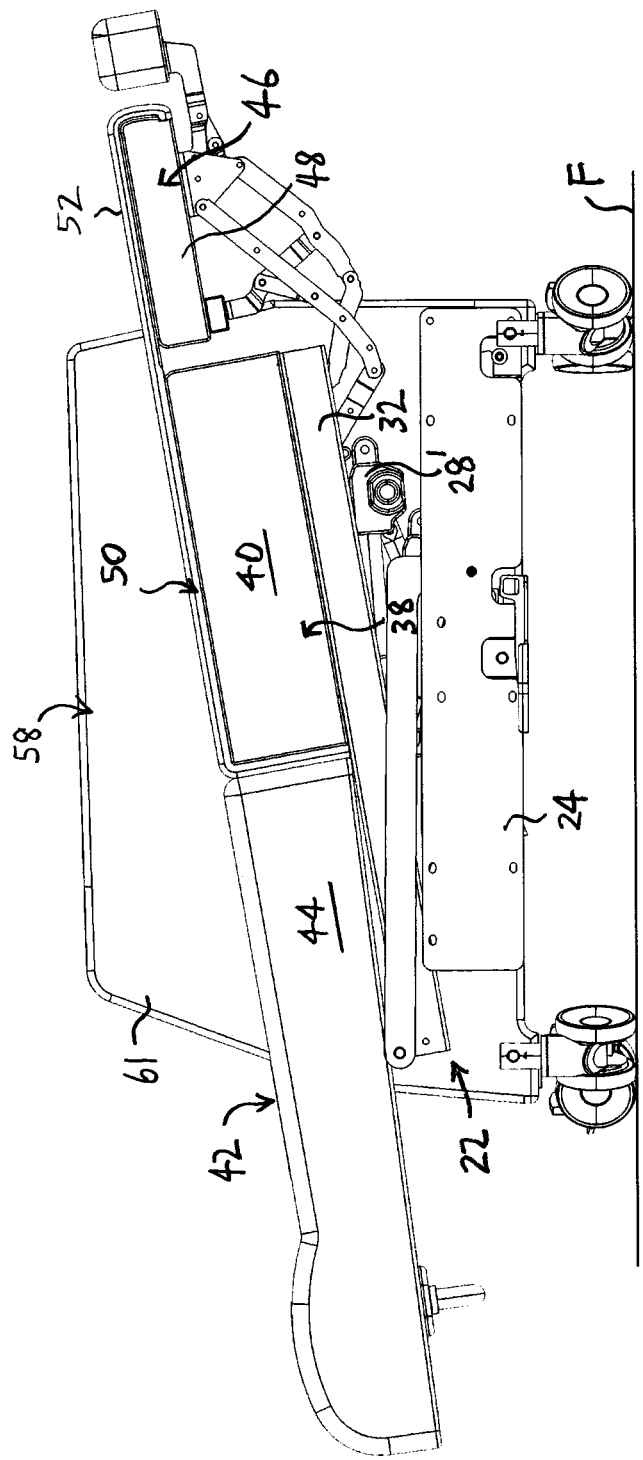
FIG. 9B is a right side view of the patient examination system of FIG. 9A with certain elements omitted, in order to show the frame assembly.
Figure 9C:
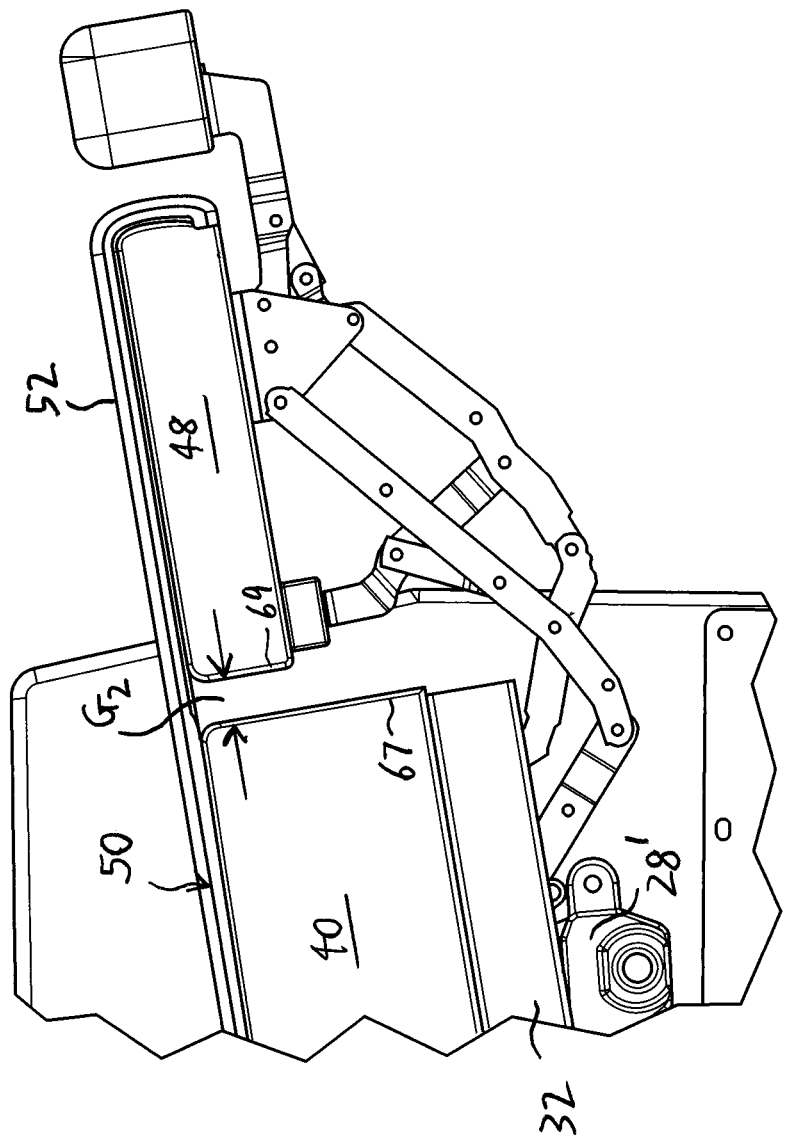
FIG. 9C is a portion of the right side view of FIG. 9B, drawn at a larger scale.

It is preferred that the seat subassembly 38 is secured to the upper element 32 of the frame assembly 22, to locate the top side 59 of the seat cushion 40 distal to the upper element 32. The frame assembly 22 is configured to move the seat subassembly 38 between a lowered position thereof (FIG. 1A) and a raised position thereof (FIG. 4), to at least one intermediate seat positions therebetween, and to locate the seat subassembly in one or more Trendelenburg positions (FIG. 9A).

Figure 3C:
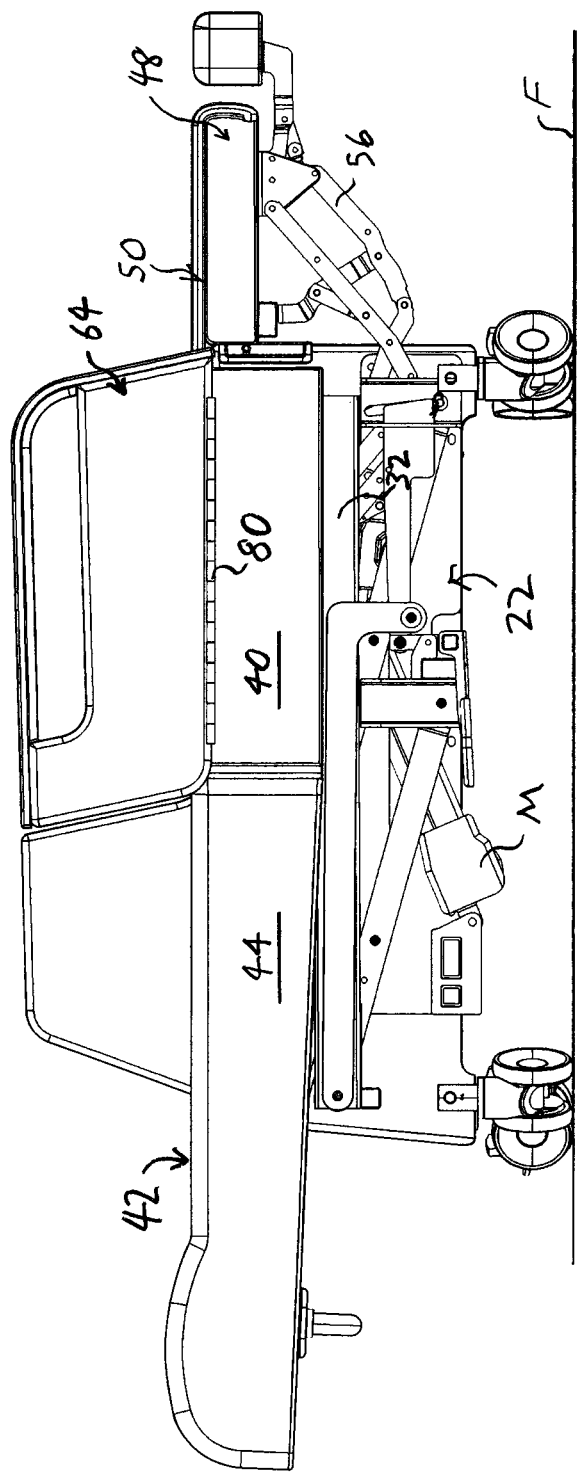
FIG. 3C is a right side view of the patient examination system of FIG. 3B in which another element is omitted.
Figure 3D:
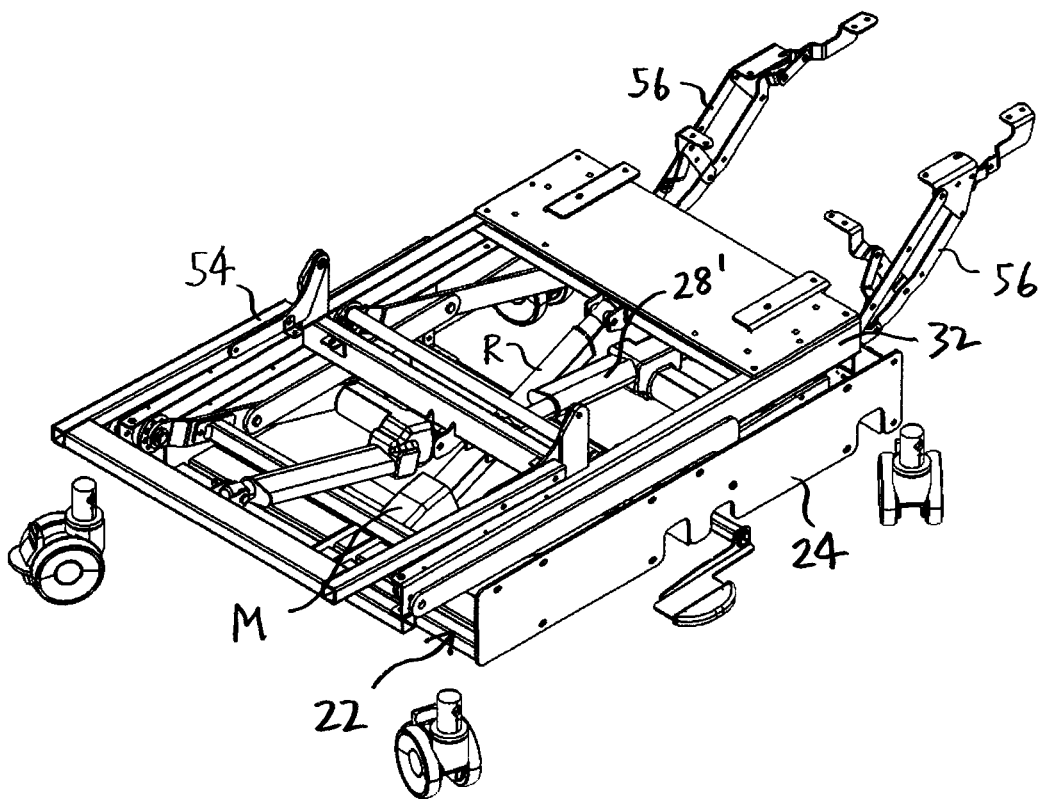
FIG. 3D is an isometric view of the frame assembly in the retracted condition thereof, along with certain additional elements, drawn at a smaller scale.
Figure 5C:
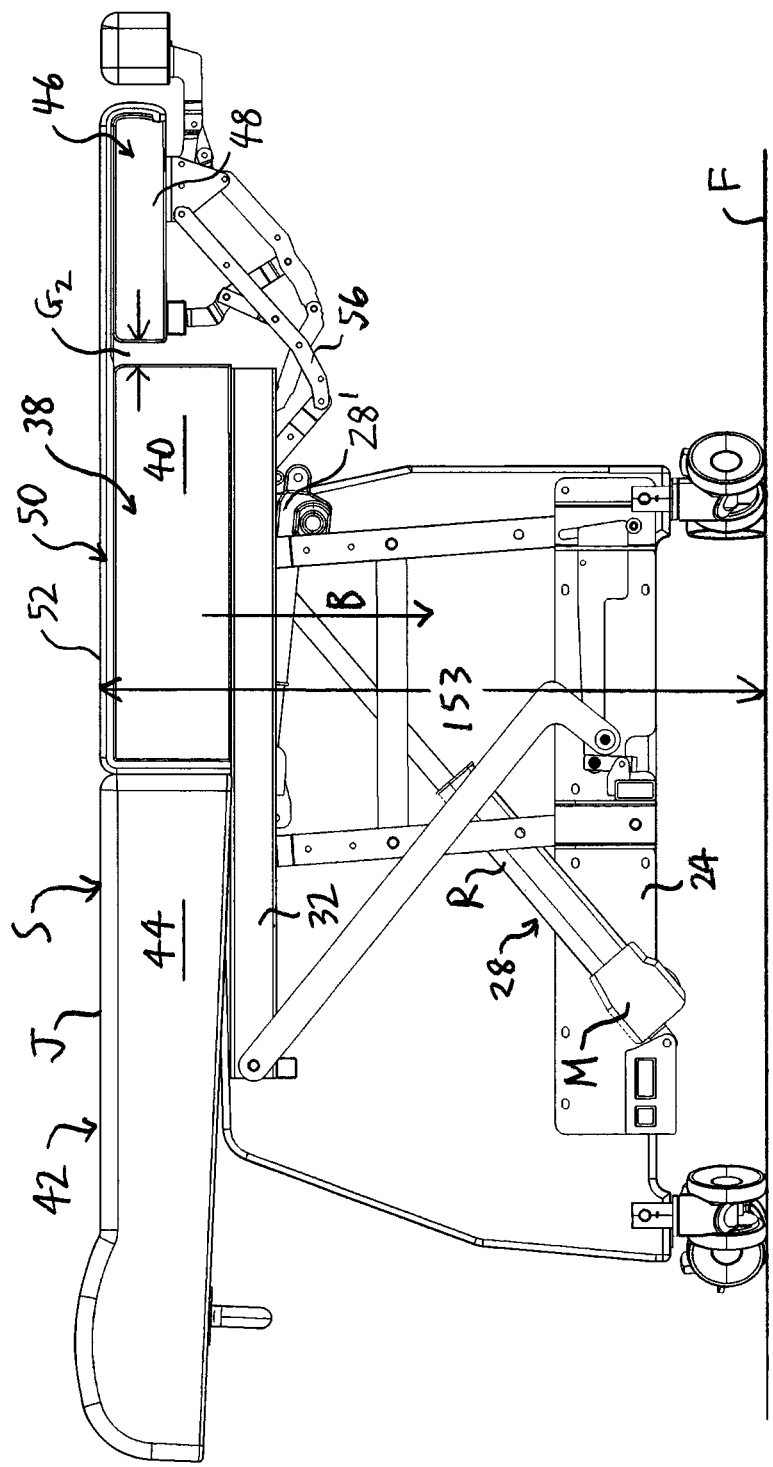
FIG. 5C is a right side view of the patient examination system of FIG. 5B, with certain additional elements omitted.
Figure 5D:
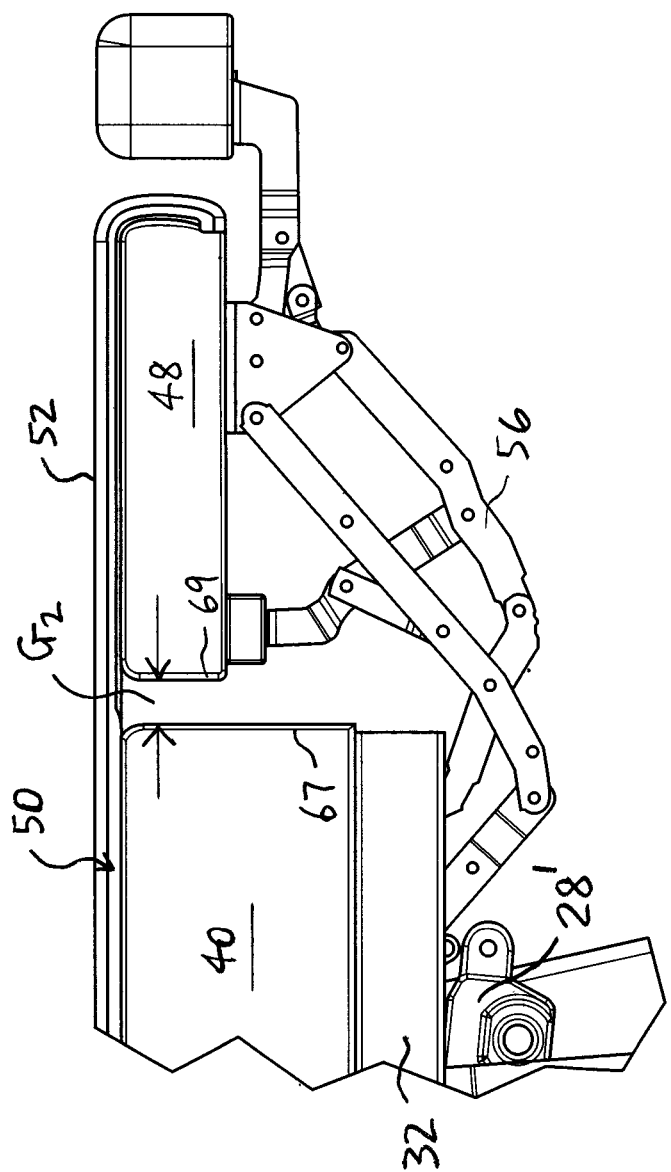
FIG. 5D is a portion of the right side view of FIG. 5C, drawn at a larger scale.
Figure 5E:
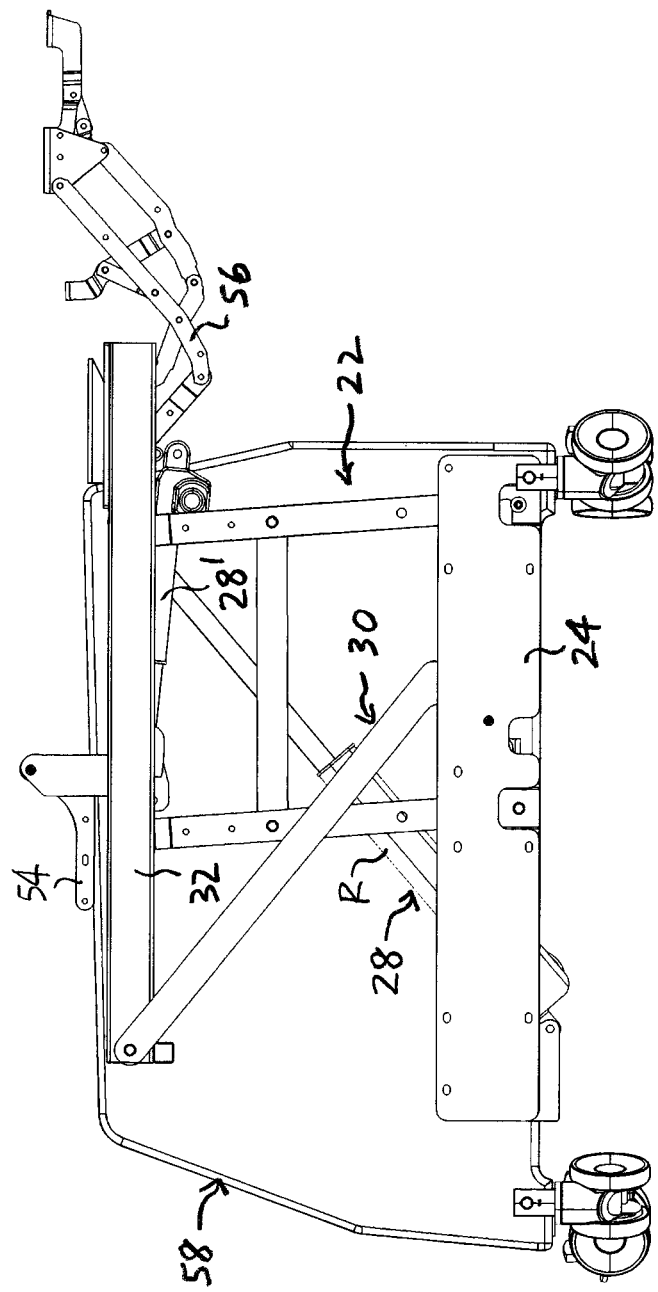
FIG. 5E is a right side view of the patient examination system of FIG. 5C with certain elements omitted, drawn at a smaller scale.
Figure 5F:
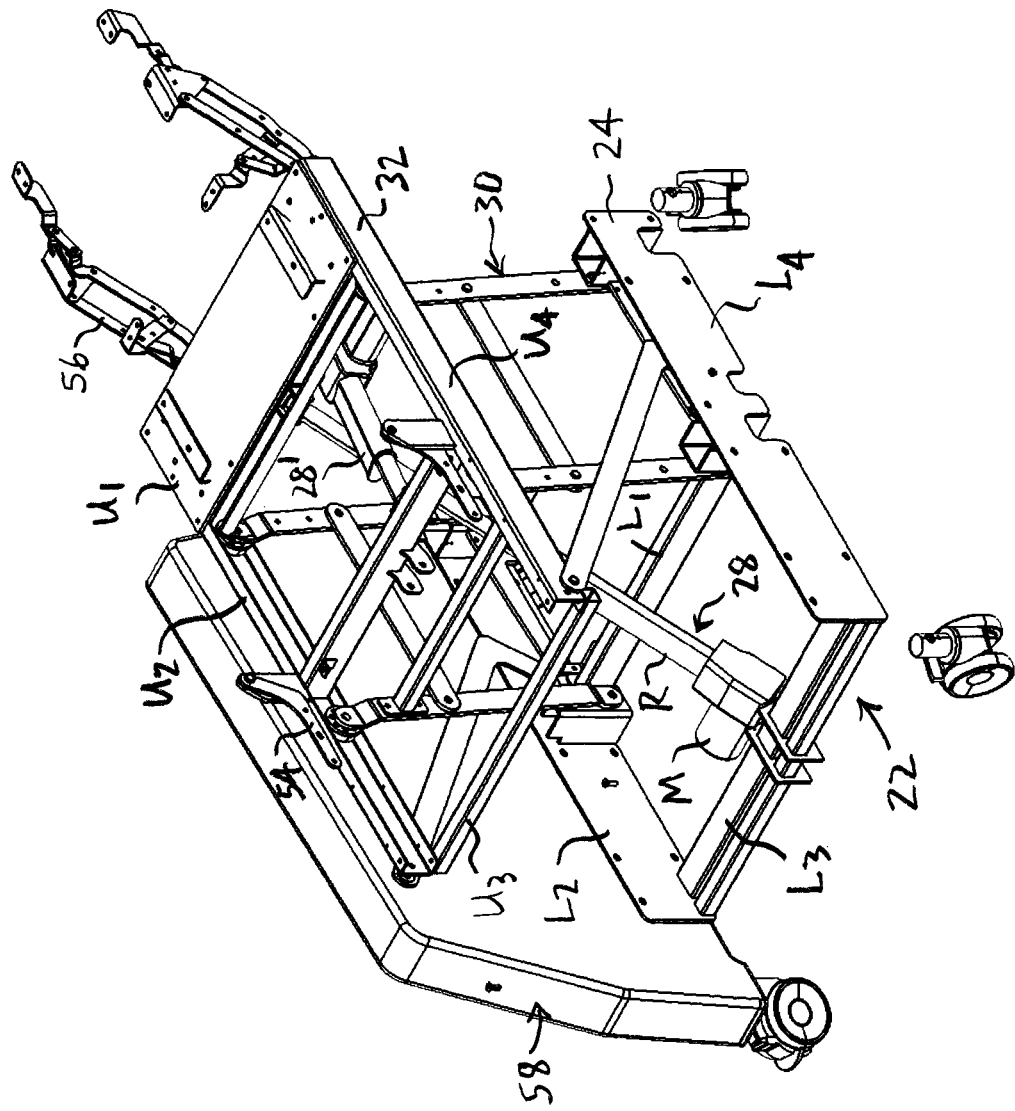
FIG. 5F is an isometric view of the patient examination system of FIG. 5A with certain elements omitted to show the frame assembly in the extended condition.
Figure 6A:
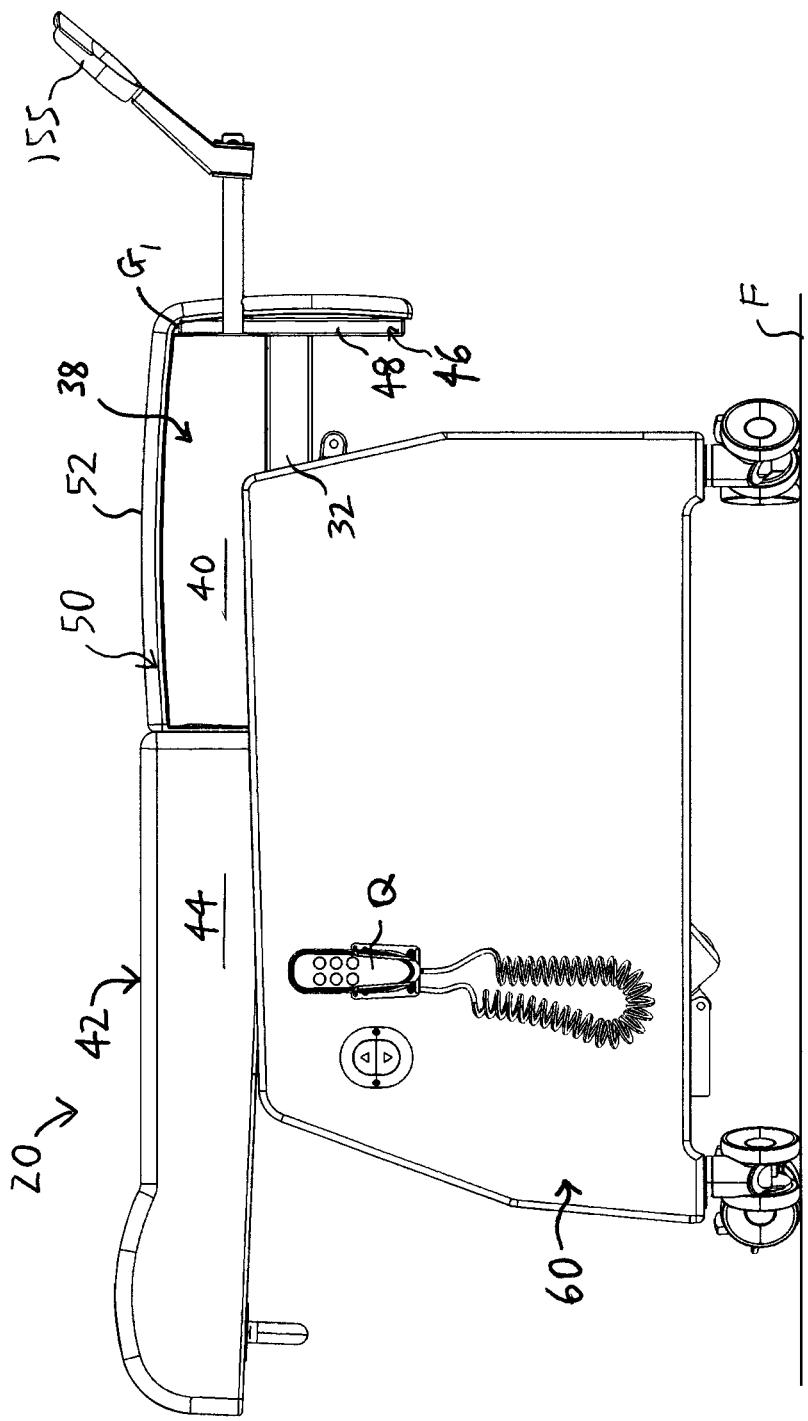
FIG. 6A is a right side view of the patient examination system of FIG. 5A in which the footrest subassembly is in a retracted position and stirrup elements are mounted to the seat subassembly.
Figure 6B:
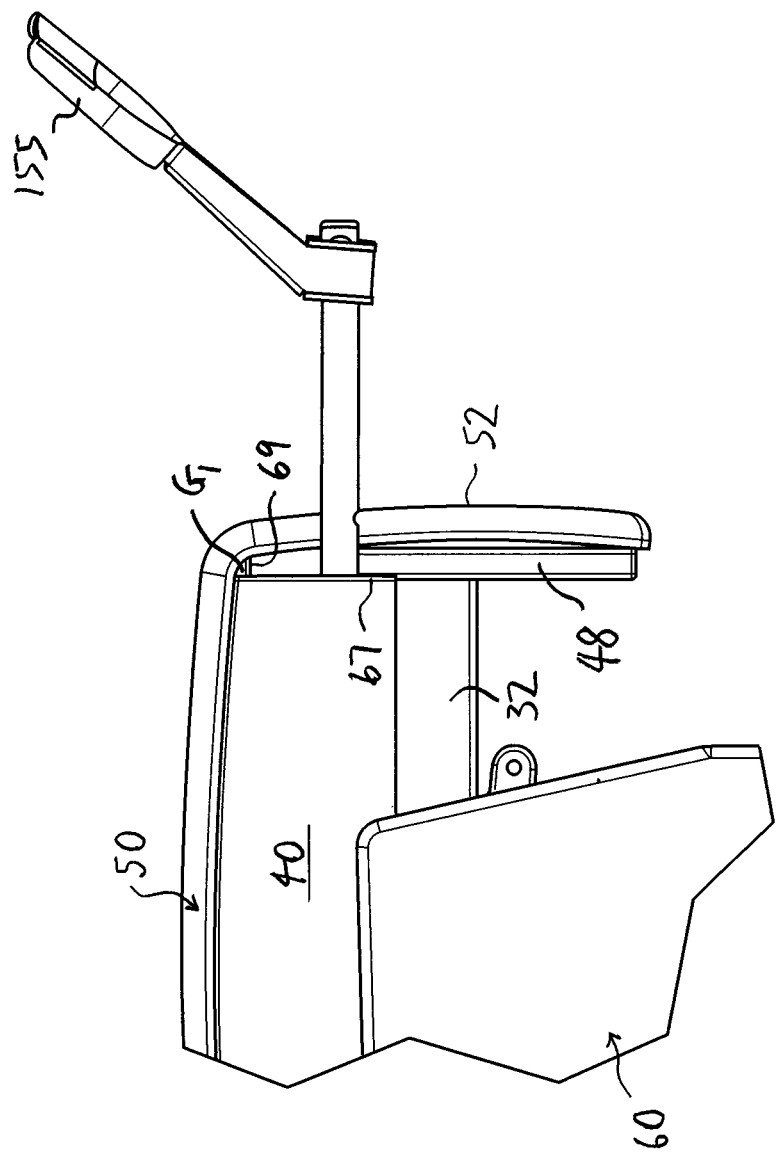
FIG. 6B is a portion of the right side view of FIG. 6A, drawn at a larger scale.

The back subassembly 42 preferably is connected with the upper element 32 by a back linkage subassembly 54 (FIGS. 3D, 5E). The back linkage subassembly 54 is configured to move the back subassembly 42 relative to the frame assembly 22 between an upright position thereof (FIG. 1A) and a horizontal position thereof (FIG. 3A), to one or more intermediate back positions therebetween, and to locate the back subassembly in one or more Trendelenburg positions (FIG. 9A).

Figure 4:
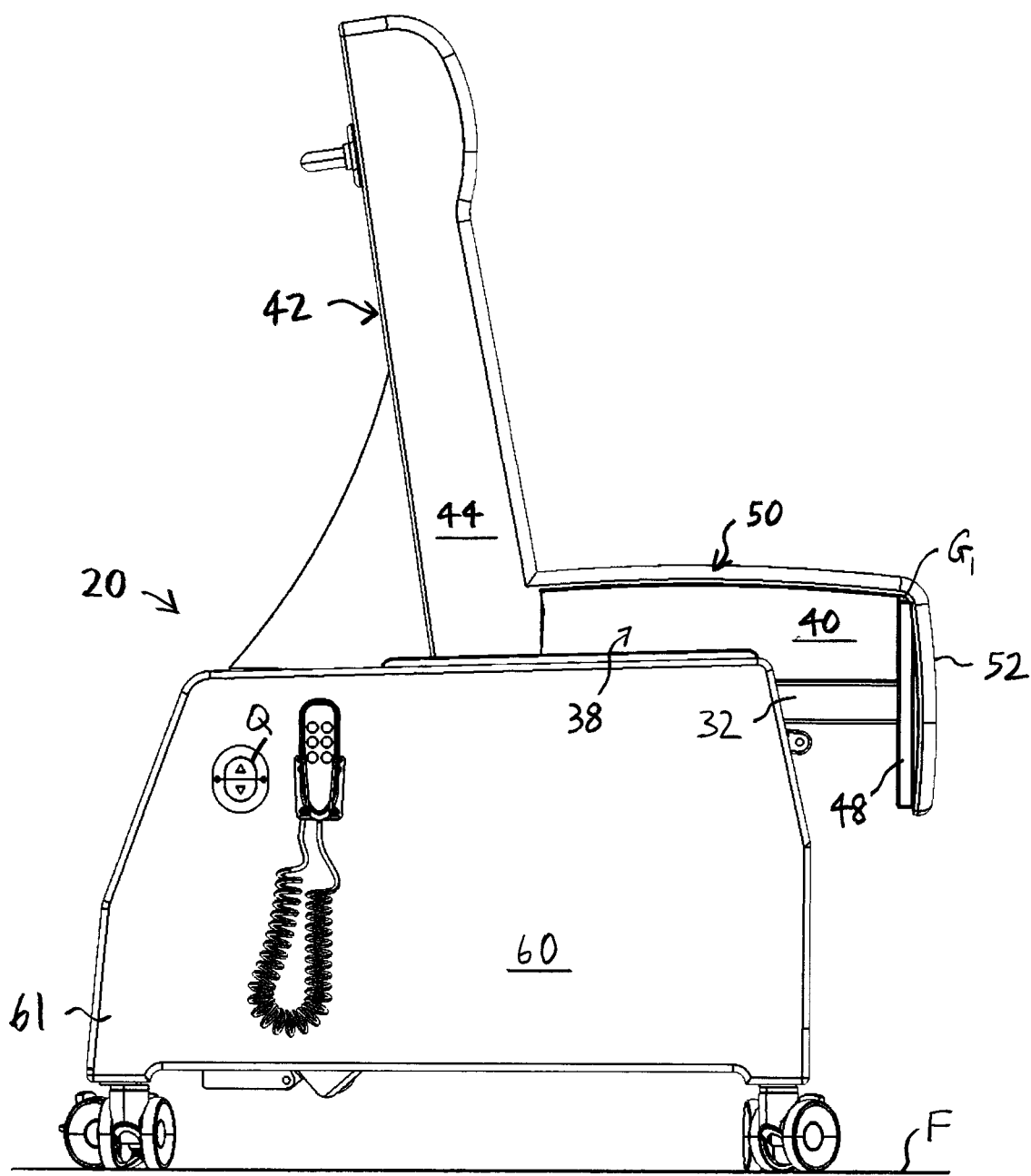
FIG. 4 is a right side view of the patient examination system of FIG. 1A in which the frame assembly is in an extended condition, drawn at a larger scale.

It is also preferred that the footrest subassembly 46 is connected to the upper element 32 of the frame assembly 22 by a footrest linkage subassembly 56 (FIGS. 3D, 5C, 5E). The footrest linkage subassembly 56 supports the footrest cushion 48 to locate the external side 63 of the footrest cushion 48 distal to the footrest linkage subassembly 56 (FIGS. 3C, 5C). The footrest linkage subassembly 56 preferably is configured to move the footrest subassembly 46 between a retracted position thereof in which the footrest cushion 48 is positioned orthogonally to the floor "F" to partially define a first gap "$G_1$" between the seat cushion 40 and the footrest cushion 48 (FIGS. 4, 6A, 6B), and an extended position thereof (FIGS. 3C, 5A-5D), in which the external side 63 of the footrest cushion 48 is aligned with the top side 59 of the seat cushion 40, to partially define a second gap "$G_2$" between the seat cushion 40 and the footrest cushion 48.

The cover element 50 preferably extends continuously over the top side 59 of the seat cushion 40 and the external side 63 of the footrest cushion 48 to bridge the first gap "$G_1$" when the footrest subassembly 46 is in its retracted position, and to bridge the second gap "$G_2$" when the footrest subassembly 46 is in its extended position.

As noted above, the cover element 50 covers the top side 59 of the seat cushion 40, and the external side 63 of the footrest cushion 48. The cover element 50 also covers the gap between the seat cushion 40 and the footrest cushion 48, which varies between the relatively small gap "$G_1$" and the comparatively larger gap "$G_2$", depending on whether the footrest subassembly 46 is in its retracted position or its extended position. The cover element 50 is important because it enables the user to clean the cover element 50 relatively easily. Because the cover element 50 covers the top side 59 and the external side 63 and the gaps "$G_1$", "$G_2$", cleaning the patient examination system 20, if necessary, is relatively simplified.

Figure 2A:
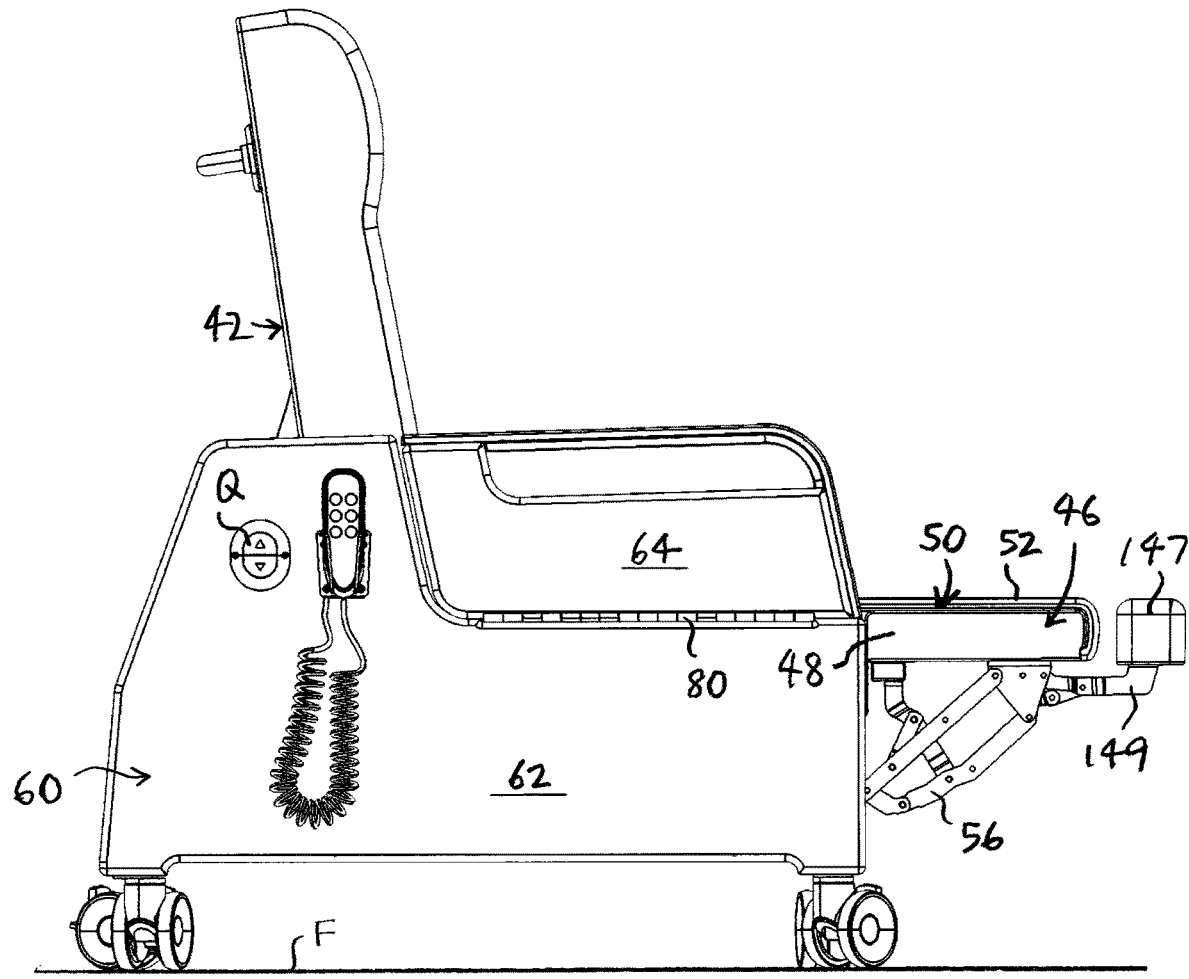
FIG. 2A is a right side view of the patient examination system of FIG. 1A in which a footrest subassembly is in an extended position thereof, drawn at a smaller scale.
Figure 2B:
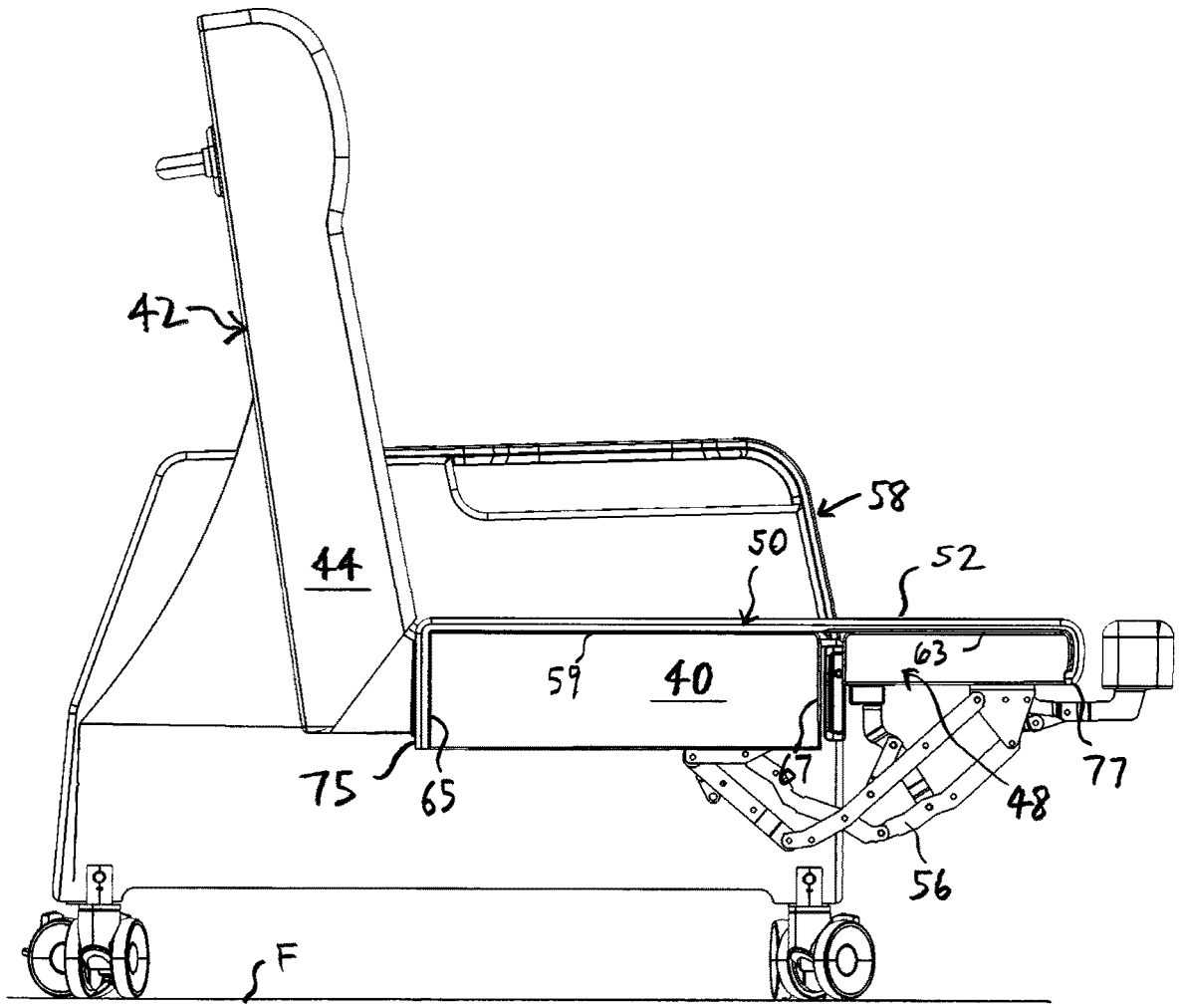
FIG. 2B is a right side view of the patient examination system of FIG. 2A, with certain elements omitted in order to show a seat subassembly and the footrest subassembly.
Figure 2C:
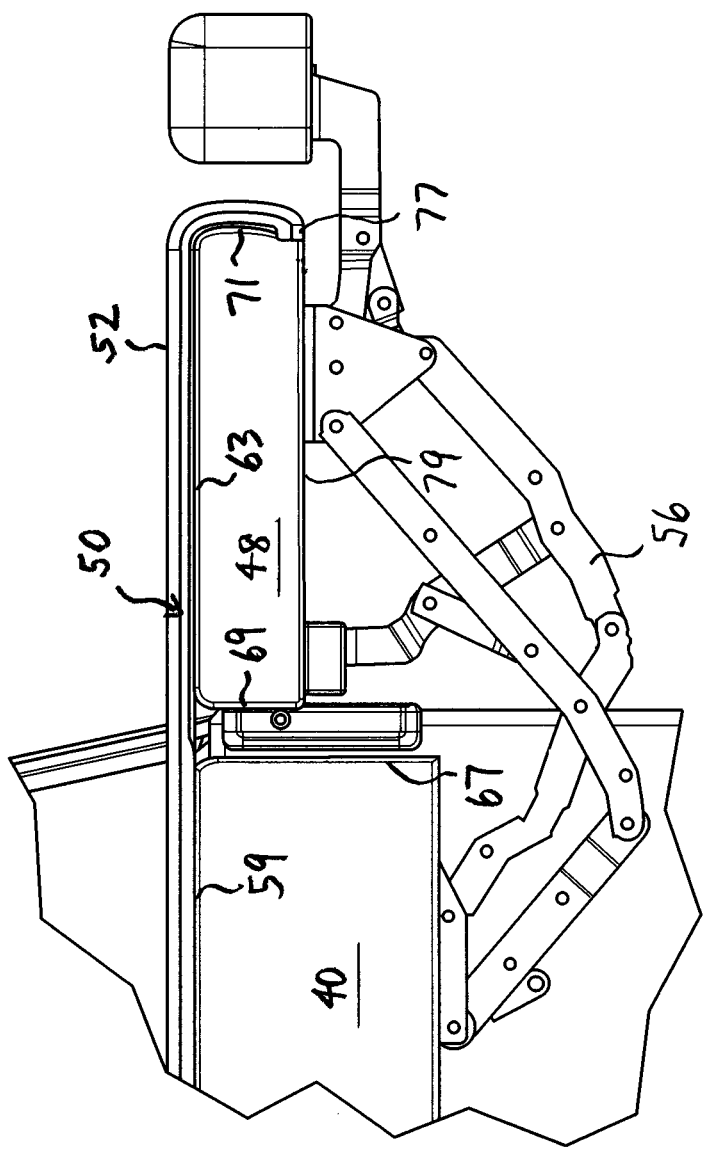
FIG. 2C is a portion of the right side view of FIG. 2B, drawn at a larger scale.

As can be seen in FIGS. 2B and 2C, in one embodiment, the seat cushion 40 preferably extends between an inner end 65 thereof located adjacent to the back cushion 44, and an outer end 67 that is located proximal to the footrest cushion 48. The footrest cushion 48 extends between an inner end 69 thereof that is proximal to the outer end 67 of the seat cushion 40, and an outer end 71 thereof that is located distal to the outer end 67 of the seat cushion 40. Preferably, the cover element 50 extends over the top side 59 of the seat cushion 40 and over the external side 63 of the footrest cushion 48, from the inner end 65 of the seat cushion 40 to the outer end 71 of the footrest cushion 48.

As can be seen in FIGS. 2B and 2C, the cover element 50 preferably extends between a first end 75 thereof and a second end 77 thereof. Preferably, the first end 75 is secured to the seat cushion 40 at the inner end 65 of the seat cushion 40. Those skilled in the art would be aware of suitable fastening means for fastening the first end 75 to seat cushion 40 at the inner end 65.

It is also preferred that the cover element 50 covers the outer end 71 of the footrest cushion 46. Preferably, the second end 77 is secured to the footrest cushion 48 at the outer end 71 of the footrest cushion 48. In one embodiment, the second end 77 may be secured to an internal side 79 of the footrest cushion 48. As can be seen in FIG. 2C, the internal side 79 preferably is positioned opposite to the external side 63 of the footrest cushion 48. Those skilled in the art would be aware of suitable fastening means for fastening the second end 77 to the footrest cushion 48 so that the cover element 50 covers the external side 63 and the outer end 71 of the footrest cushion 48.

Those skilled in the art would appreciate that the upright position of the back subassembly preferably is not orthogonal to the floor "F". The upright position is any suitable generally upright position. For example, the upright position may be at approximately 80° relative to the floor "F".

Those skilled in the art would appreciate that the one or more motion-controlling assemblies 28 may include any suitable means for initiating movement controllable by an operator or, if preferred, by the patient for precise positioning of certain portions of the patient examination system 20, to locate the patient in one or more selected positions. In one embodiment, the motion-controlling assembly 28 preferably is configured to move the upper element 32 vertically relative to the floor between lowered and raised positions thereof (FIGS. 3A, 5A). For example, in FIG. 3B, the frame assembly 22 is shown in a retracted condition, in which the upper element 32 is positioned proximal to the lower element 24. In FIGS. 5B and 5C, the frame assembly 22 is shown in an extended condition, in which the upper element 32 is positioned distal to the lower element 24. It will be understood that the frame assembly 22 may be moved to a number of intermediate conditions, in which the upper element 32 is located between its raised and lowered positions. As can also be seen, e.g., in FIG. 9B, the frame assembly 22 is also movable to Trendelenburg conditions, in which the upper element 32 is positioned to define an acute angle between the upper element 32 and the floor "F". From the foregoing, it can be seen that the vertical movement of the upper element 32 causes corresponding vertical movement of the seat subassembly 38, the back subassembly 42, and the footrest subassembly 46.

Those skilled in the art would be aware of suitable motion-controlling assemblies. For instance, in one embodiment, the motion-controlling assembly may include one or more suitable motors "M" operatively coupled with a telescoping ram subassembly "R" (FIG. 5C). The motion-controlling assembly 28 preferably also includes one or more suitable controllers "Q" (FIGS. 1A, 5A).

For instance, in FIGS. 3B and 5C, it can be seen that, when the frame assembly 22 is moved from its retracted condition (FIG. 3B) to its extended condition (FIG. 5C), the upper element 32 is moved vertically upwardly, in the direction indicated by arrow "A" in FIG. 3B. Similarly, when the frame assembly 22 is moved from its extended condition (FIG. 5C), to its retracted condition (FIG. 3B), the upper element 32 is vertically lowered, as indicated by arrow "B" in FIG. 5C.

As noted above, the seat cushion 40, the back linkage subassembly 54, and the footrest linkage subassembly 56 are all mounted to the upper element 32. Accordingly, those skilled in the art would appreciate that movement of the upper element 32 also causes corresponding movement of each of the seat subassembly 38, the back subassembly 42, and the footrest subassembly 46.

As is known, in a Trendelenburg position, the patient is positioned with the pelvis higher than the head. Those skilled in the art would appreciate that, in order for the patient examination system 20 to be configured in a Trendelenburg position, for example, as shown in FIGS. 9A-9D, the upper element 32 is positioned at one or more acute angles relative to the lower element 24.

From the foregoing, it can be seen that the patient examination system 20 may be configured in a variety of selected states. For instance, in FIG. 1A, the system 20 is configured in a first sitting state, in which the patient is supported in a lowered sitting position. In FIG. 4, the system 20 is configured in a second sitting state, in which the patient is supported in a raised sitting position. It will be understood that the system 20 may be configured in a variety of intermediate positions, e.g., vertically intermediate between the lowered and raised seat cushion positions illustrated in FIGS. 1A and 4 respectively.

Those skilled in the art would appreciate that the reconfiguration of the system 20 from the first sitting state to the second sitting state, is the result of the frame assembly 22 being moved from its retracted condition (in which the seat subassembly 38 is in its lowered position) to its extended condition (in which the seat subassembly 38 is in its raised position).

It will be understood that the back cushion 44 is positionable in a horizontal position of the back subassembly 42 (FIG. 3A), in which the back cushion 44 is horizontal, or substantially horizontal (e.g., substantially parallel to the upper element 32), and the upright position of the back subassembly 42 (FIG. 1A), in which the back cushion 44 is positioned to define an acute angle between the back cushion 44 and the upper element 32. As noted above, the back subassembly 42 may be at approximately 80° to the floor "F" when it is in the upright position. As can be seen in FIGS. 3D and 5E, the back cushion 44 preferably is connected to the upper element 32 by the back linkage subassembly 54.

It will be understood that the upper element 32 may include a number of discrete elongate elements ("$U_1$"-"$U_4$") that are secured together (FIG. 5E). Similarly, the lower element 24 may include discrete elements ("$L_1$"-"$L_4$") that are secured together (FIG. 5E). The frame assembly 22 preferably also includes the movable portions 30 or intermediate elements that are located generally between the lower and upper elements 24, 32, to connect the lower and upper elements 24, 32. The intermediate elements 30 preferably are configured to provide parallel linkages or such other arrangements as are suitable to position the upper element 32 as desired relative to the lower element 24, using the one or more motion-controlling assemblies 28. As can be seen, e.g., in FIG. 5E, in one embodiment, the motion-controlling assembly 28 preferably includes the motor "M" mounted to the lower element and the telescoping ram "R" that is connected to the upper element 32, for vertical movement of the upper element 32 relative to the lower element 24. The frame assembly may include a second motion-controlling assembly 28', as can be seen in FIGS. 3D, 5B-5F, 9B, and 9C.

Figure 8:
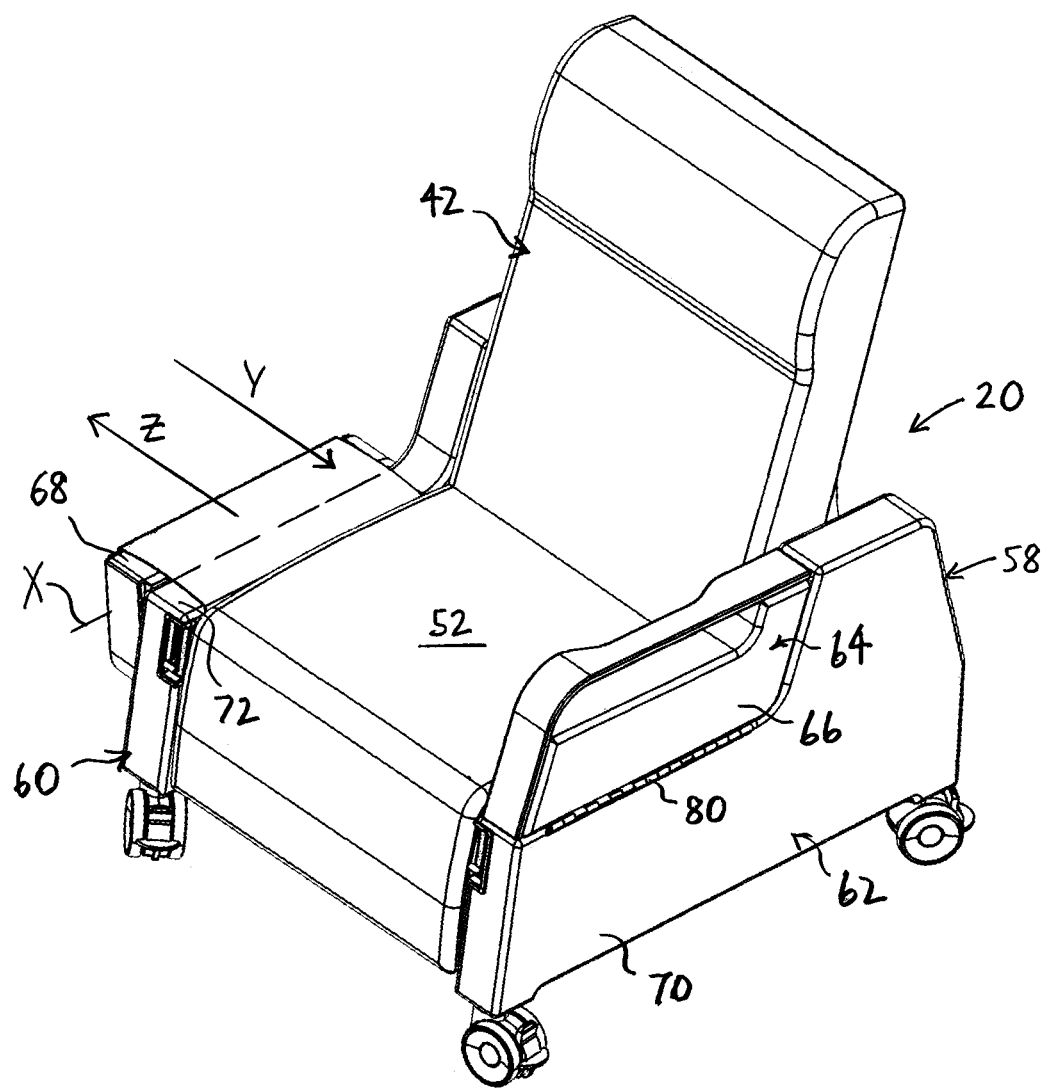
FIG. 8 is an isometric view of the patient examination system of FIG. 7.

In one embodiment, the patient examination system 20 preferably additionally includes a left arm assembly 58 and a right arm assembly 60 positioned on opposite sides of the seat subassembly 38 (FIG. 8). Preferably, each of the left and the right arm assemblies 58, 60 are secured to opposite sides of the lower element 24 of the frame assembly 22.

Figure 9D:
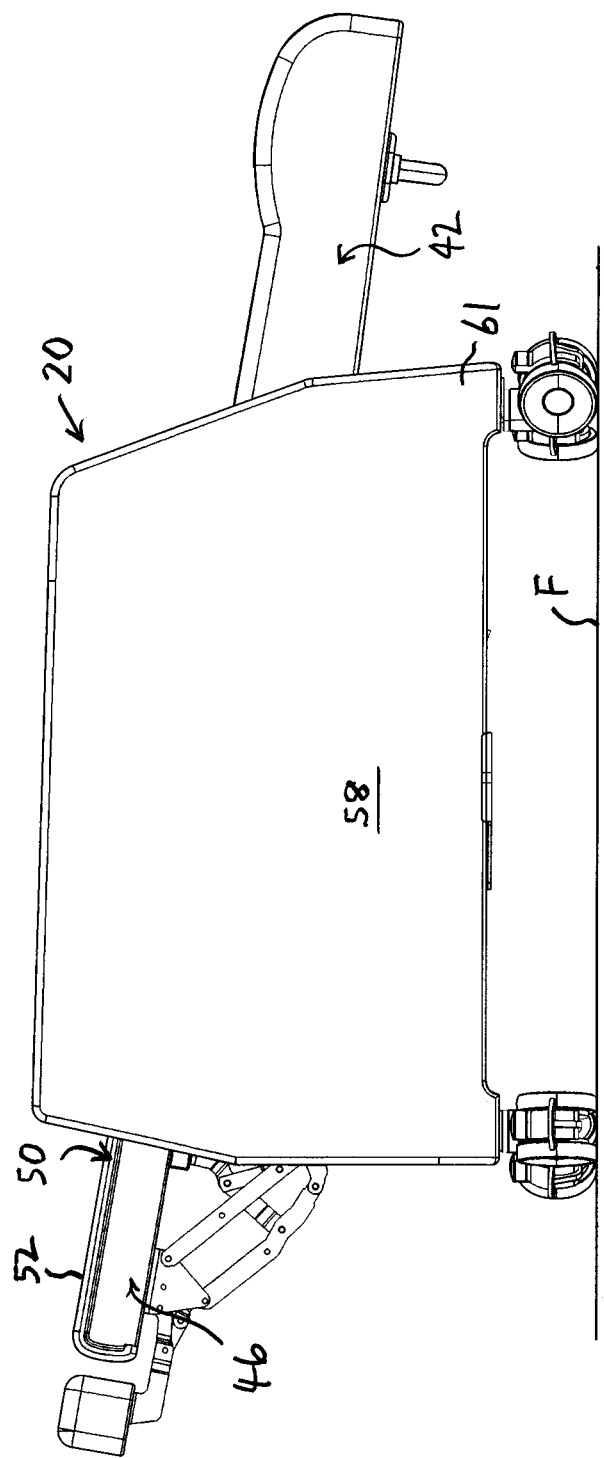
FIG. 9D is a left side view of the patient examination system as illustrated in FIGS. 9A and 9B, drawn at a smaller scale.
Figure 9E:
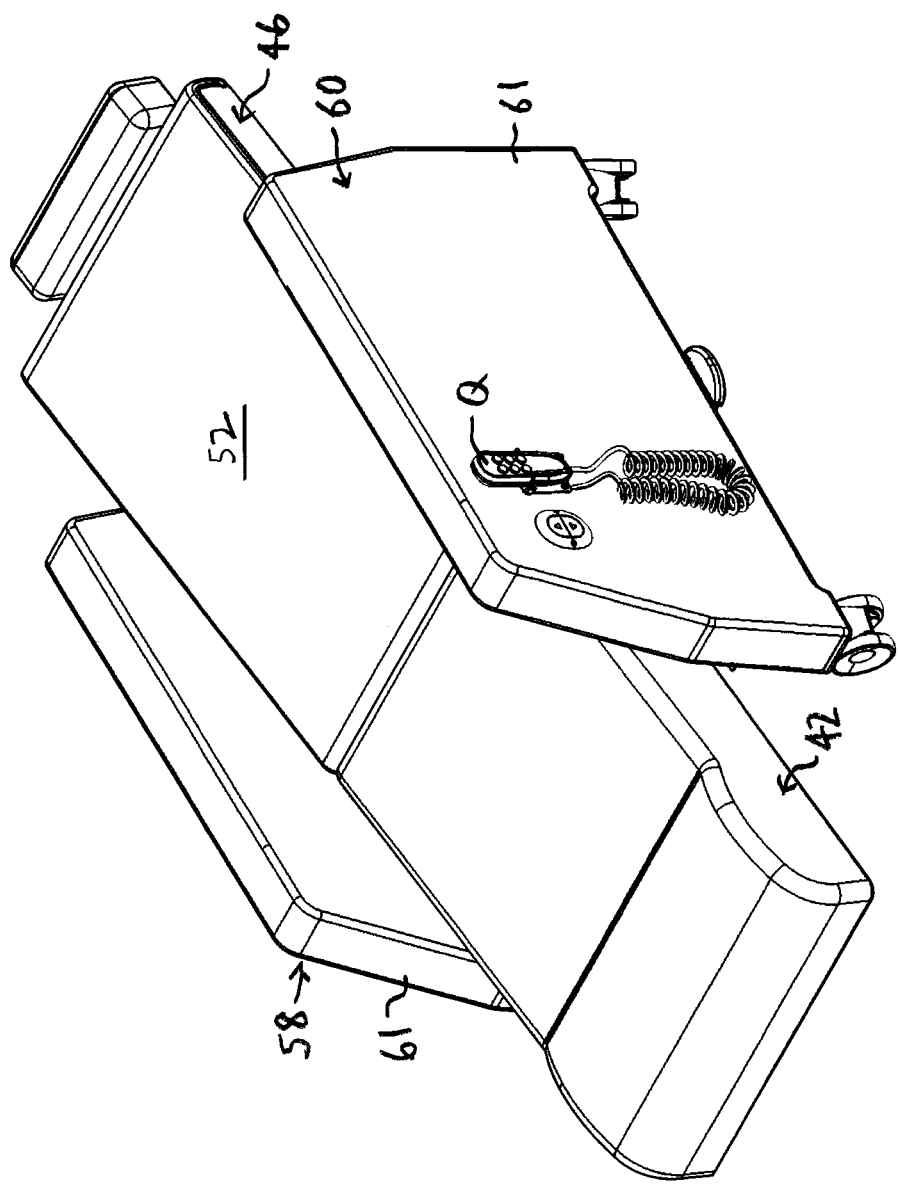
FIG. 9E is an isometric view of the patient examination system of FIGS. 9A-9D.

As can be seen, e.g., in FIGS. 4, 5A, and 9D, in one embodiment, each of the left and right arm assemblies 58, 60 preferably includes only one body portion 61.

However, in an alternative embodiment, it is preferred that each of the left and right arm assemblies 58, 60 includes a lower portion 62 secured to the lower element 24 of the frame assembly 22, and an upper portion 64 movable relative to the lower portion 62 between an aligned position thereof, in which the upper portion 64 is at least partially vertically aligned with the lower portion 62 above the lower portion 62, and a non-aligned position thereof (FIG. 8), in which the upper portion 64 is at least partially located beside the lower portion 62. Preferably, the upper portion 64 is movable between the aligned and non-aligned positions by pivoting about an axis of rotation "X" (FIG. 8). Each of the left and right arm assemblies 58, 60 preferably includes a hinge subassembly 80 configured for rotation of the upper portion 64 about the axis "X" defined by the hinge subassembly 80. As an example, in FIG. 8, the upper portion 64 of the right arm assembly 60 is shown in the non-aligned position thereof, and the upper portion 64 of the left arm assembly 58 is shown in the aligned position thereof.

Figure 7:
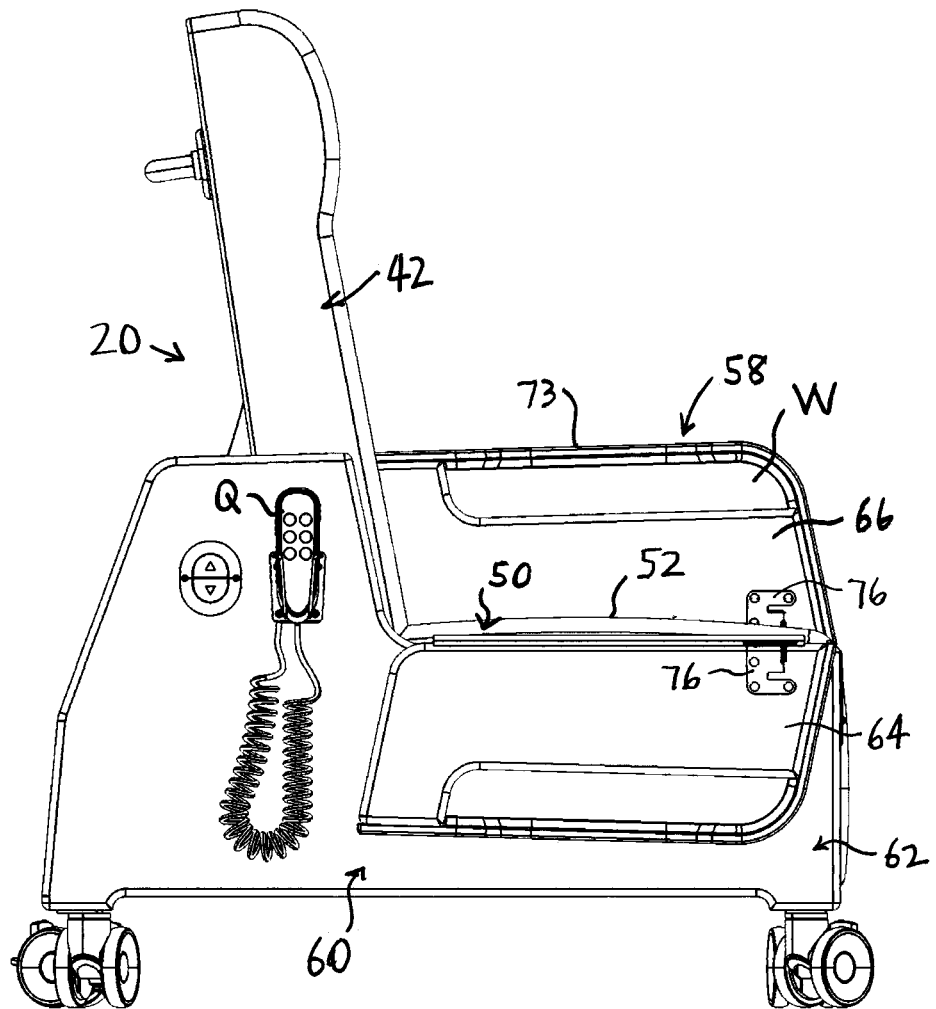
FIG. 7 is a right side view of the patient examination system of FIG. 1A, with an upper portion of a right arm assembly thereof in a non-aligned position and the frame assembly in the retracted condition, drawn at a smaller scale.

The advantage of the left and right arm assemblies 58, 60 including respective upper and lower portions is that this arrangement facilitates generally horizontal movement of the patient onto and from the patient examination system 20. Specifically, and as can be seen in FIGS. 7 and 8, when the seat subassembly 38 is in the lowered position thereof and the upper portion 64 is in the non-aligned position thereof, the patient is substantially horizontally movable over the lower portion 62.

For instance, the patient may be moved in the direction indicated by arrow "Y" in FIG. 8 onto the cover element 50 on the seat cushion 40. The patient may be moved in the direction indicated by arrow "Z" in FIG. 8, from the cover element 50 on the seat cushion 40. Such movement from the seat cushion 40 may be, for example, onto another support device (not shown).

As illustrated in FIG. 8, in one embodiment, the upper portion 64 preferably includes an upper portion body 66 having an upper portion mating surface 68 and the lower portion 62 preferably includes a lower portion body 70 having a lower portion mating surface 72 that is formed to mate with the upper portion mating surface 68 when the upper portion 64 is in the aligned position. Preferably, when the upper portion 64 is in the non-aligned position and the seat subassembly 38 is in the lowered position, the upper portion mating surface 68 and the lower portion mating surface 72 are laterally aligned with each other, and also aligned with at least part of the exposed surface 52 of the cover element 50. In one embodiment, the upper portions 64 may each include an armrest element 73 (FIG. 7) defining a gap "W" between the armrest element 73 and the upper portion body 66.

Figure 10:
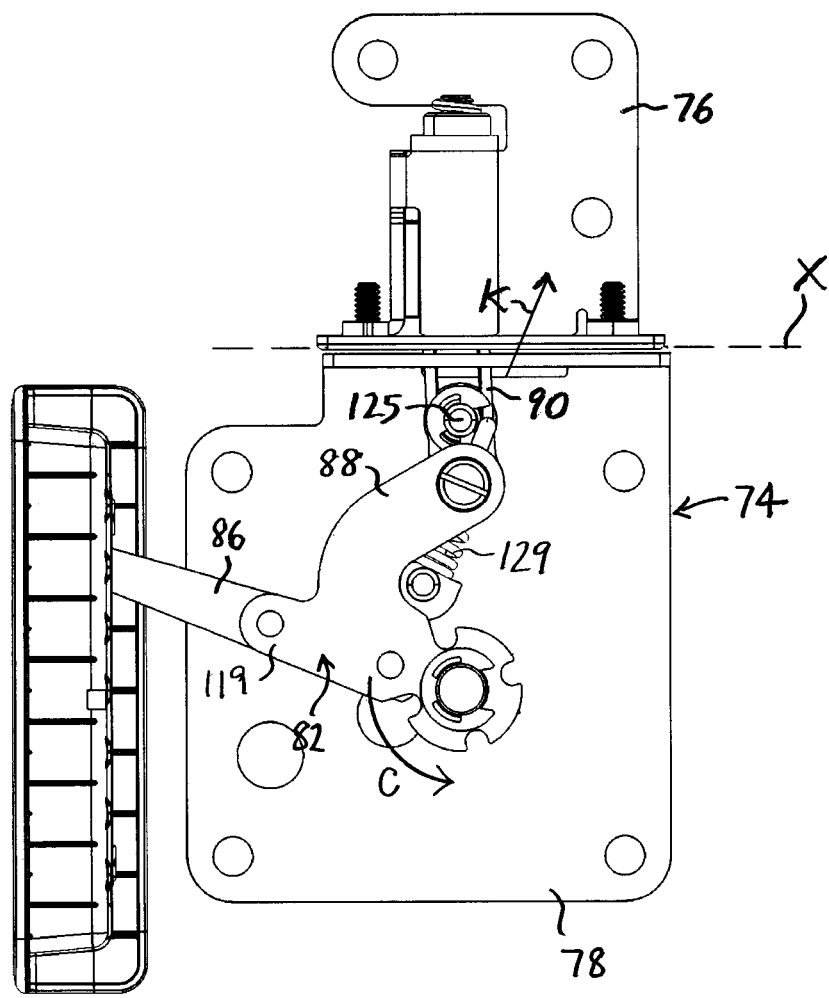
FIG. 10 is a side view of an embodiment of the latch assembly of the invention in a locked condition thereof, drawn at a larger scale.

Those skilled in the art would appreciate that, in practice, there may be situations where the only feasible movement onto the seat subassembly, or from the seat subassembly, would be substantially horizontal. In order to control movement of the upper portion, a latch assembly 74 preferably is located in each of the left and right arm assemblies 58, 60 (FIG. 10). It is preferred that the latch assembly 74 is movable between locked and unlocked conditions thereof, as will be described. Preferably, the latch assembly 74 is configured to secure the upper portion 64 in the aligned position when the latch assembly 74 is in the locked condition, and the latch assembly 74 is also configured to permit the upper portion 64 to move to the non-aligned position when the latch assembly 74 is in the unlocked condition.

The latch assembly 74 that is mounted in the upper and lower portion bodies 66, 70 of the right arm assembly 60 is illustrated in FIGS. 10-18. It will be understood that the latch assembly 74 that is mounted in the left arm assembly 58 is the mirror image thereof.

In one embodiment, the latch assembly 74 preferably includes an upper plate 76 secured to the upper portion body 66, and a lower plate 78 secured to the lower portion body 70. It is also preferred that the upper plate 76 and the lower plate 78 define the axis of rotation "X" therebetween.

The latch plates 76 that are mounted to the upper portions 64 of each of the left and right arm assemblies can be seen, for example, in FIG. 7.

Those skilled in the art would appreciate that, in one embodiment, the axis of rotation "X" preferably is also defined by the hinge subassembly 80 that is at least partially located between the upper and the lower plates 76, 78. The hinge subassembly 80 is omitted from FIGS. 10-18 for clarity of illustration. It will be understood that the hinge subassembly 80 may be in any suitable form. Those skilled in the art would be aware of suitable forms of hinge subassemblies.

Figure 11:
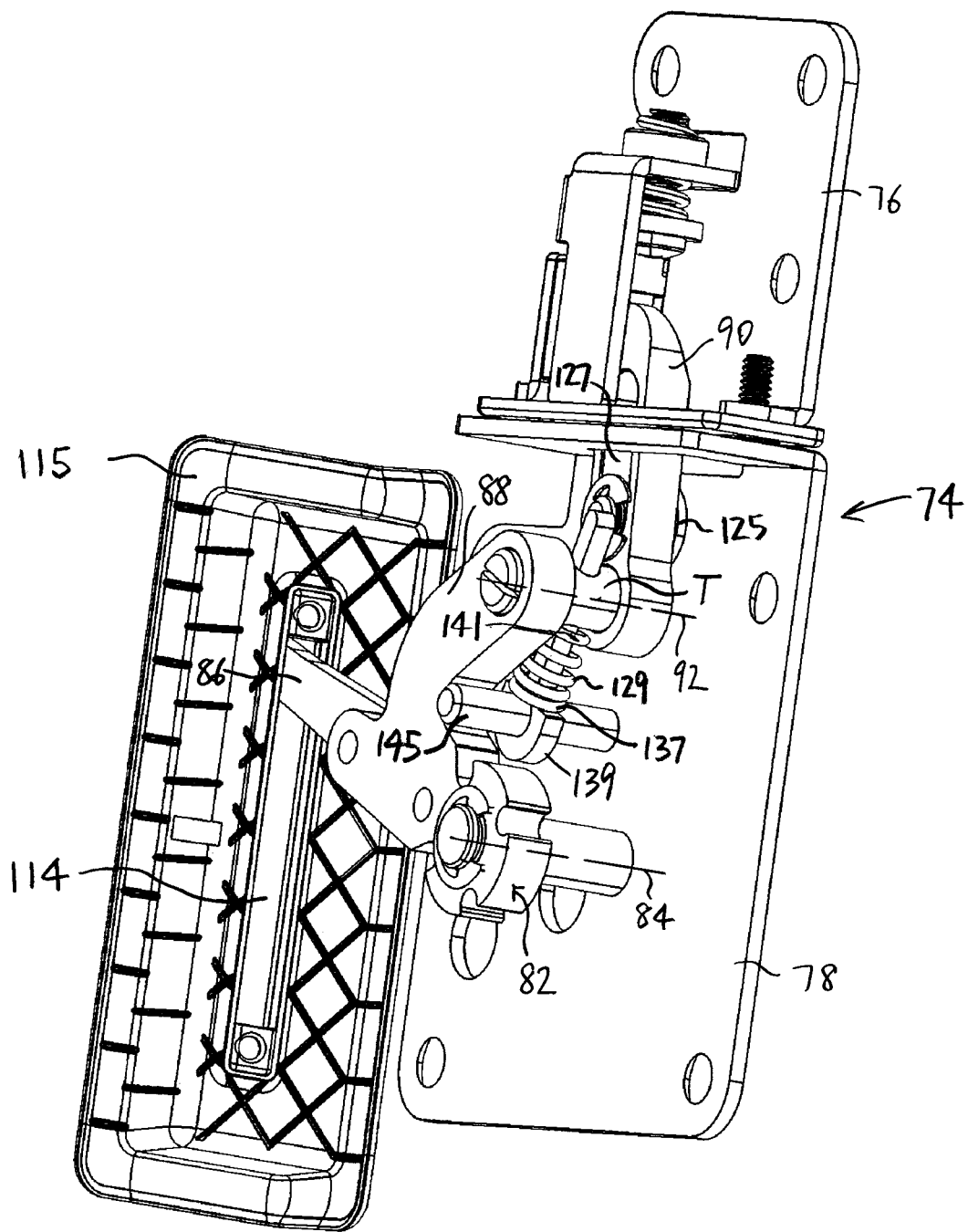
FIG. 11 is an isometric view of the latch assembly of FIG. 10, drawn at a larger scale.

In one embodiment, the latch assembly 74 preferably includes an activation element 82 mounted to the lower plate 78 and rotatable about an activation element axis 84 (FIG. 11). As can be seen in FIG. 10, the activation element 82 preferably includes a first arm 86 and a second arm 88. Preferably, the latch assembly 74 also includes a latch element 90 pivotally mounted to the second arm 88 and pivotable about a latch element axis 92 that is parallel to the activation element axis 84 (FIG. 11). The activation element 82 preferably is movable between a first position (FIG. 10), in which the latch assembly 74 is in the locked condition and the first arm 86 is positioned pointing at least partially upwardly, and a second position (FIG. 12), in which the latch assembly 74 is in the unlocked condition and the first arm 86 is positioned pointing at least partially downwardly. As will be described, movement of the activation element 82 from the first position to the second position thereof causes the latch assembly 74 to move from the locked condition to the unlocked condition thereof.

The direction of rotation of the activation element 82 from the first position to the second position is indicated by arrow "C" in FIG. 10.

When the upper portion 64 is in the aligned position (i.e., aligned vertically with the lower portion 62), movement of the activation element 82 from the second position thereof to the first position thereof moves the latch assembly 74 from its unlocked condition to its locked condition. The direction of rotation of the activation element 82 from the second position to the first position is indicated by arrow "D" in FIG. 12.

Figure 15:
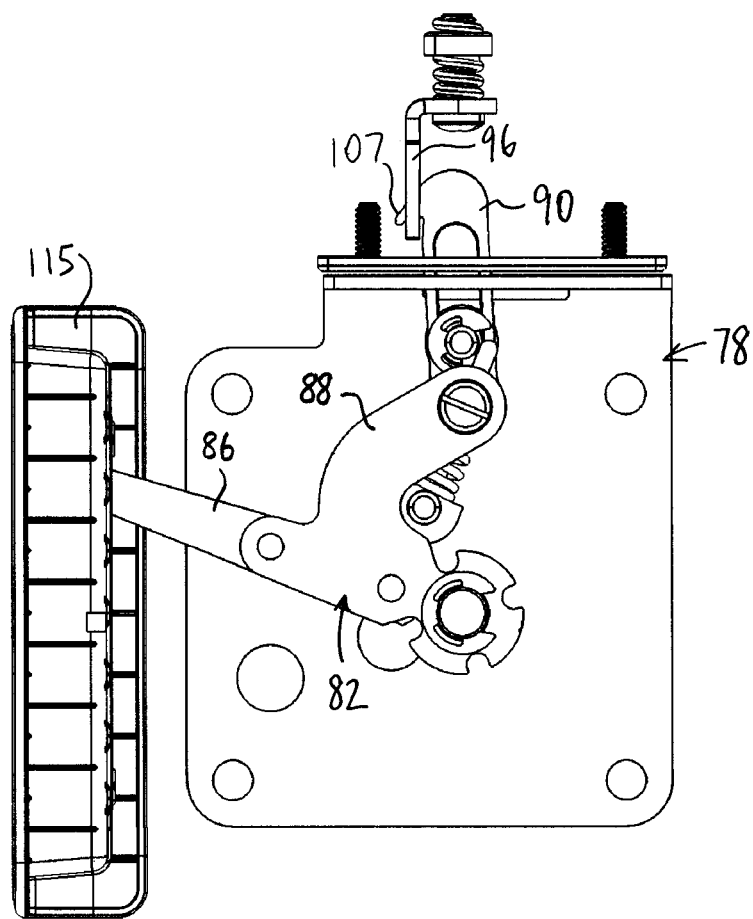
FIG. 15 is a side view of the latch assembly of FIG. 10 in a locked condition, with certain elements omitted.

The latch assembly 74 is shown in its locked condition in FIGS. 10, 11, and 15. When the latch element 90 is in a locked position thereof, the latch assembly 74 is in its locked condition. From the foregoing, it can be seen that, when the latch assembly 74 is in the locked condition thereof, the upper portion 64 is locked in the aligned position thereof relative to the lower portion 62. For example, in FIGS. 7 and 8, the upper portion 64 of the left arm assembly 58 is locked in the aligned position thereof relative to the lower portion 62 of the left arm assembly 58. For illustrative purposes, in FIGS. 7 and 8, the latch assembly 74 of the right arm assembly 60 is in the unlocked condition, which permits the upper portion 64 of the right arm assembly 60 to be in the non-aligned position relative to the lower portion 62 of the right arm assembly 60.

It will be understood that certain elements are omitted from FIG. 15 in order to show the location of the latch element 90 in relation to the upper plate 76, when the latch element 90 is in its locked position.

Similarly, the latch assembly 74 is shown in its unlocked condition in FIGS. 12, 13, 14, and 17. When the latch element 90 is in an unlocked position thereof, the latch assembly 74 is in its unlocked condition. It will also be understood that certain elements are omitted from FIGS. 13 and 17 in order to show the location of the latch element 90 in relation to the upper and lower plates 76, 78, when the latch element 90 is in its unlocked position.

Figure 12:
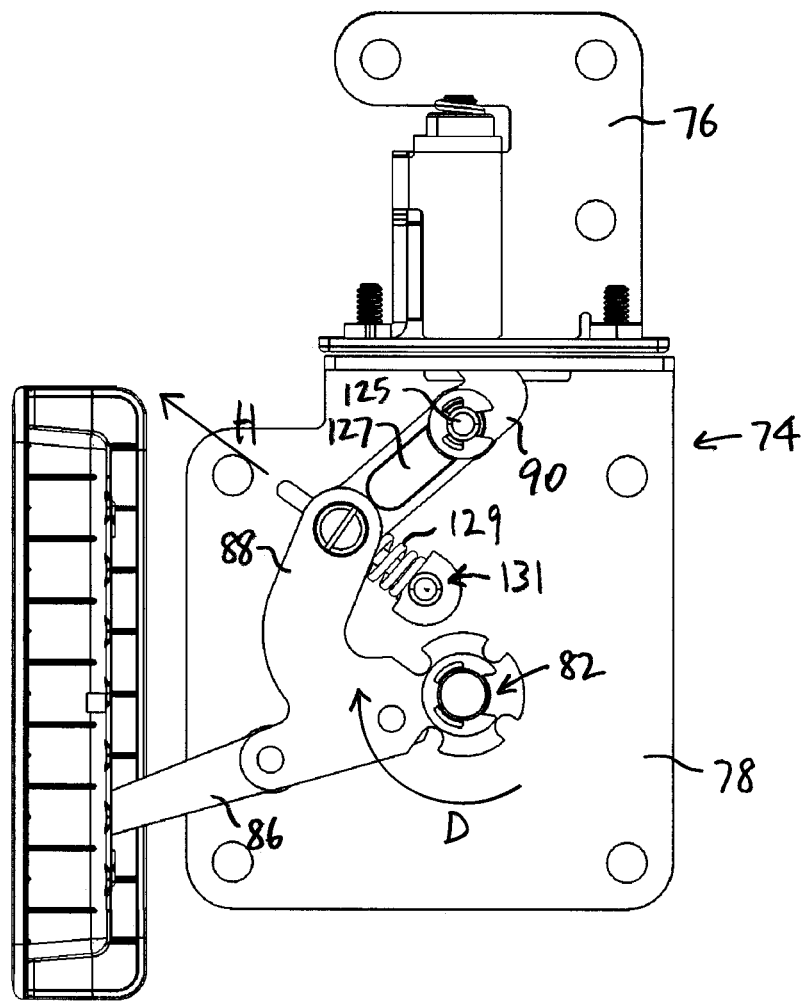
FIG. 12 is a side view of the latch assembly of FIG. 10 in an unlocked condition thereof, drawn at a smaller scale.

As can be seen, e.g., in FIGS. 10 and 12, the latch element 90 preferably is moved from the locked position thereof (FIG. 10) to the unlocked position thereof (FIG. 12) by rotation of the activation element 82 from the first position to the second position thereof respectively. The latch element 90 preferably is moved from the unlocked position thereof to the locked position thereof by rotation of the activation element 82 from the second position to the first position thereof.

Figure 18:
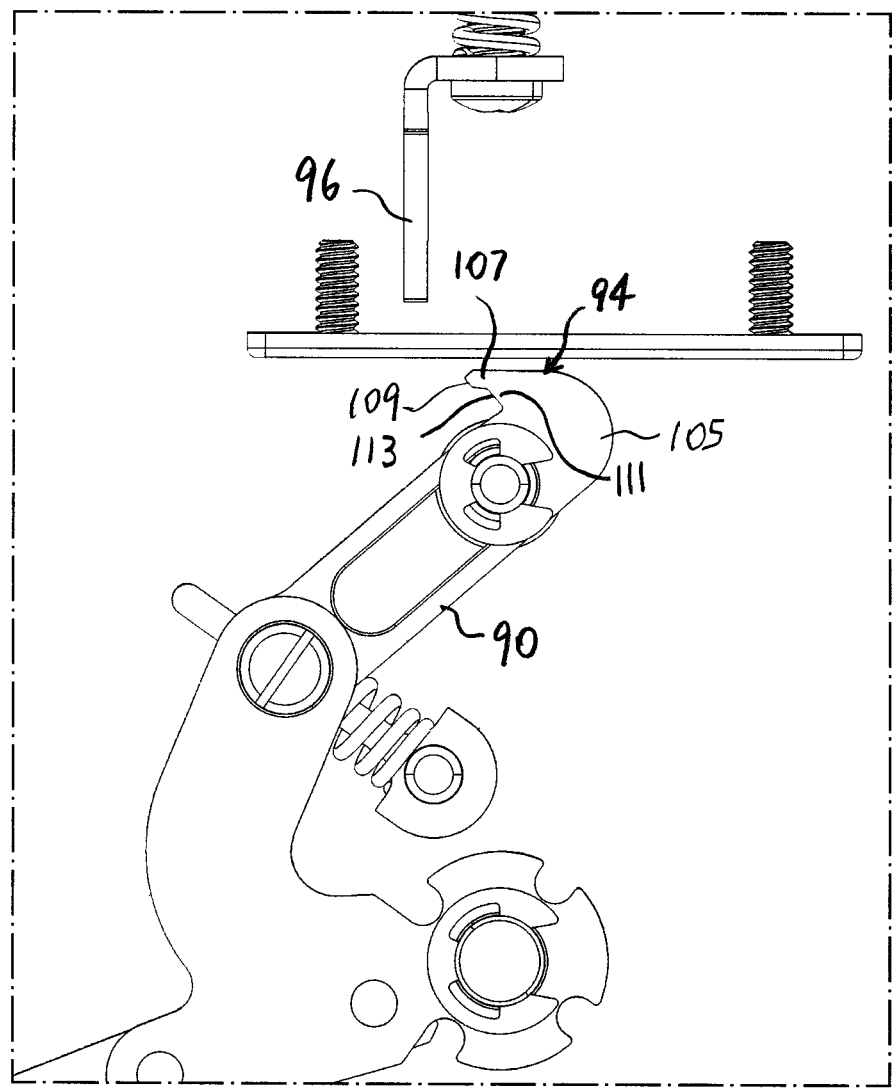
FIG. 18 is a side view of a portion of the latch assembly of FIG. 17, drawn at a larger scale.

As can be seen in FIG. 18, the latch element 90 preferably includes a hook portion 94 that engages with a stop 96 mounted to the upper plate 76, when the activation element 82 is in the first position thereof, and when the upper portion 64 is in the aligned position thereof. It will be understood that the upper plate 76 is omitted from FIGS. 15-18 for clarity of illustration. (As noted above, when the activation element 82 is in the first position thereof, the latch element 90 is in the locked position thereof.) Those skilled in the art would appreciate that the stop 96 may have any suitable configuration. As can be seen in FIGS. 16C and 16D, in one embodiment, the stop 96 preferably comprises a stop frame 98 that includes a lower ledge 101 with which the hook portion 94 is engageable. Preferably, the lower ledge 101 partially defines an opening 103 in the stop frame 98.

In one embodiment, the hook portion 94 preferably includes a hook body 105 and a point region 107 extending from the body 105, to define a protruding region 109 that is protruding or proud relative to a recessed region 111, that extends from the point region 107 toward the body 105. The recessed region 111 is partly defined by an edge 113. It will be understood that, when the hook portion 94 engages the lower ledge 101, the edge 113 engages the lower ledge 101, and the protruding region 109 tends to hold the hook portion 94 engaged with the stop 96. Preferably, when the edge 113 engages the lower ledge 101, the point region 107 at least partially extends into the opening 103 (FIG. 15)

Those skilled in the art would appreciate that the hook portion 94 and the lower ledge 101 are configured and positioned relative to each other so that, when the latch element 90 is in its locked position, the hook portion 94 is unlikely to be inadvertently removed from engagement with the lower ledge 101, e.g., if the upper portion 64 is jarred by an object striking it.

As can be seen in FIGS. 10, 11, and 15, when the activation element 82 is in the first position thereof, the first arm 86 preferably is in an uppermost position thereof. Also, and as can be seen in FIGS. 12, 13, 14, and 17, when the activation element 82 is in the second position thereof, the first arm 86 preferably is in a lowermost position thereof. In addition, however, the first arm 86 preferably is positionable at a first arm intermediate position, between the uppermost and lowermost positions thereof, as can be seen in FIGS. 16A-16D. When the first arm is in the first arm intermediate position, the latch element 90 is located by the activation element 82 in an intermediate position thereof in which the hook portion 94 is disengaged from the stop 96, and positioned above the lower portion 62.

Figure 16A:
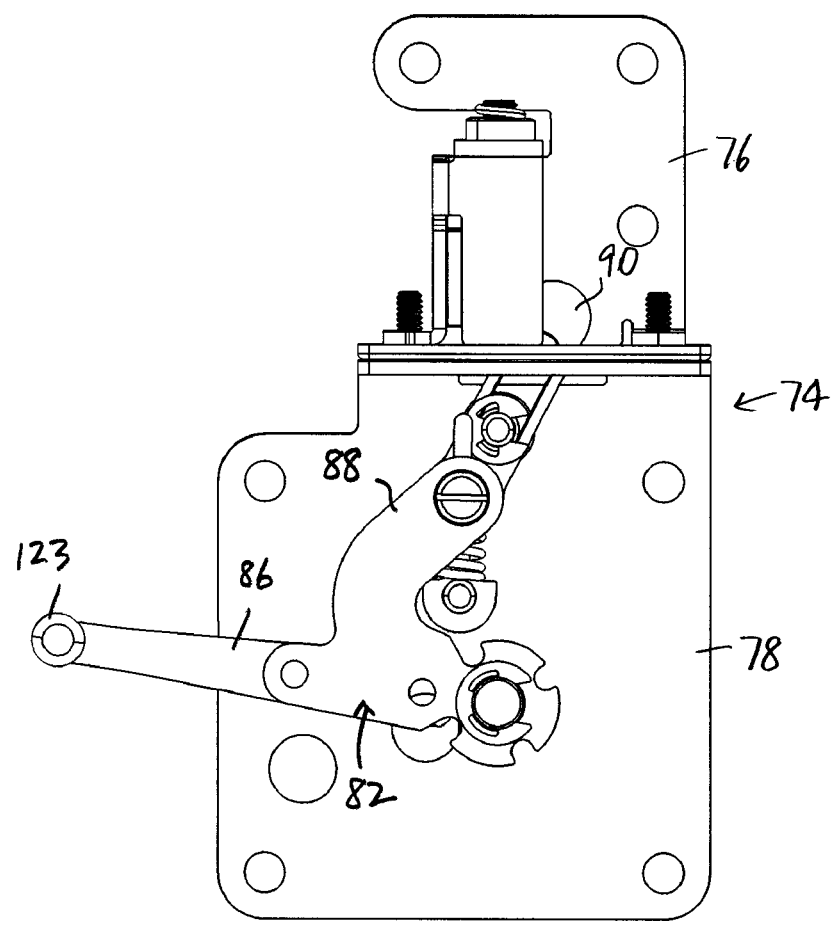
FIG. 16A is a side view of the latch assembly of FIGS. 10-15 in an intermediate condition.
Figure 16B:
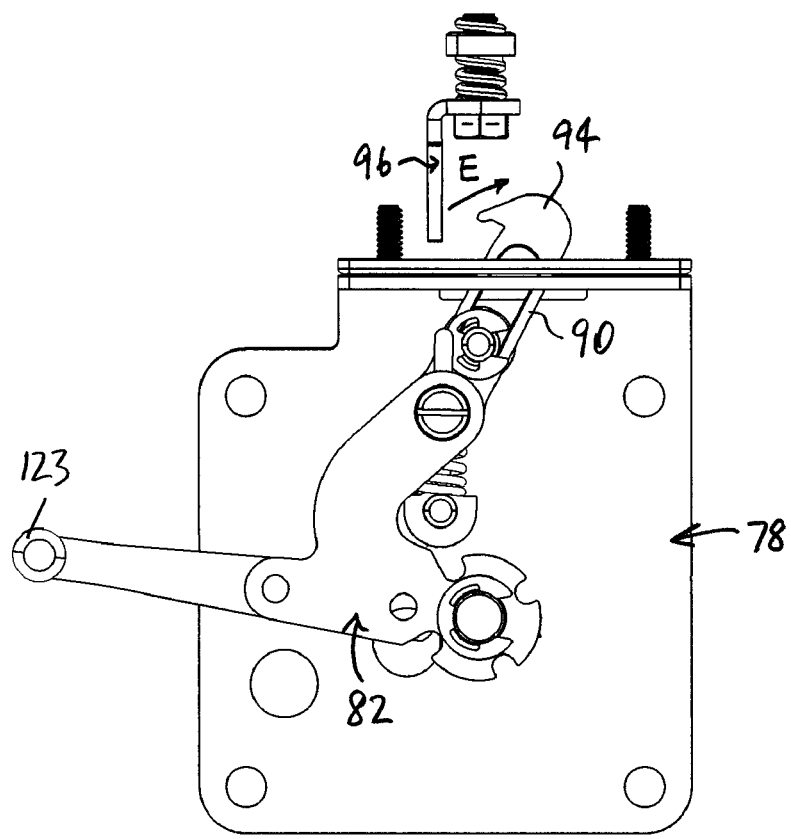
FIG. 16B is a side view of the latch assembly of FIG. 16A with certain elements omitted.
Figure 16C:
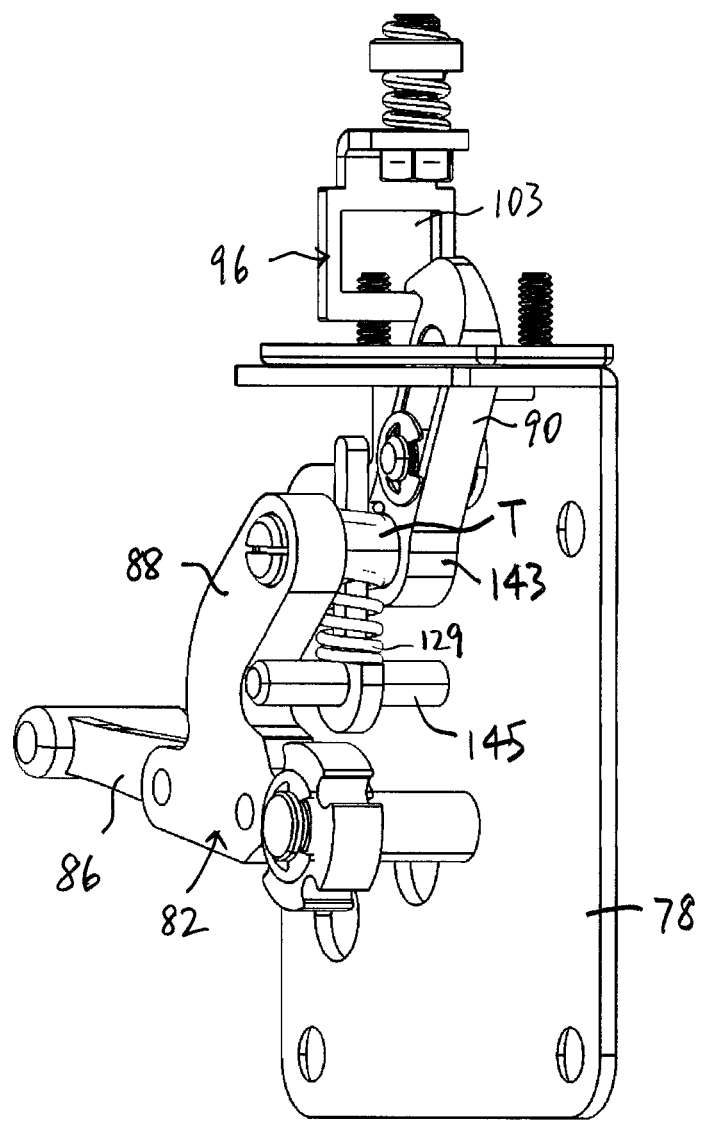
FIG. 16C is an isometric view of the latch assembly of FIG. 16B.
Figure 16D:
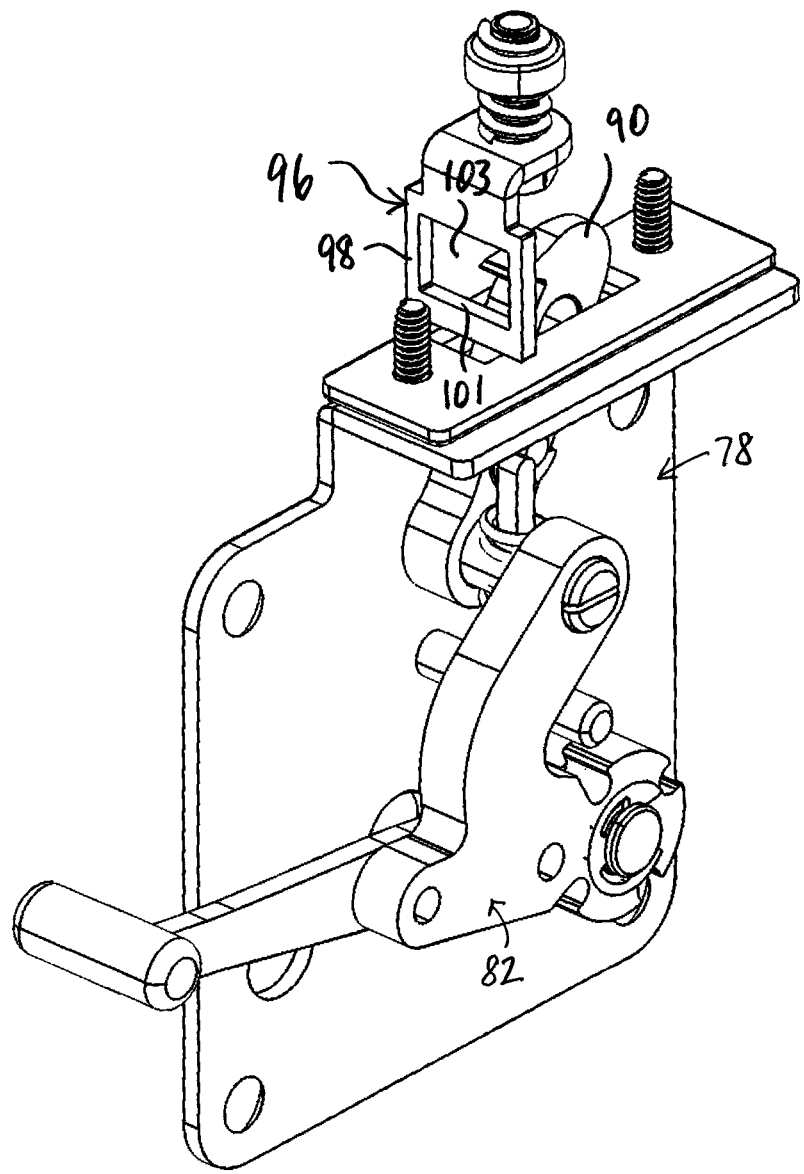
FIG. 16D is another isometric view of the latch assembly of FIGS. 16B and 16C.
Figure 17:
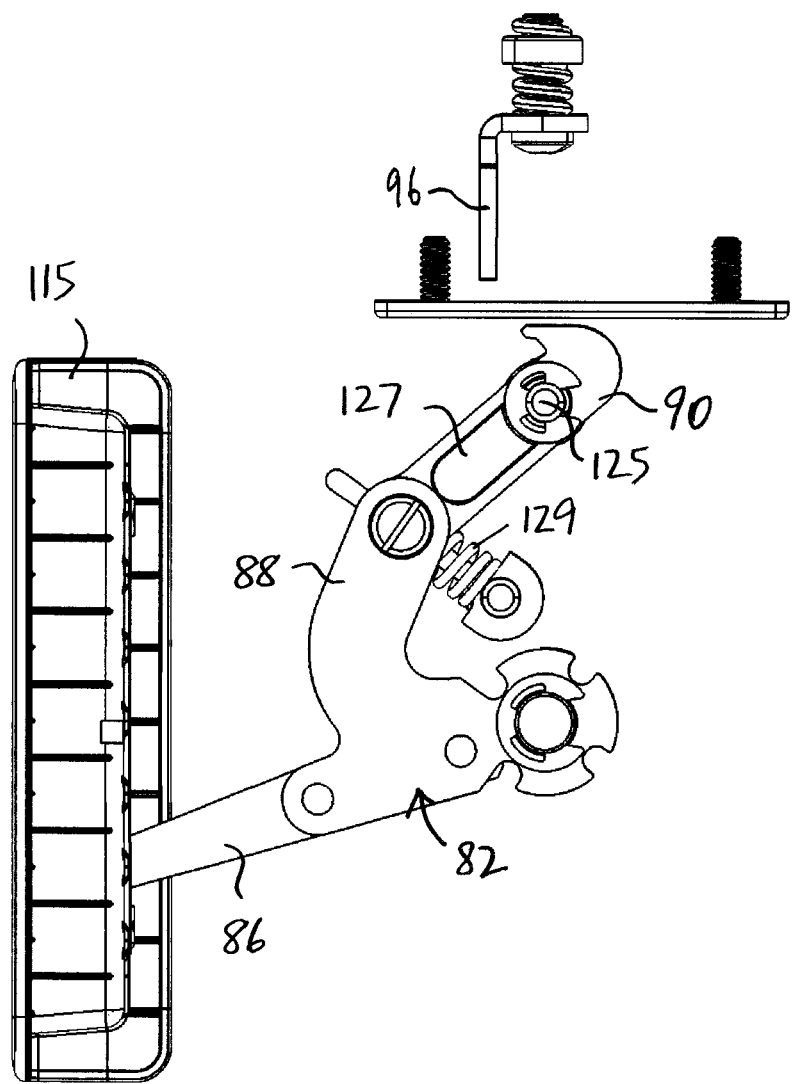
FIG. 17 is a side view of the latch assembly in the unlocked condition thereof, with certain elements omitted.

As can be seen in FIGS. 15 and 16B, in which the latch element 90 is shown in the locked position and the intermediate position thereof respectively, when the latch element 90 is moved from the locked position to the intermediate position, the hook portion 94 is pivoted slightly upwardly, as indicated by arrow "E" in FIG. 16B. This upward pivoting movement is needed for disengagement so that the protruding region 109 can clear the lower ledge 101, thereby disengaging the edge 113 from the lower ledge 101.

It will be understood that the upper plate 76 is omitted from FIGS. 16A-16D for clarity of illustration. It can be seen, e.g., in FIG. 16B that when the activation element 82 is in the intermediate position thereof, the hook portion 94 of the latch element 90 is located in the upper portion 64, even though the hook portion 94 is disengaged from the stop 96 at that point.

Those skilled in the art would appreciate that, because the lower plate 78 and the upper plate 76 preferably are mounted inside the lower portion body 70 and the upper portion body 66 respectively, it is preferred that the lower portion body 70 includes an opening 114 through which the first arm 86 partially protrudes, so that the operator may have access to the first arm 86, to move the first arm 86 as needed.

Figure 14:
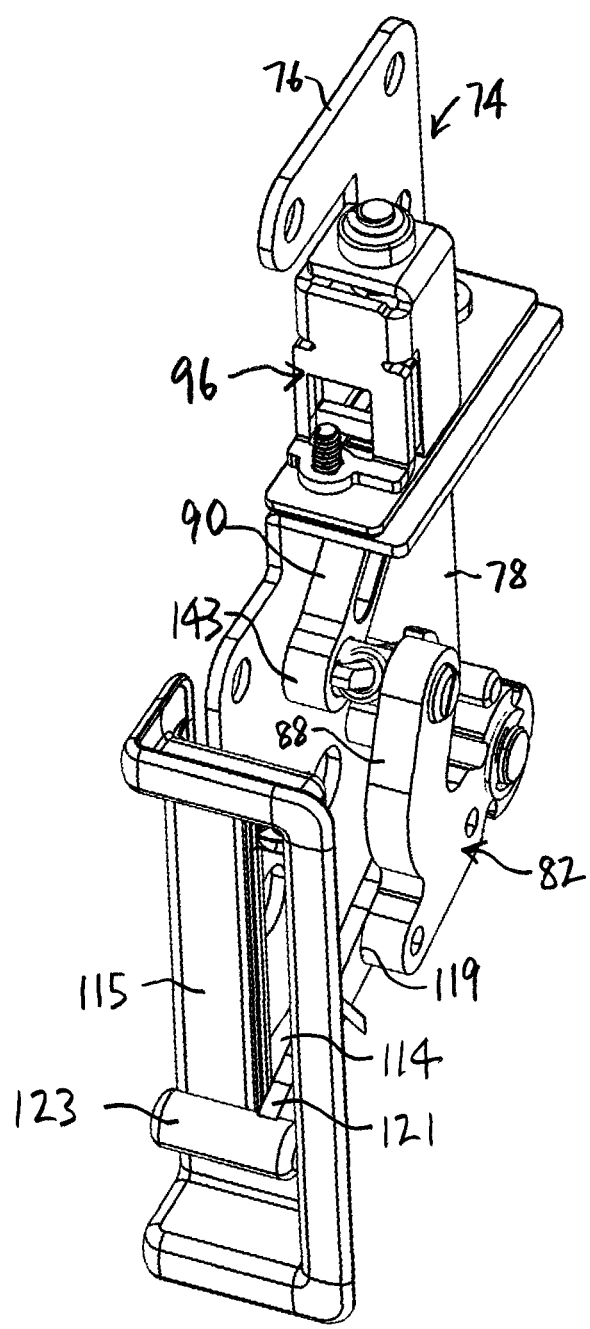
FIG. 14 is an isometric view of the latch assembly of FIG. 12.

As can be seen in FIGS. 11 and 14, in one embodiment, it is preferred that the lower portion body 70 includes a front exterior surface element 115 in which the opening 114 is formed. Preferably, the first arm 86 extends between an inner end 119 (FIG. 10) at which the first arm 86 is connected to the second arm 88, and an outer end 121 (FIG. 14) that is distal to the second arm 88. It is also preferred that the outer end 121 extends from the lower portion body 70 through the opening 114 to expose a terminal portion 123 of the outer end 121 (FIG. 14). As can also be seen in FIG. 14, in one embodiment, the terminal portion 123 preferably includes a knob or similar element, to enable the operator to easily grasp the terminal portion 123.

Figure 13:
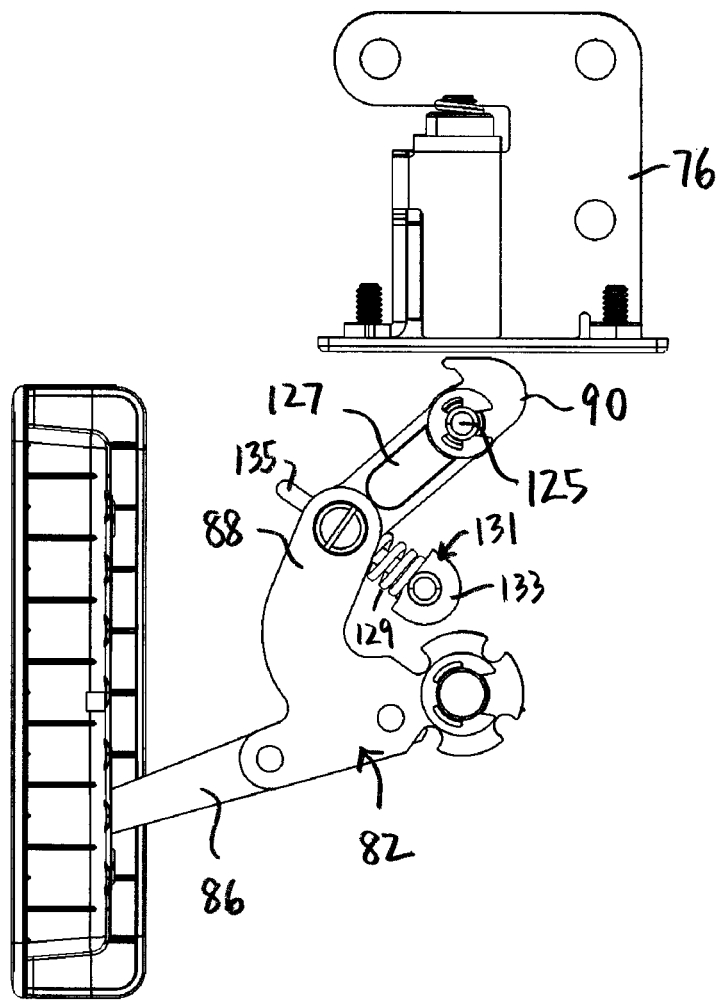
FIG. 13 is a side view of the latch assembly of FIG. 12, with a lower plate omitted.

In one embodiment, the latch assembly 74 preferably also includes a key element 125 connected to the lower plate 78 (FIG. 11) and slidably engaged in a slot 127 in the latch element 90, for guiding the latch element 90 along a predetermined path as the latch element 90 is moved between the locked and unlocked positions thereof (FIGS. 10, 13).

Preferably, the latch assembly 74 additionally includes a resilient element 129 (FIG. 11) for biasing the latch element 90 to the locked position thereof when the activation element 82 is in the first position, and also for biasing the latch element 90 to the unlocked position thereof when the activation element 82 is in the second position thereof.

Those skilled in the art would appreciate that this is achieved by utilizing an over-center linkage arrangement. Preferably, the resilient element 129 is a helical compression spring (FIGS. 11, 13, 16C). It is also preferred that the latch assembly 74 includes a biasing pin element 131 extending between inner and outer ends 133, 135 thereof (FIG. 13).

The biasing pin element 131 preferably is rotatably mounted to the lower plate 78 at its inner end 133, and rotatably mounted at its outer end 135, via a rod "T" (FIG. 11), to the second arm 88 of the activation element 82. Preferably, the rod "T" defines the latch element axis 92. As can be seen in FIG. 11, the helical compression spring 129 preferably is positioned on the biasing pin element 131 for engaging a first end 137 of the helical compression spring 129 with a pin element body 139 located at the inner end 133 of the biasing pin element, and for engaging a second end 141 of the helical compression spring 129 with the rod "T" (FIG. 11), and thereby indirectly with the second arm 88 of the activation element 82. As a result, the helical compression spring 129 urges the second arm 88 in a first direction (indicated by arrow "K" in FIG. 10) to hold the latch element 90 in the locked position thereof when the activation element 82 is in the first position thereof, and the helical compression spring 129 urges the second arm 88 in a second direction (indicated by arrow "H" in FIG. 12) that radially diverges from the first direction, to hold the latch element 90 in the unlocked position thereof when the activation element 82 is in the second position thereof.

Those skilled in the art would appreciate that, when the first arm 86 is in the first arm intermediate position, the latch assembly 74 is not biased to its locked condition, or to its unlocked condition. Because the spring 129 is relatively less compressed between the rod "T" and the pin element body 139 when the activation element 82 is in the intermediate position thereof, the activation element 82 can relatively easily be moved therefrom to its first or second positions.

As can be seen in FIGS. 11 and 16C, the rod "T" preferably is positioned substantially orthogonally to the second arm 88, and also to the lower plate 78. It is also preferred that the rod "T" is pivotably mounted to a lower end 143 of the latch element 90 (FIG. 14), so that movement of the second arm 88 causes corresponding movement of the lower end 143 of the latch element 90. The biasing pin element 131 is pivotably mounted to a pivot pin 145 that is mounted to the lower plate 78 (FIGS. 11, 16C).

As can be seen, e.g., in FIG. 2A, in one embodiment, the footrest subassembly 46 preferably includes an auxiliary footrest cushion 147, supported by an auxiliary footrest linkage 149. The auxiliary footrest linkage is connected to the footrest linkage subassembly 56.

From the foregoing, it can be seen that the patient examination system 20 meets a number of the guidelines provided pursuant to the ADA.

Some of the guidelines provided pursuant to the ADA are discussed below.

A. Back Recline: The system 20 provides a motorized recline with infinite stops to full flat (horizontal) position, with the patient's head and back supported through the entire range of incline, as recommended pursuant to the ADA.

B. Ottoman: As noted above, the system 20 preferably includes a motorized ottoman (i.e., the footrest subassembly 46) with infinite stops to full flat (horizontal) position.

C. Sleep Position: The patient examination system 20 provides a fully flat sleep surface "S" at a relatively low height above the floor "F" (FIG. 3B). For example, in one embodiment, the sleep surface "S" may be at a minimum 19" height, adjustable higher by motorized lift. The minimum distance 151 of the sleep surface "S" above the floor "F" (FIG. 3B) preferably is not more than 19". For the purposes hereof, it is understood that the sleep surface "S" includes the exposed surface 52 of the cover element 50 and an outer surface "J" (FIGS. 3B, 5C) of the back cushion 44.

D. Exam Position: The patient examination system 20 provides a motorized lift with up to 400 lb. capacity, with infinite stops to full flat (horizontal) exam position to a maximum of 32" in height. The distance 153 of the sleep surface "S" above the floor "F" (FIG. 5C) preferably is up to 32".

E. Seated Transfer Height: In the system 20, this is a 19" minimum above the floor F. Seated Transfer Surface: Preferably, the seated transfer surface is a minimum of 30" wide×21.5" deep.

G. Transfer Arms: As noted above, the upper portions 64 of the left and right arm assemblies 58, 60 are hinged to permit unobstructed transfer.

H. Armrests: These serve as transfer support and rail within reach of transfer surface and respectively resist vertical and horizontal forces of 250 lbs.

I. Base: As can be seen in FIG. 3B, the system 20 provides for a clearance distance "P" above the support surface "F" that is relatively large. Preferably, the clearance distance "P" is a minimum of 6". This enables a portable patient lift to be accommodated.

J. Stirrups: The system 20 includes optional removable stirrups 155 (FIG. 6), to provide a method for supporting, positioning and securing the patient's legs.

K. Stirrup Storage: The system 20 includes built-in stirrup storage at the rear of unit.

L. Continuous Footrest: A cushioned footrest (i.e., the footrest subassembly, and the seat subassembly) includes the cover element 50 having a single surface from the back of the seat to the bottom of the footrest cushion 48.

M. Controller: The controller "Q" may include a pendant control accessible by the patient and the operator, and also a separate lift button for controlling vertical movement.

N. Power Connection Device: The system 20 may include a power connection device, which may include a USB port.

O. Optional Steel Legs or Independently Locking Casters: As illustrated, the legs include casters. It will be understood that the legs may, optionally, not include casters.

P. Optional Push Bar: As can be seen in FIG. 1A, the system 20 may include a push bar 157 positioned on the back subassembly 42.

Q. Armrests: The armrests 73 of the left and right arm assemblies 58, 60 may be upholstered, urethane, or have solid surfaces.

Another embodiment of the patient examination system 220 of the invention is illustrated in FIGS. 19A-27B. As can be seen in FIGS. 19A-22B, the patient examination system 220 preferably includes a frame assembly 222 (FIG. 20B) supporting a patient support assembly 236. The frame assembly 222 extends between front and back ends 200F, 200B thereof.

Figure 19A:
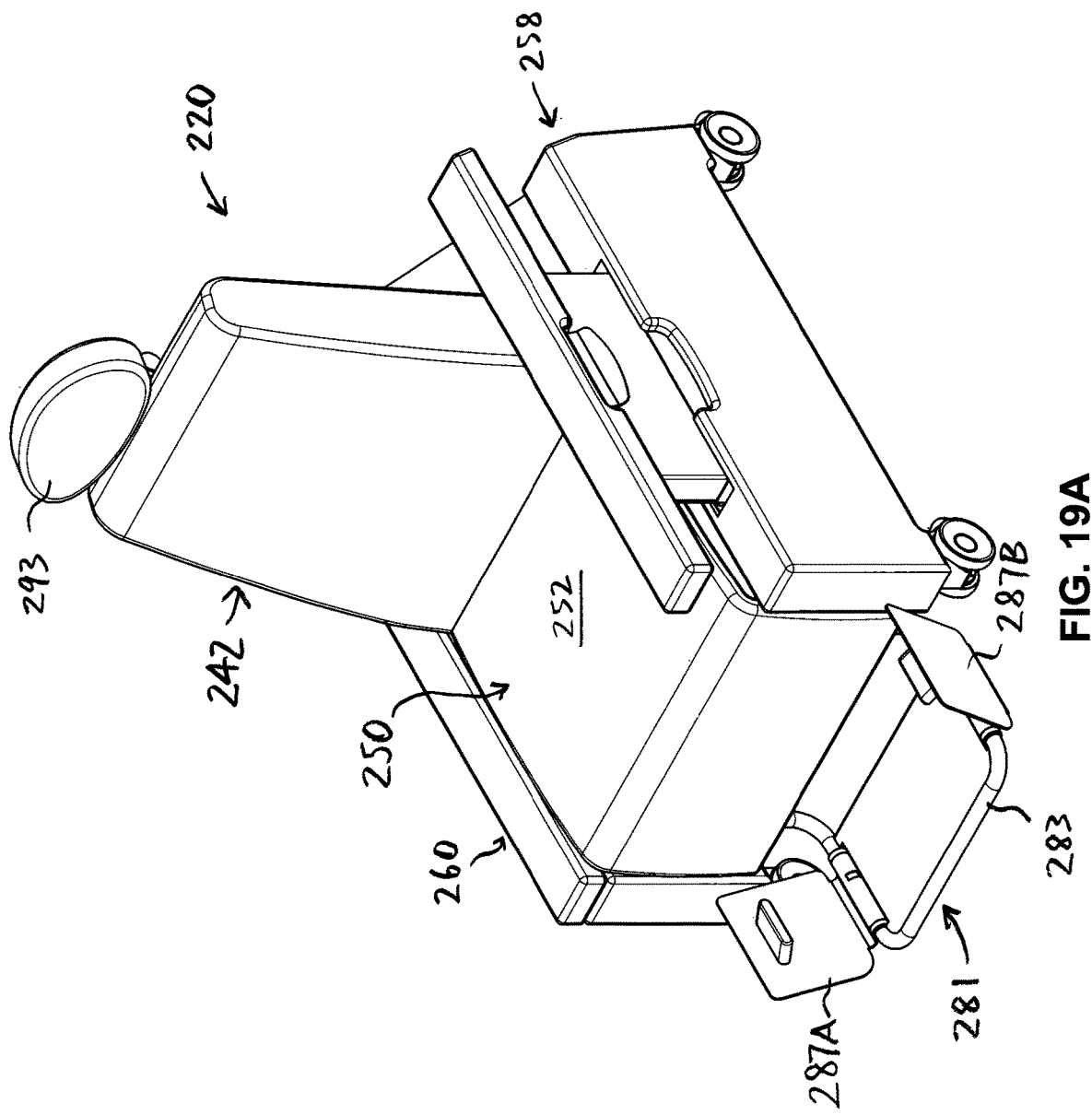
FIG. 19A is an isometric view of another embodiment of the patient examination system of the invention including a back subassembly and a foot support assembly, drawn at a smaller scale.
Figure 19B:
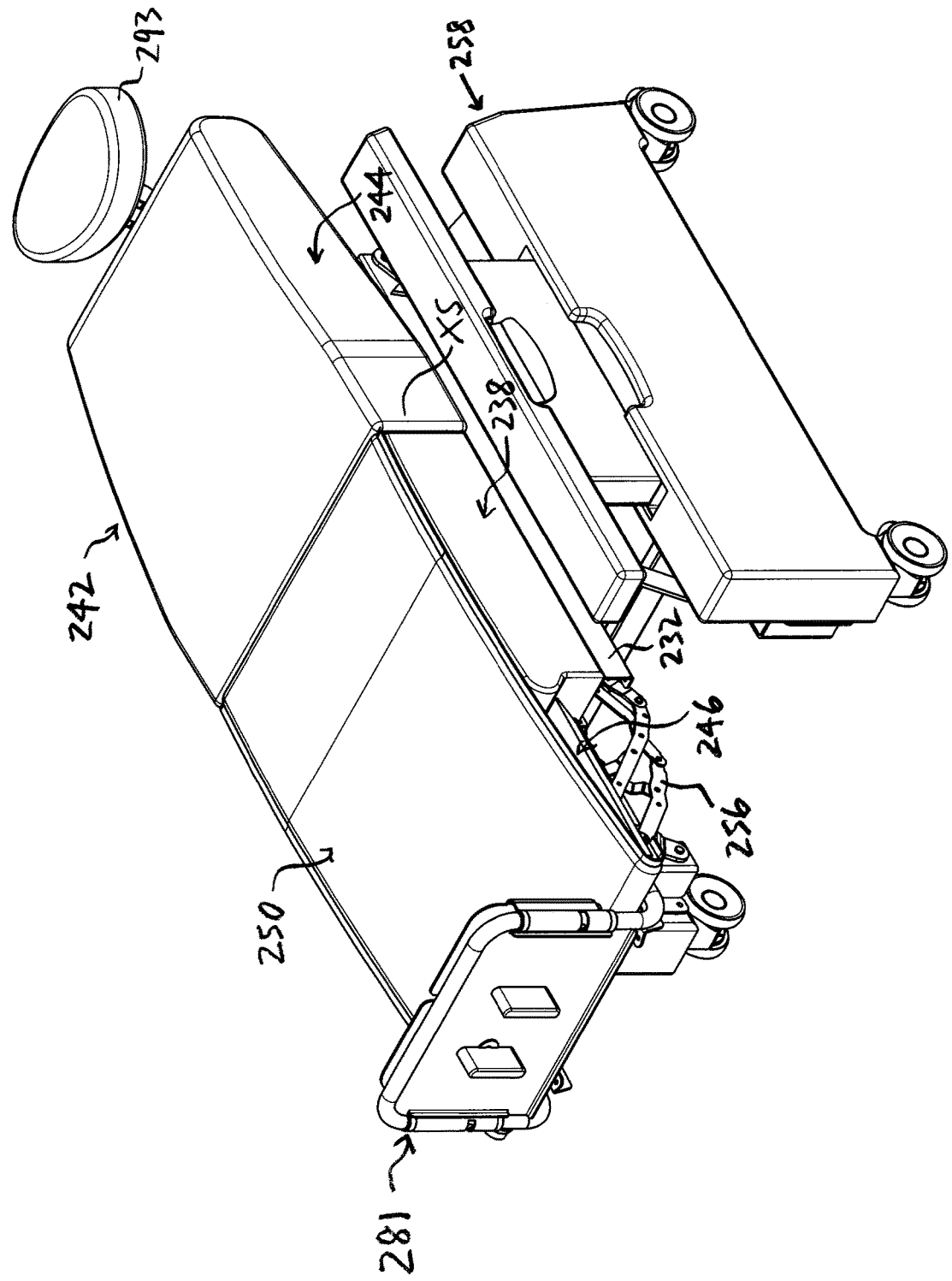
FIG. 19B is an isometric view of the patient examination system of FIG. 19A in which the frame is in the extended condition and the back subassembly is in the horizontal position.
Figure 21A:
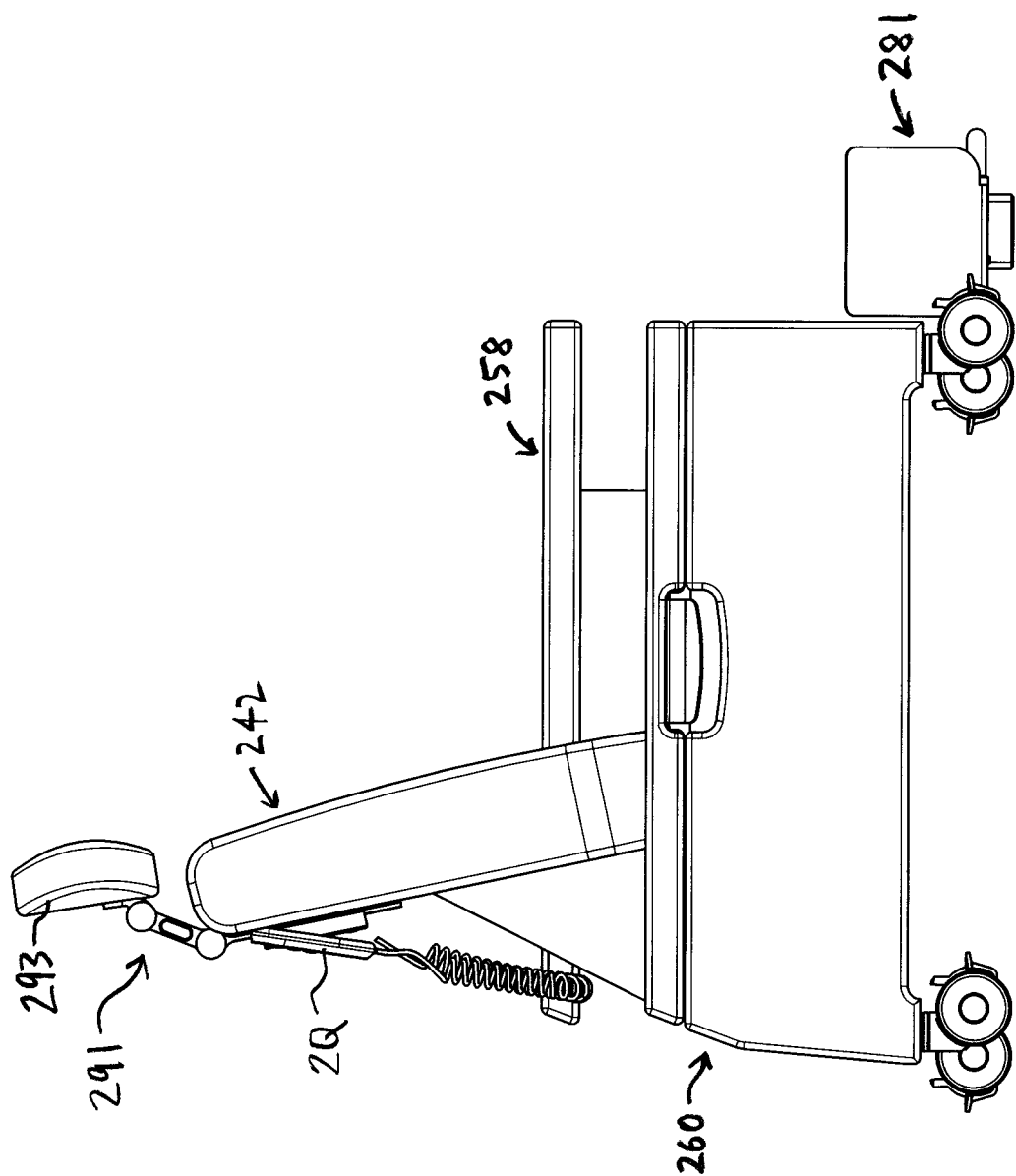
FIG. 21A is a right side view of the patient examination system of FIGS. 19A and 19B, drawn at a smaller scale.
Figure 21B:
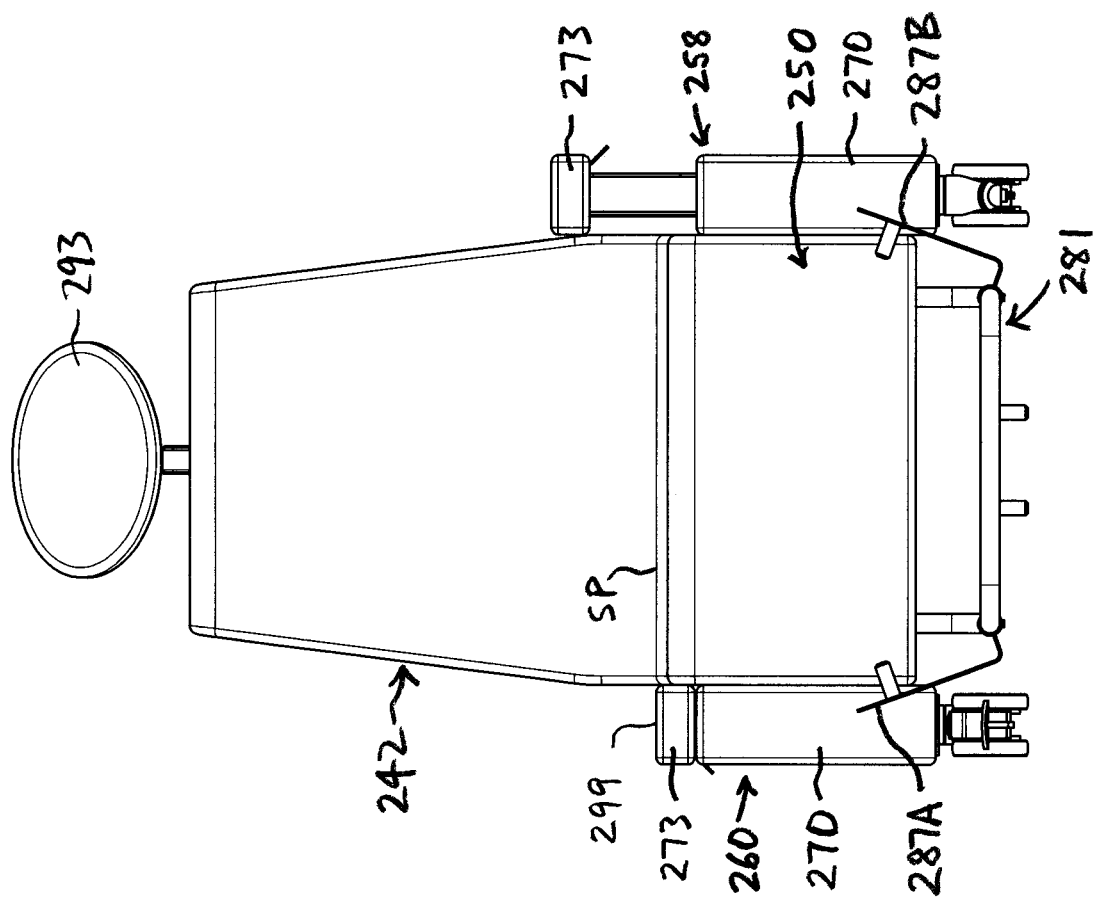
FIG. 21B is a front side view of the patient examination system of FIG. 21A.
Figure 21C:
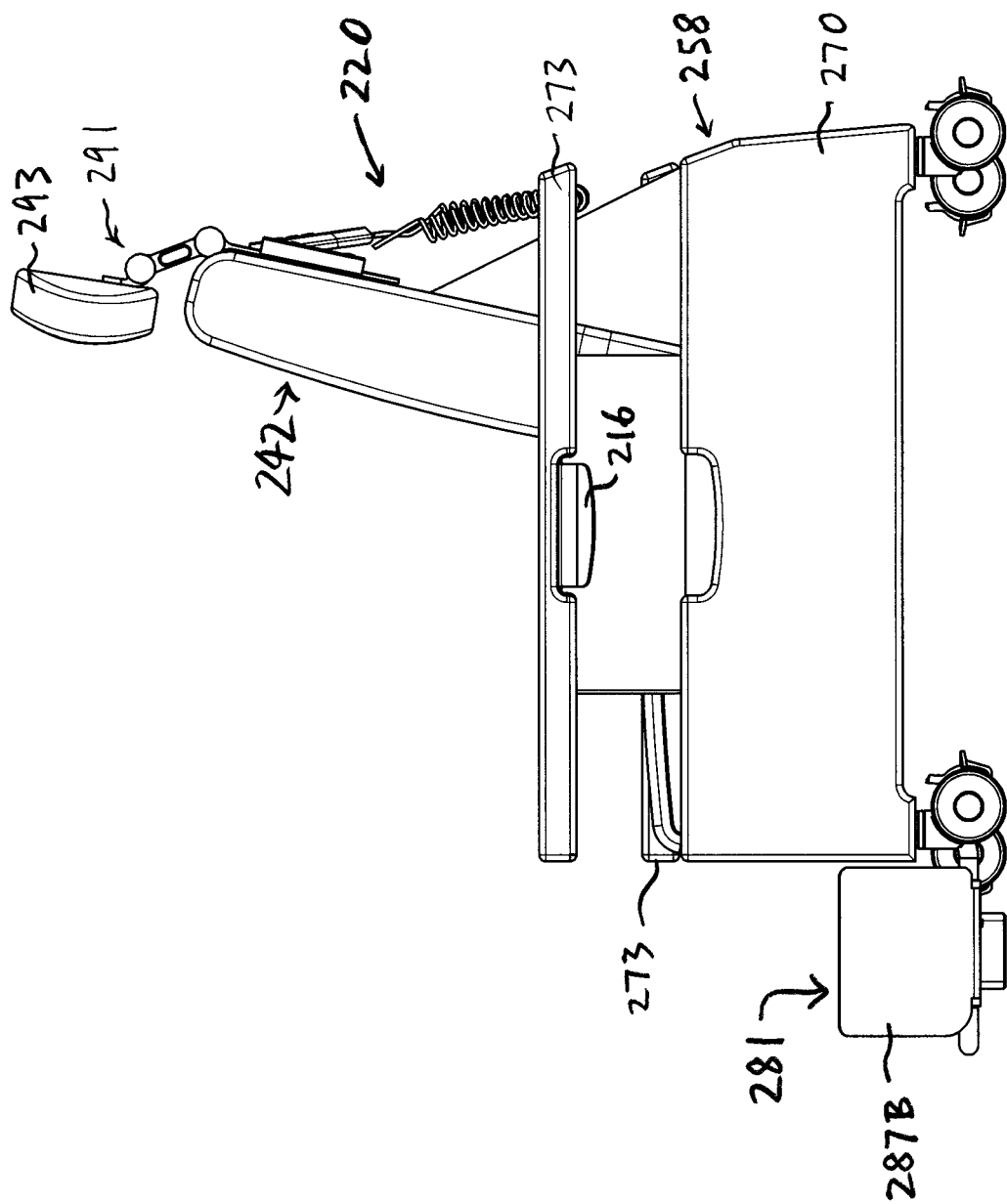
FIG. 21C is a left side view of the patient examination system of FIGS. 21A and 21B.
Figure 21D:
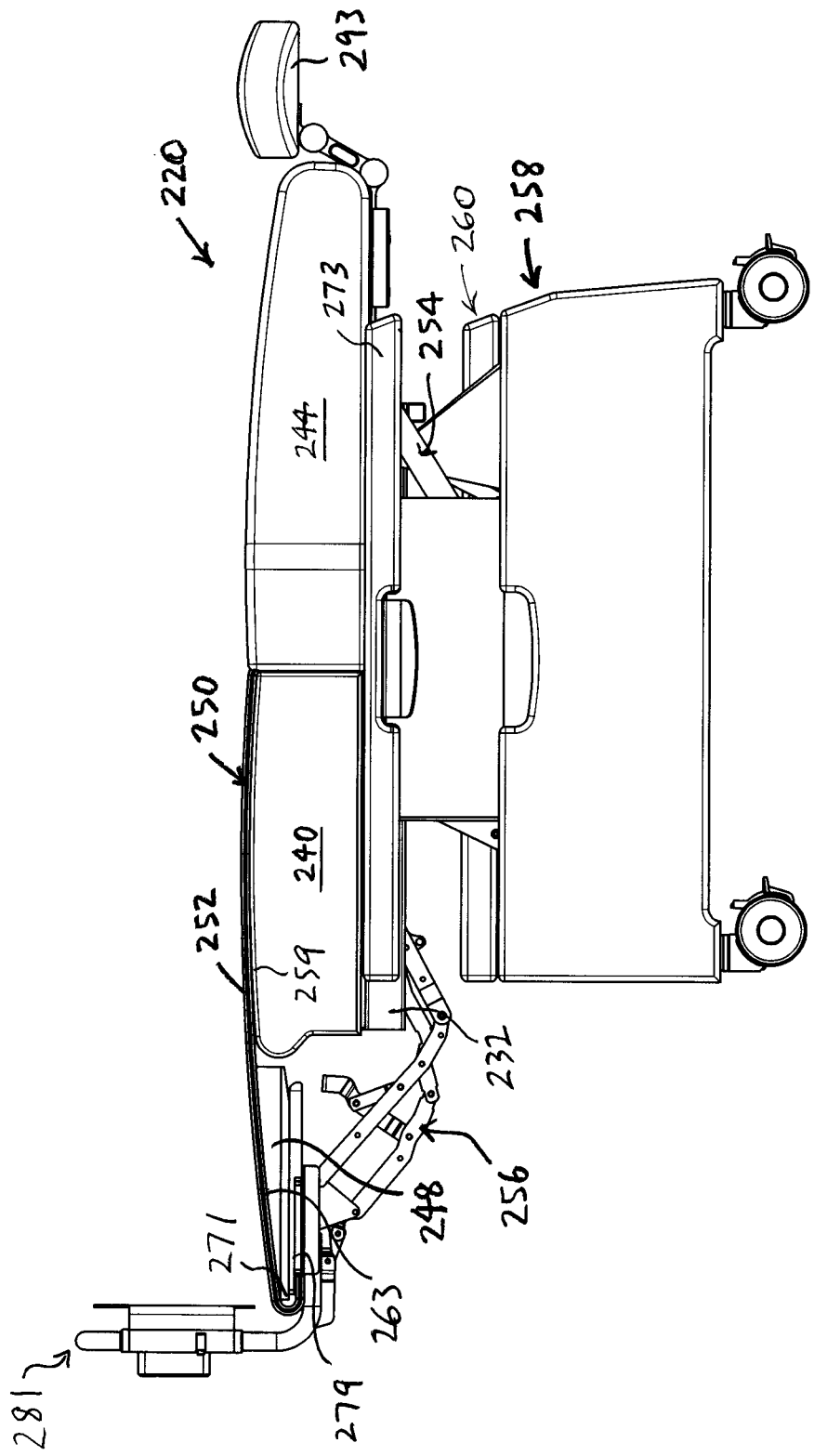
FIG. 21D is a left side view of the patient examination system of FIG. 21C in which the frame is extended and the backrest subassembly is in the horizontal position.

The patient support assembly 236 preferably includes a seat subassembly 238 including a seat cushion 240 with a top side 259 thereof, a back subassembly 242 including a back cushion 244, and a footrest subassembly 246 including a footrest cushion 248 with an external side 263 thereof. An upper element 232 of the frame assembly 222 supports the seat subassembly 238. As can be seen in FIG. 21D, the frame assembly 222 preferably includes a back linkage subassembly 254 for supporting the back subassembly 242, and a footrest linkage subassembly 256 for supporting the footrest subassembly 246. The patient support assembly 236 preferably also includes a foot support subassembly 281 (FIG. 19A).

It is also preferred that the patient examination system 220 includes a cover element 250, for covering the top side 259 of the seat cushion 240 and also for covering the external side 263 of the footrest cushion 248.

The frame assembly 222 preferably includes a lower element 224 and a number of intermediate elements 230 connecting the lower element 224 and the upper element 232. The patient examination system 220 preferably also includes a motor or similar means (not shown), for moving the upper element 232 and/or the back linkage subassembly 254. Preferably, the motor is controlled by a suitable controller "2Q".

The intermediate elements 230 preferably are configured to provide parallel linkages or such other arrangements as are suitable to position the upper element 232 as desired relative to the lower element 224, using the motor. The footrest linkage subassembly 256 preferably is mounted to the upper element 232 (FIG. 21D), so that vertical movement of the upper element 232, which supports the seat subassembly 238, causes corresponding movement of the footrest subassembly 246.

Accordingly, the motor is suitably connected with the back linkage subassembly 254 and the upper element 232 that are respectively connected with the back subassembly 242 and the seat subassembly 238, for controlling movement thereof, to locate the back subassembly 242, the seat subassembly 238, and the footrest subassembly 246 in selected positions relative to each other, as described above. Such positions include the Trendelenburg positions (not shown in FIGS. 19A-27B). Because those skilled in the art would be aware of suitable linkage assemblies and motors for movement of the portions of the patient examination system 220, further description thereof is unnecessary.

Preferably, the patient examination system 220 also includes left and right arm assemblies 258, 260, as will be described.

Figure 19C:
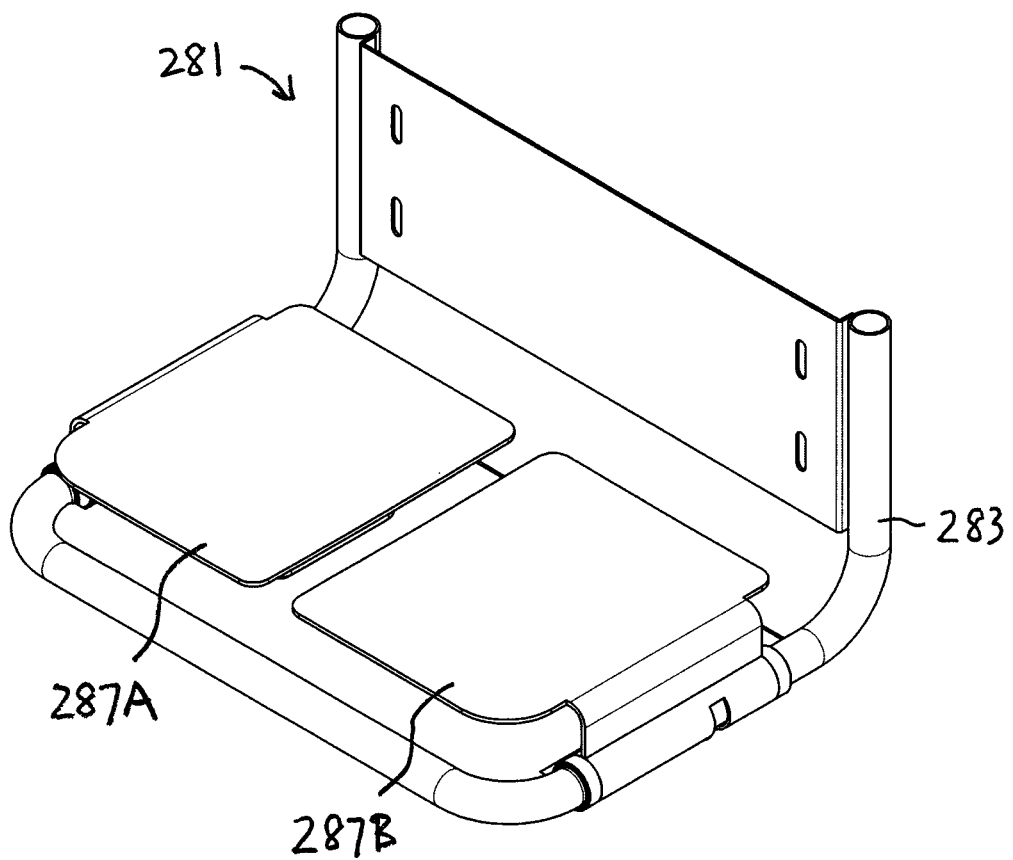
FIG. 19C is an isometric view of the foot support assembly with support plates in lowered positions thereof, drawn at a larger scale.
Figure 20A:
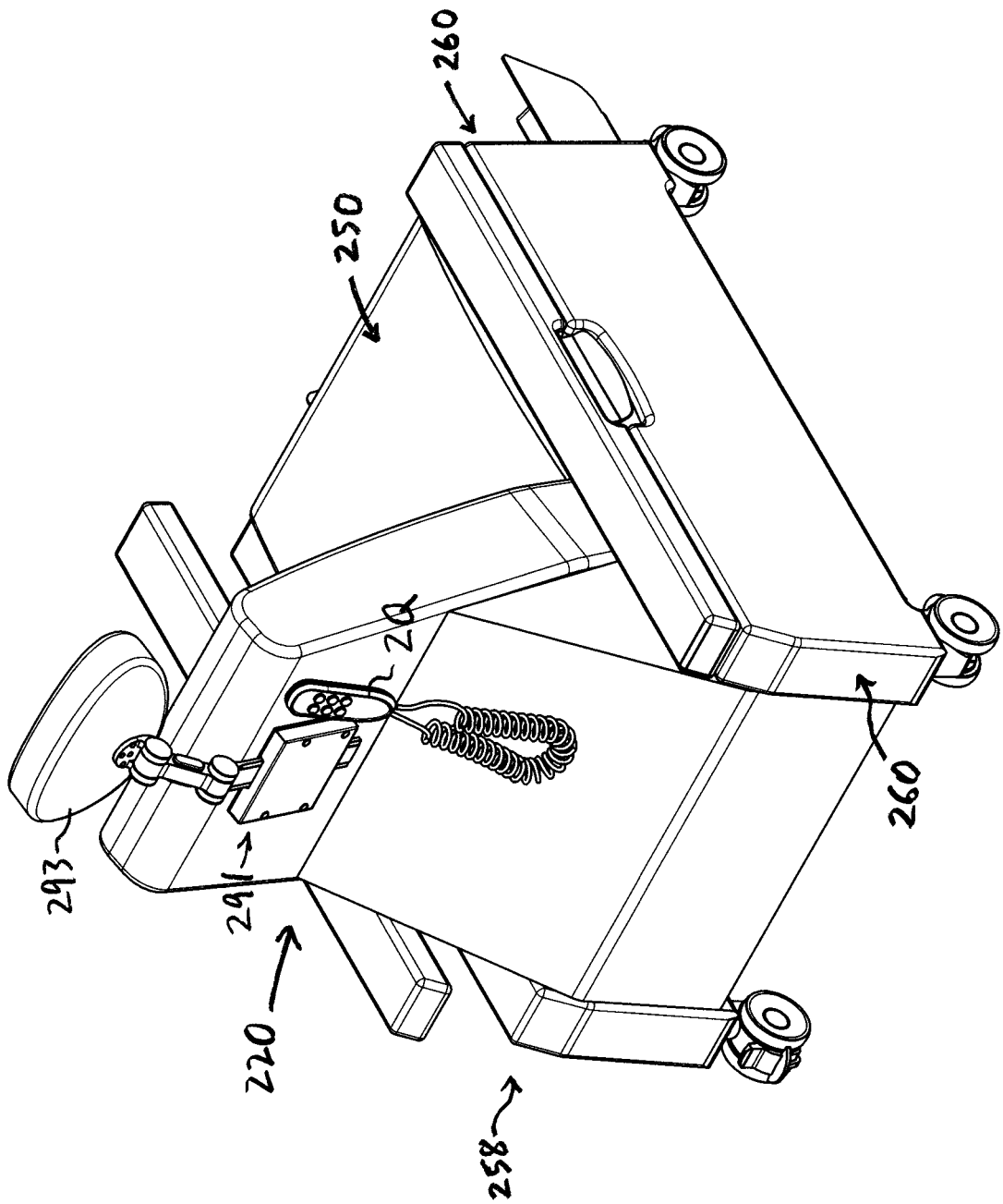
FIG. 20A is an isometric view of the patient examination system of FIGS. 19A and 19B, drawn at a smaller scale.
Figure 20B:
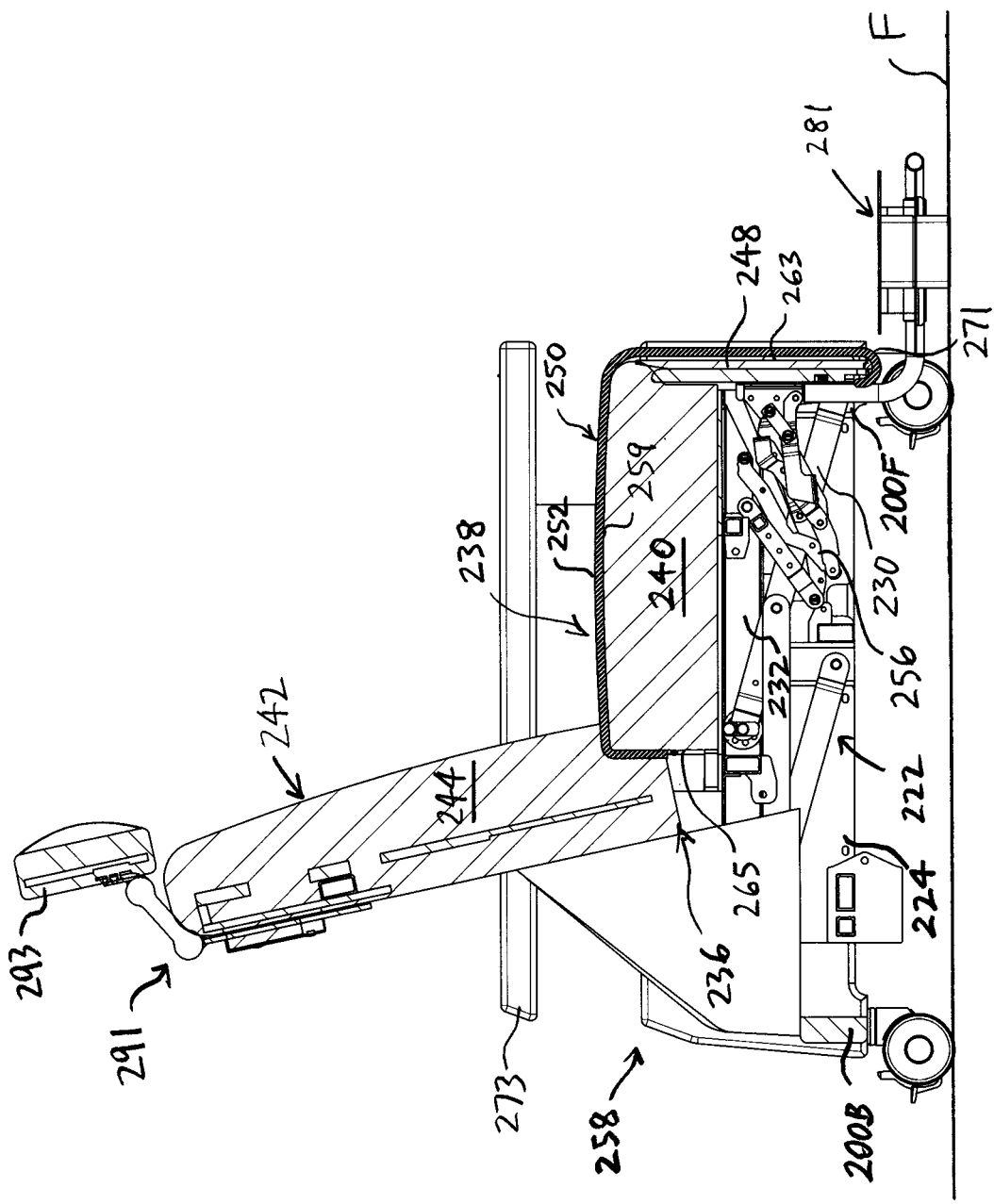
FIG. 20B is a cross-section of the patient examination system of FIGS. 19A, 19B, and 20A.

It is also preferred that the foot support subassembly 281 includes a support frame 283 (FIG. 19C), which is secured to the frame assembly 222 at the front end 200F thereof (FIG. 20B). As can be seen in FIG. 19C, the foot support subassembly 281 preferably includes step elements 287A, 287B, mounted to the support frame 283. Preferably, the step elements 287A, 287B are positionable in the foot support subassembly 281 to partially support the patient.

It is preferred that the step elements 287A, 287B are movable between closed positions (FIG. 19C) and open positions (FIG. 19A) thereof. It will be understood that, when the patient is sitting in the patient examination system 220, the patient may choose to rest the patient's feet on one or both of the step elements 287A, 287B, in their closed positions. Alternatively, and as can be seen in FIG. 19A, when the patient is sitting in the patient examination system 220 and the seat subassembly 238 is in its lowered position, the patient may prefer to have the step elements 287A, 287B in the open positions thereof, to enable the patient to put the patient's feet directly on the floor.

Figure 20D:
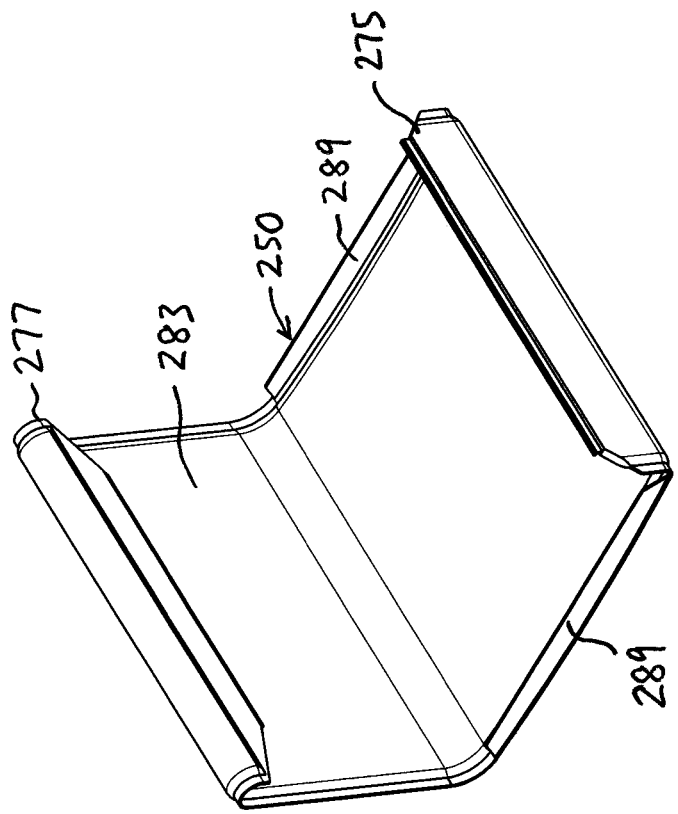
FIG. 20D is an isometric view of the cover element of FIG. 20C showing an interior surface thereof.
Figure 20C:
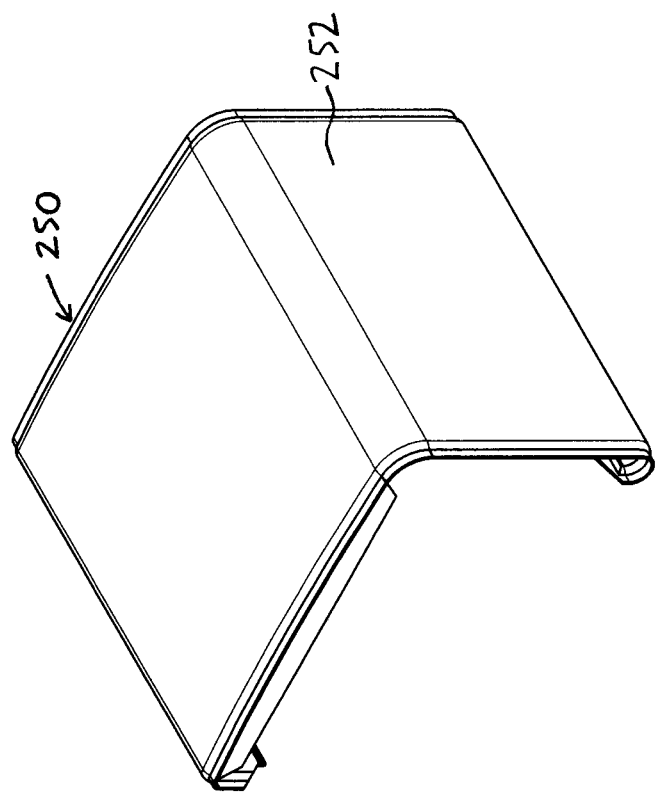
FIG. 20C is an isometric view of an embodiment of a cover element of the invention, showing an exterior surface thereof, drawn at a larger scale.

As can be seen in FIG. 20C, the cover element 250 preferably has an exterior surface 252 that faces away from the top side 259 and the external side 263, when the cover element 250 is positioned on the seat cushion 240 and the footrest cushion 248. The cover element 250 also has an interior surface 283 that engages the top side 259 and the external side 263, when the cover element 250 is positioned on the seat cushion 240 and on the footrest subassembly 246 (FIG. 20D).

Figure 20F:
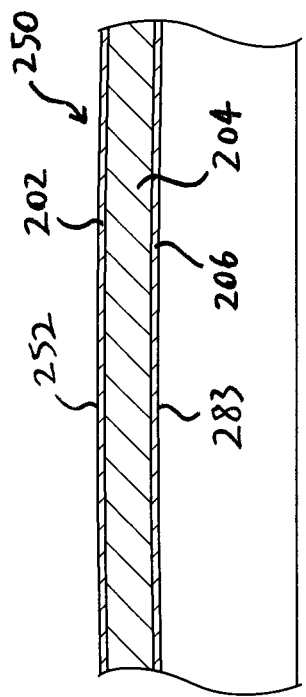
FIG. 20F is a cross-section of a portion of the cover element of FIGS. 20C-20E, drawn at a larger scale.
Figure 20E:
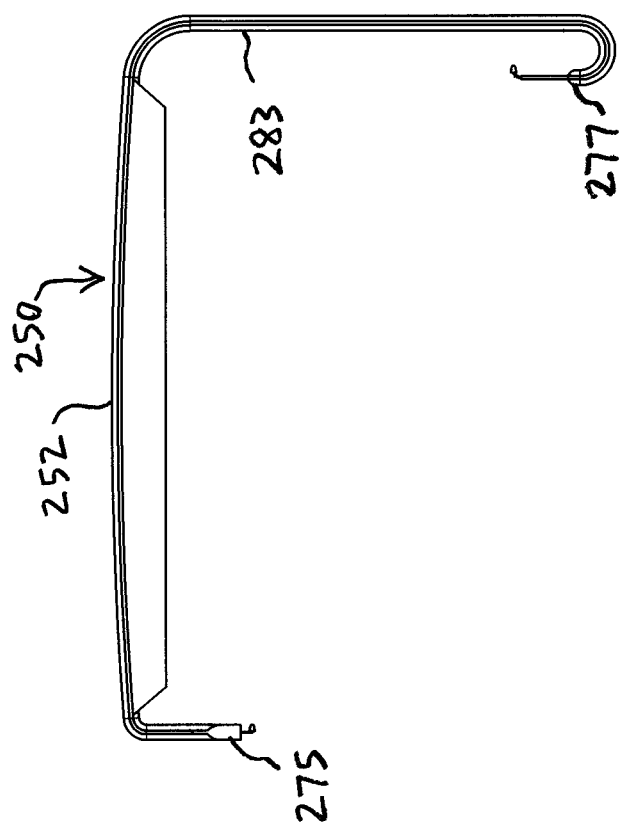
FIG. 20E is a side view of the cover element of FIGS. 20C and 20D.

As can be seen in FIGS. 20C-20E, the cover element 250 preferably extends between first and second ends 275, 277 thereof. It is preferred that, when the cover element 250 is positioned on the seat cushion 240 and the footrest cushion 246 the top side 259 thereof and the external side 263 thereof, the first end 275 is attached to an inner end 265 of the seat cushion 240, and the second end 277 is attached to an outer end 271 of the footrest cushion 248 (FIG. 20B). In one embodiment, the cover element 250 preferably covers the outer end 271, as well as the top side 259 and the external side 263 (FIG. 21D).

Those skilled in the art would be aware of suitable devices for fastening the first end 275 of the cover element 250 to the inner end 265 of the seat cushion 240, and for fastening the second end 277 to the outer end 271 of the footrest cushion 248. Alternatively, the second end 277 may be secured to an internal side 279 of the footrest cushion 248 (FIG. 21D). The cover element 250 may include two side flaps 289 (FIG. 20D) which may be respectively pushed between the arm assemblies 258, 260 and the seat cushion 240, along sides of the seat cushion 240, to help keep the cover element 250 in position covering the top side 259 and the external side 263. The cover element 250 covers the entire top side 259 of the seat cushion 240, between the armrest assemblies 258, 260.

It will be understood that the cover element 250 preferably is removable from the seat cushion 240 and the footrest cushion 248, e.g., for cleaning thereof, or repair thereof.

The cover element 250 may be made of any suitable material, or materials. In one embodiment, for example, as illustrated in FIG. 20F, the cover element 250 preferably includes outer, middle, and inner layers 202, 204, 206. The layers 202, 204, 206 preferably include any suitable material or materials, attached to each other in any suitable manner. For example, in one embodiment, the outer layer 202 preferably is a vinyl material, the middle layer 204 preferably is a foam material, and the inner layer 206 preferably is a suitable backing material. It is also preferred that the outer layer 202 has a relatively high coefficient of friction, to minimize the possibility that the patient may slide when located on the cover element 250.

It will be understood that a portion "XS" of the back cushion 244 (FIG. 19B) tends to be compressed against the inner end 265 of the seat cushion 240, when the back subassembly 242 is in its upright position. It will also be understood that, in FIG. 20B, the portion "XS" of the back cushion 244 is omitted, for clarity of illustration. Those skilled in the art would appreciate that, as a practical matter, when the back subassembly is in the upright position thereof, the portion "XS" is compressed due to its engagement with the inner end 265 of the seat cushion 240, and the part of the seat cushion 240 near the inner end 265 may also be compressed due to its engagement with the back cushion 244.

Figure 22A:
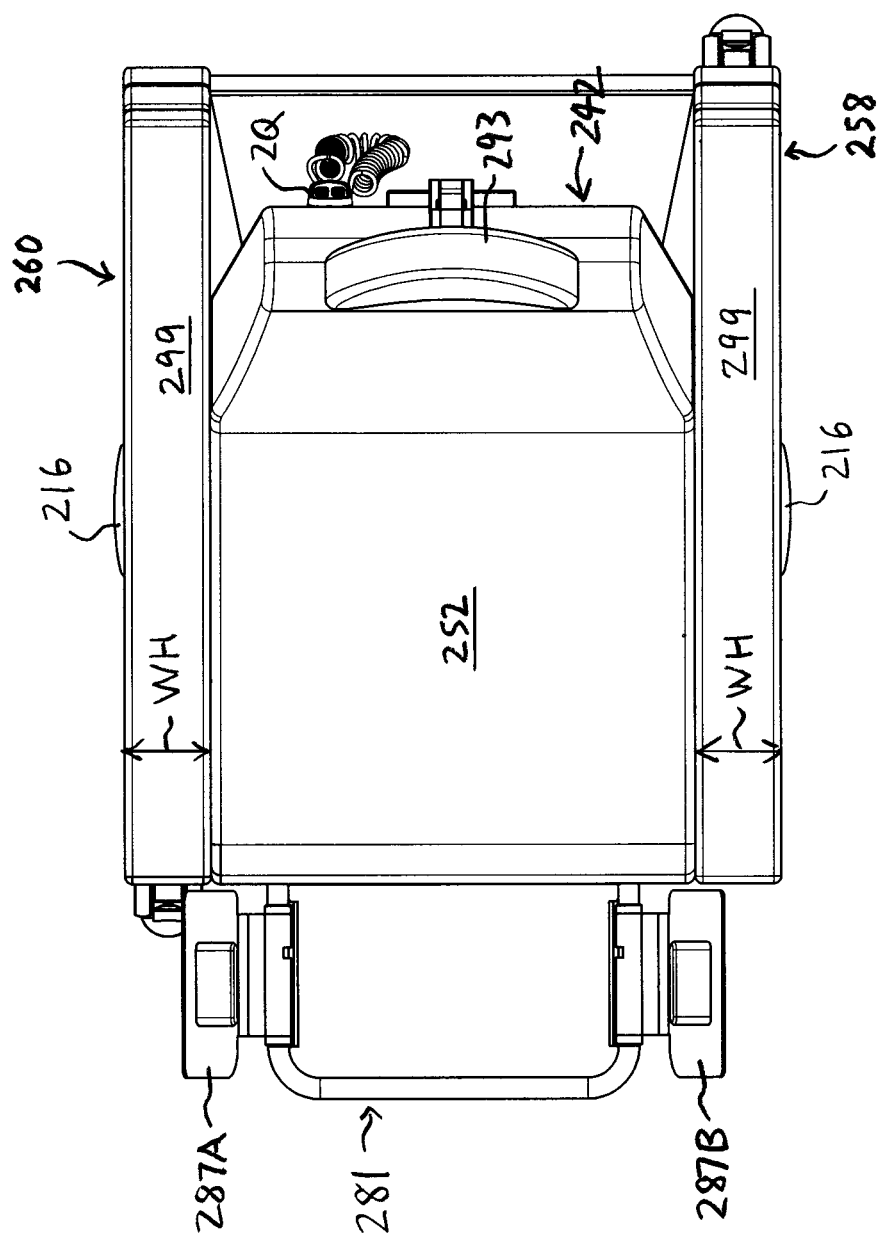
FIG. 22A is a top view of the patient examination system of FIGS. 21A and 21B.
Figure 22B:
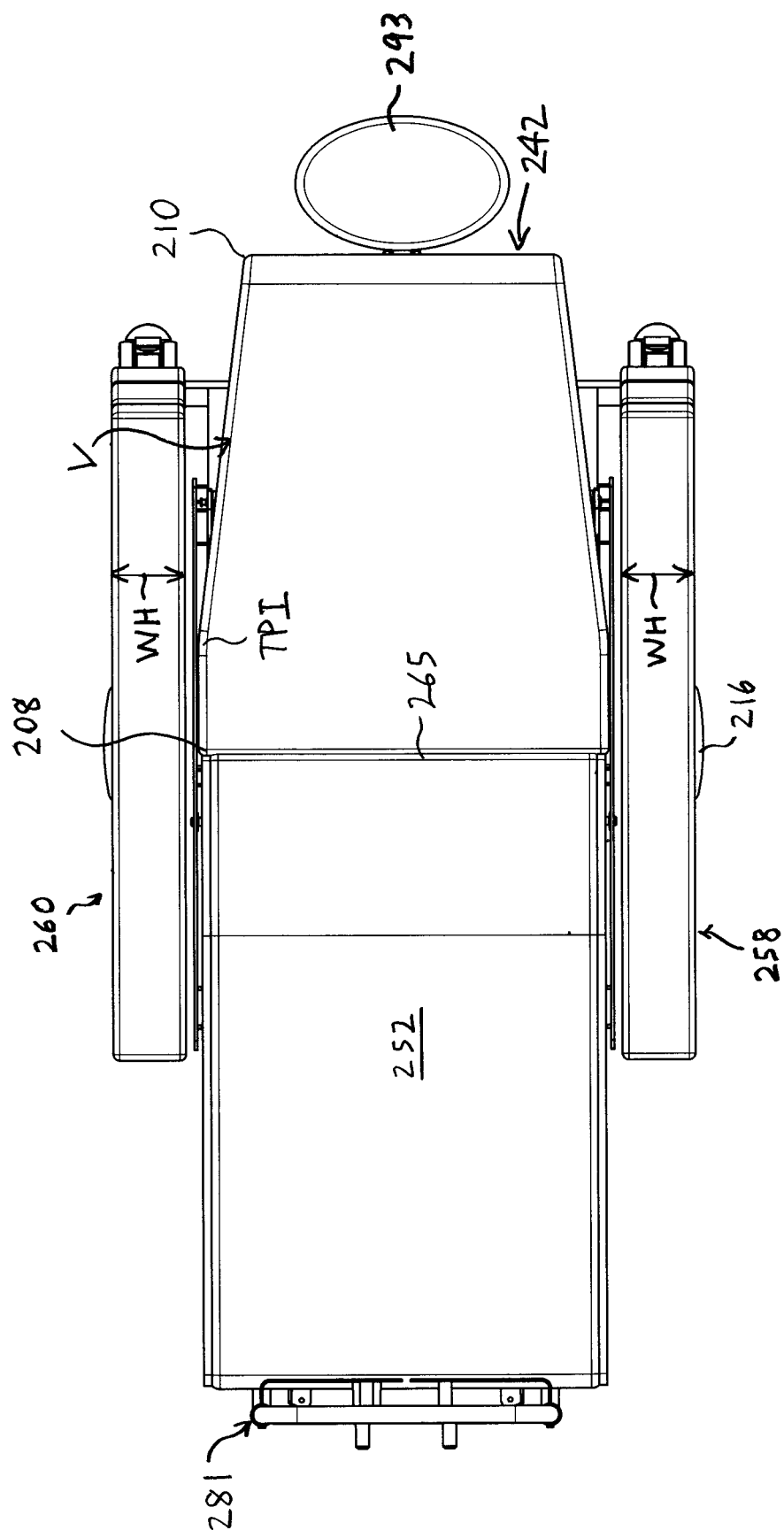
FIG. 22B is a top view of the patient examination system of FIG. 22A in which the backrest subassembly is in the horizontal position.
Figure 23A:
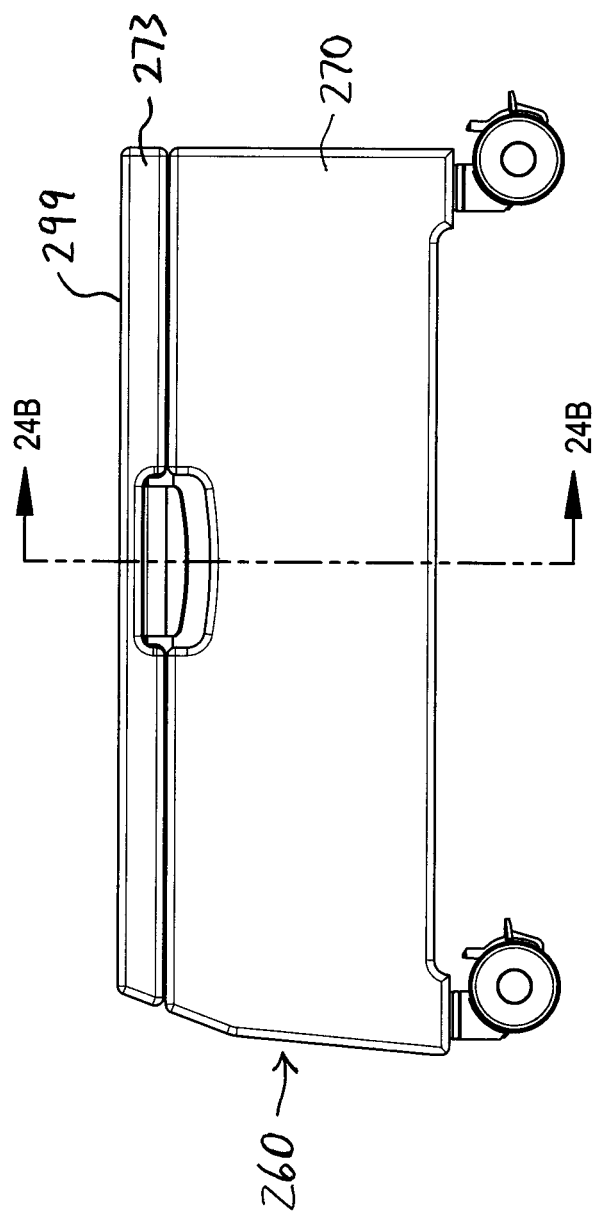
FIG. 23A is a side view of an embodiment of the right side armrest assembly of the patient examination system of FIGS. 22A and 22B, in which an armrest element thereof is in an engaged position.
Figure 23B:
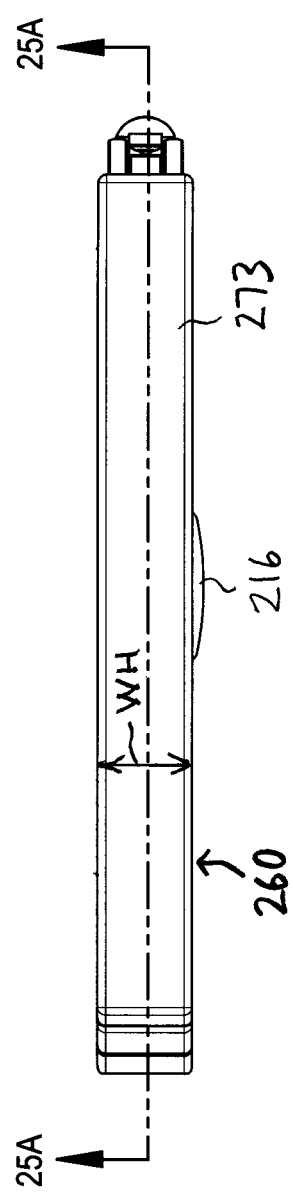
FIG. 23B is a top view of the armrest assembly of FIG. 23A.
Figure 23C:
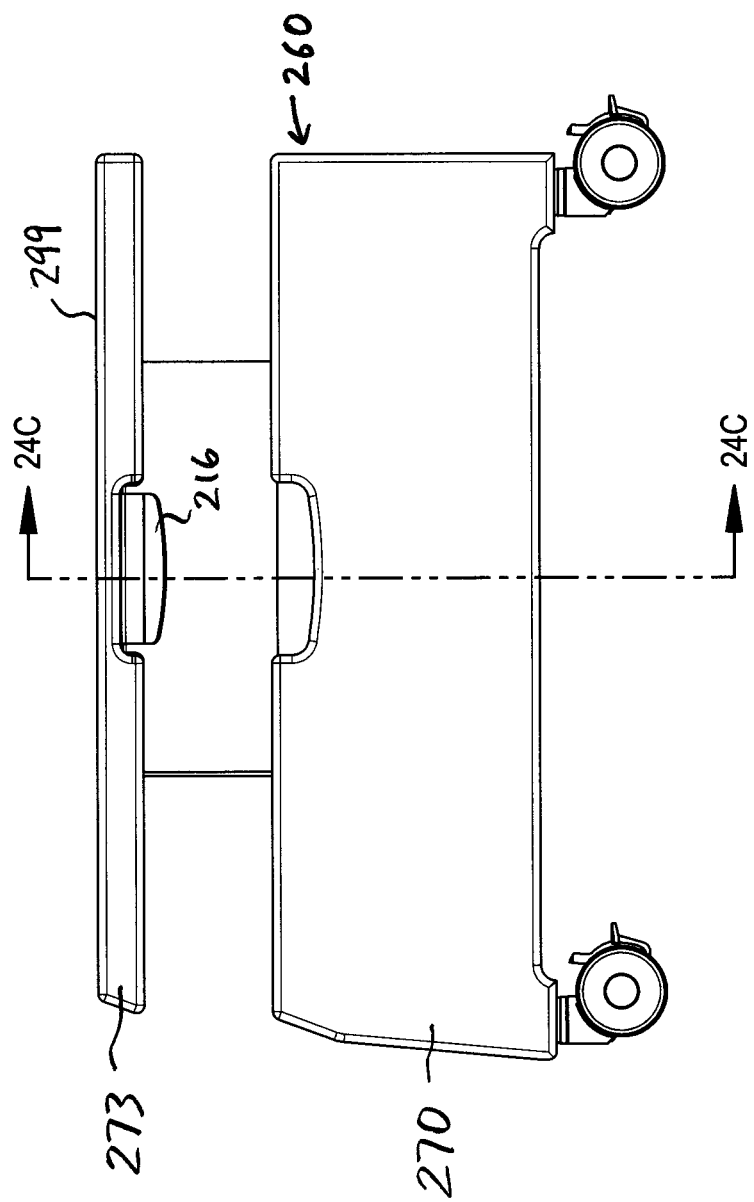
FIG. 23C is a side view of the armrest assembly of FIG. 23A in which the armrest is in an elevated position.

As can be seen in FIG. 22B, it is preferred that the back subassembly 242 extends between inner and outer ends 208, 210. The inner end 208 is located proximal to the inner end 265 of the seat cushion 240, and the outer end 210 is located distal to the inner end 265. Preferably, the back subassembly 242 is wider at the inner end 208 thereof than at the outer end 210 thereof.

In one embodiment, the back subassembly 242 preferably includes a tapered portion "V" thereof, extending between a tapered portion interior end "TPI" and the outer end 210 of the back subassembly 242 (FIG. 22B). Preferably, the tapered portion "V" is gradually tapered from the tapered portion interior end "TPI" to the outer end 210 of the back subassembly 242. Due to the tapered portion "V", the outer end 210 is narrower than the inner end 208. As can be seen in FIG. 22B, the advantage of the tapered back subassembly 242 is that the tapering in the region proximate to the outer end 210 permits health care providers (not shown) to be positioned in proximity to the patient's head and upper body. Those skilled in the art would appreciate that the tapered portion "V" is particularly helpful in this regard when the back subassembly 242 is positioned horizontal, or approximately horizontal, as shown in FIG. 22B.

It will be understood that the arm assemblies 258, 260 are attached to the frame assembly 222. The left and right arm assemblies 258, 260 preferably are positioned on opposite sides of the seat subassembly 238. Preferably, each of the arm assemblies 258, 260 is attached to the lower element 224 of the frame assembly 222 (FIG. 20B).

The arm assemblies 258, 260 are also configured to enable health care providers to be positioned proximate to the patient. Each of the arm assemblies 258, 260 preferably includes an armrest body 270 and an armrest element 273 that is movable relative to the armrest body 270 between an engaged position thereof (FIG. 23A) and an elevated position thereof (FIG. 23C), in which the armrest element 273 is located at a preselected height above the armrest body 270. As will be described, the armrest element 273 is also positionable in intermediate positions between the lowered and raised positions.

As will be described, the armrest assembly 260 is illustrated in detail in FIGS. 23A-26. It will be understood that the armrest assemblies 258, 260 preferably are the mirror images of each other. Accordingly, only the armrest assembly 260 is described in detail. In FIGS. 19A, 20A, and 21A-21C, the armrest element 273 of the right armrest assembly 260 is shown in the engaged position thereof, and the armrest element 273 of the left armrest assembly 258 is shown in the elevated position thereof, solely for clarity of illustration. It will be understood that the armrest elements 273 are positioned independently of each other.

Figure 24A:
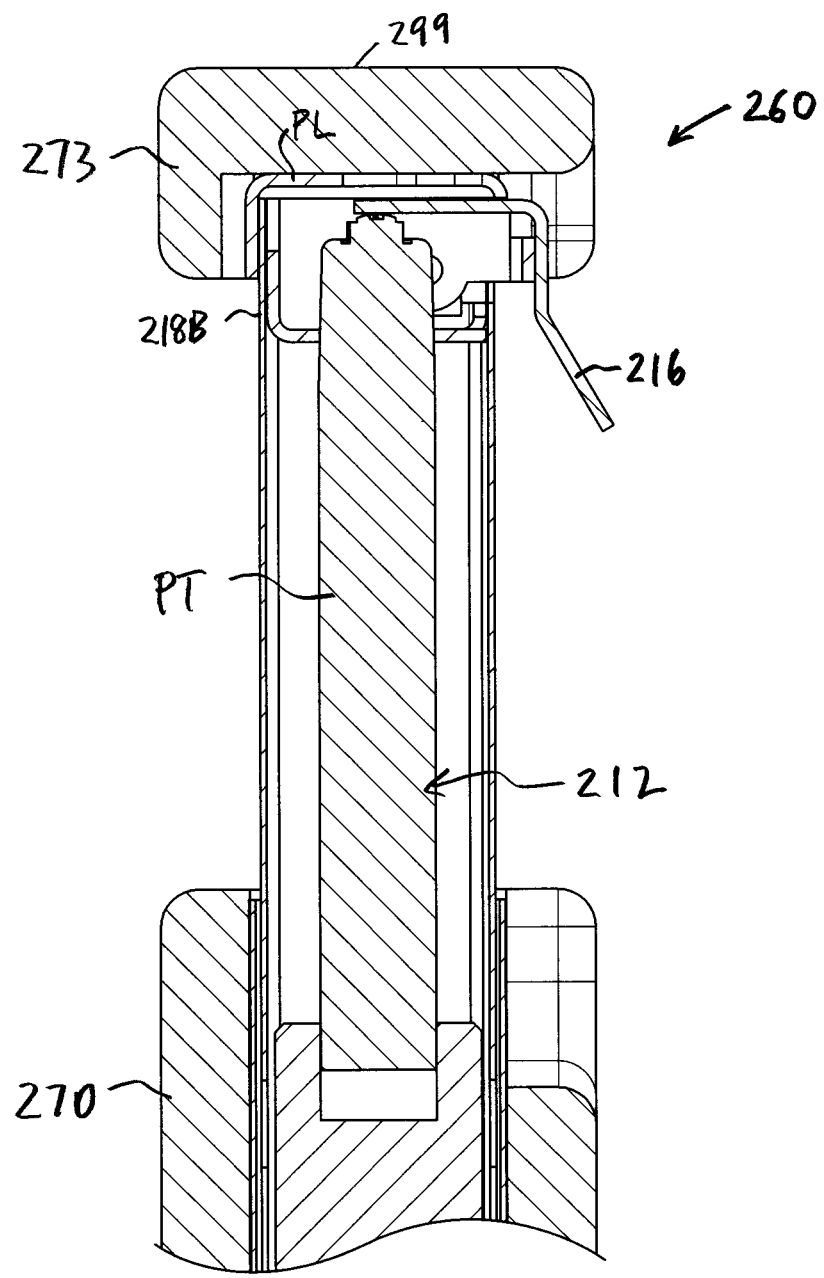
FIG. 24A is a cross-section of the armrest assembly of FIG. 23C in which an activation lever is in a neutral position thereof, drawn at a larger scale.
Figure 25A:
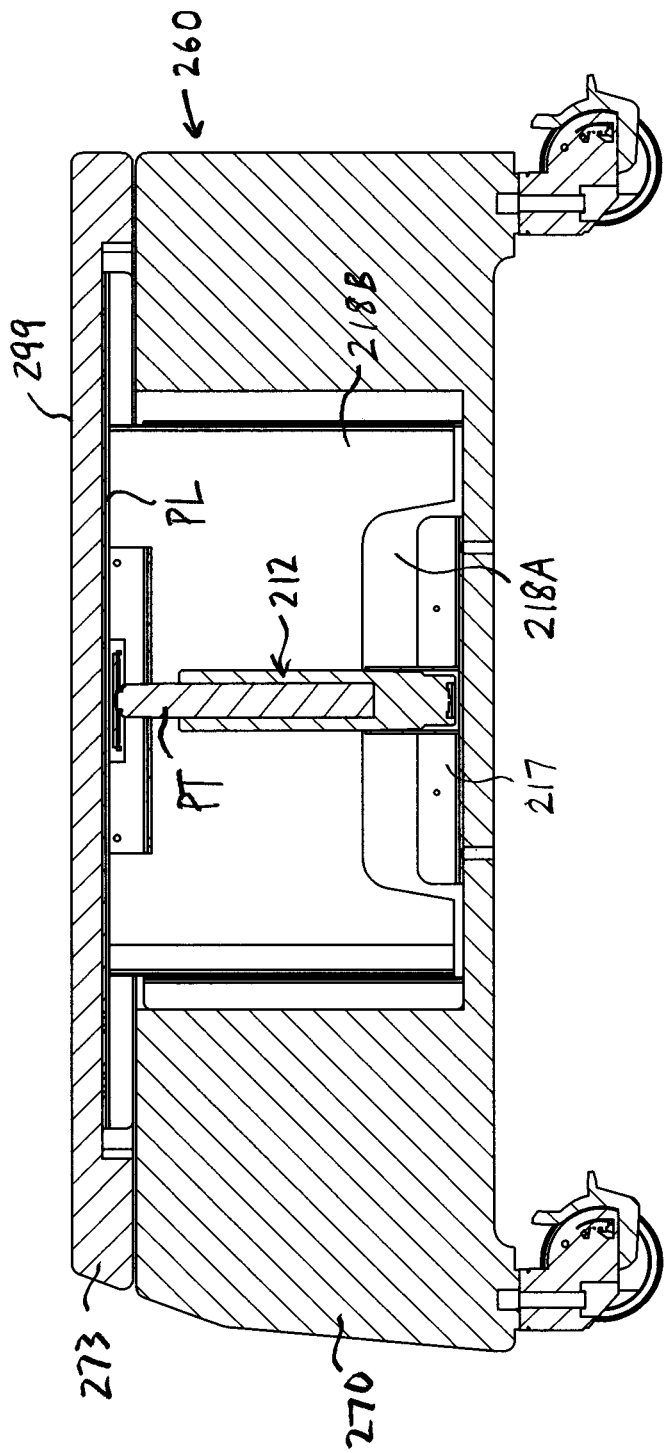
FIG. 25A is a longitudinal cross-section of the armrest assembly of FIG. 23A in which the armrest element is in the engaged position thereof, drawn at a smaller scale.
Figure 25B:
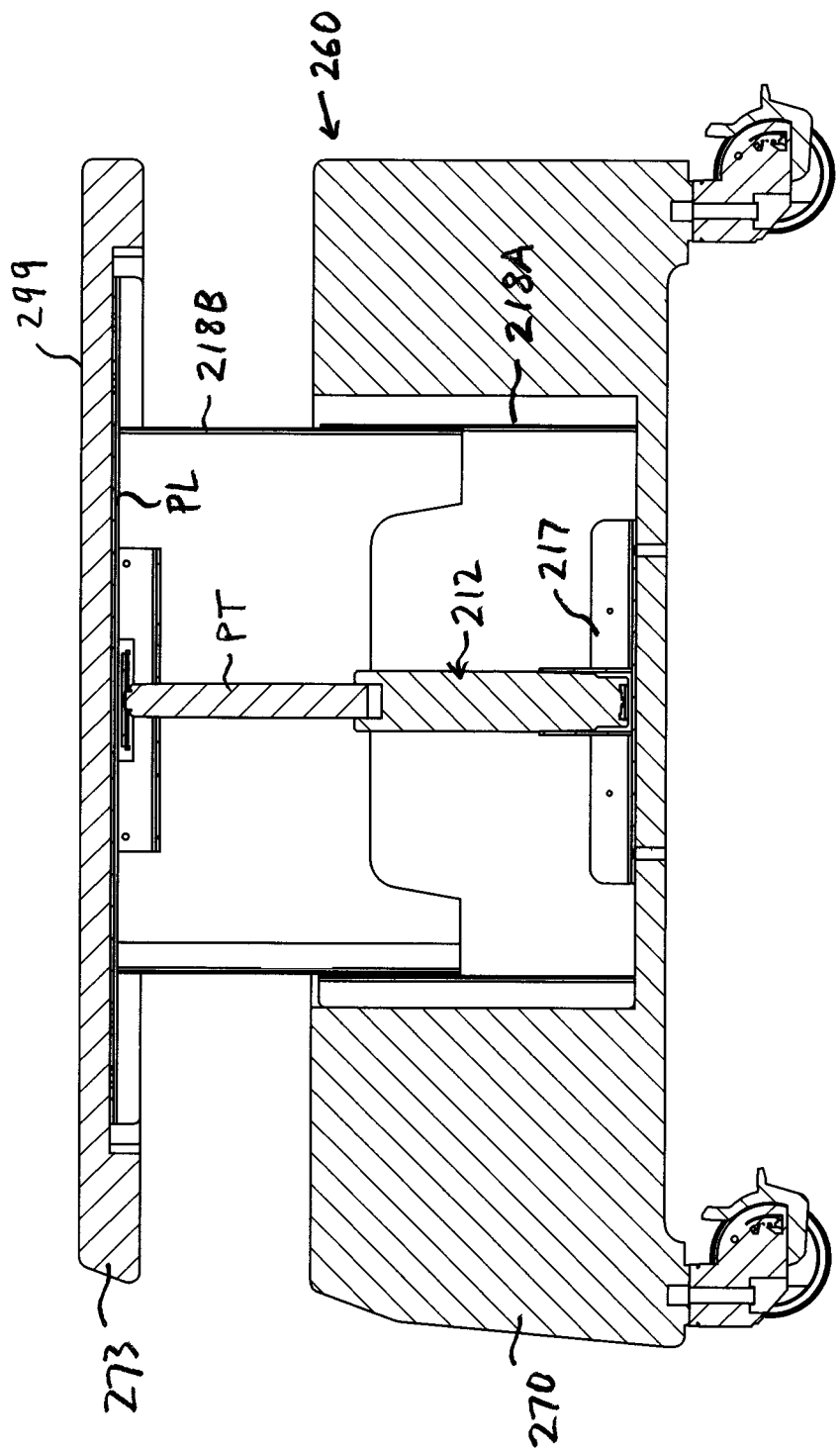
FIG. 25B is a longitudinal cross-section of the armrest assembly of FIG. 23C in which the armrest element is in the elevated position thereof.

As can be seen in FIGS. 24A-24C, the arm assembly 260 preferably includes a height adjustment device 212 (FIGS. 24A-26) that is controllable to move the armrest element 273 relative to the armrest body 270. Preferably, the armrest element 273 is vertically movable between the engaged position thereof and the elevated position thereof by the height adjustment device 212, which connects the armrest element 273 and the armrest body 270.

Those skilled in the art would be aware of suitable height adjustment devices. In one embodiment, the height adjustment device 212 preferably is a pneumatic gas lift cylinder, as shown in FIGS. 24A-24C. In the height adjustment device 212 as illustrated, the device 212 preferably includes an activation lever 216 that may be used to activate the device, e.g., to cause the device to lift the armrest element 273 to its raised position, or to an intermediate position between the raised and lowered positions, or which may be used to lower the armrest element 273, if a force is exerted downwardly on the armrest element 273 when the device 212 is activated. The activation lever 216 is shown in the neutral position thereof in FIG. 24A, and the activation lever 216 is shown in its activating position (in which vertical movement of the armrest element 273 may occur) in FIGS. 24B and 24C. Because pneumatic gas lift cylinders are known, further description thereof is unnecessary.

As can be seen in FIGS. 23A-26, the height adjustment device 212 preferably is mounted in the armrest body 270.

Figure 26:
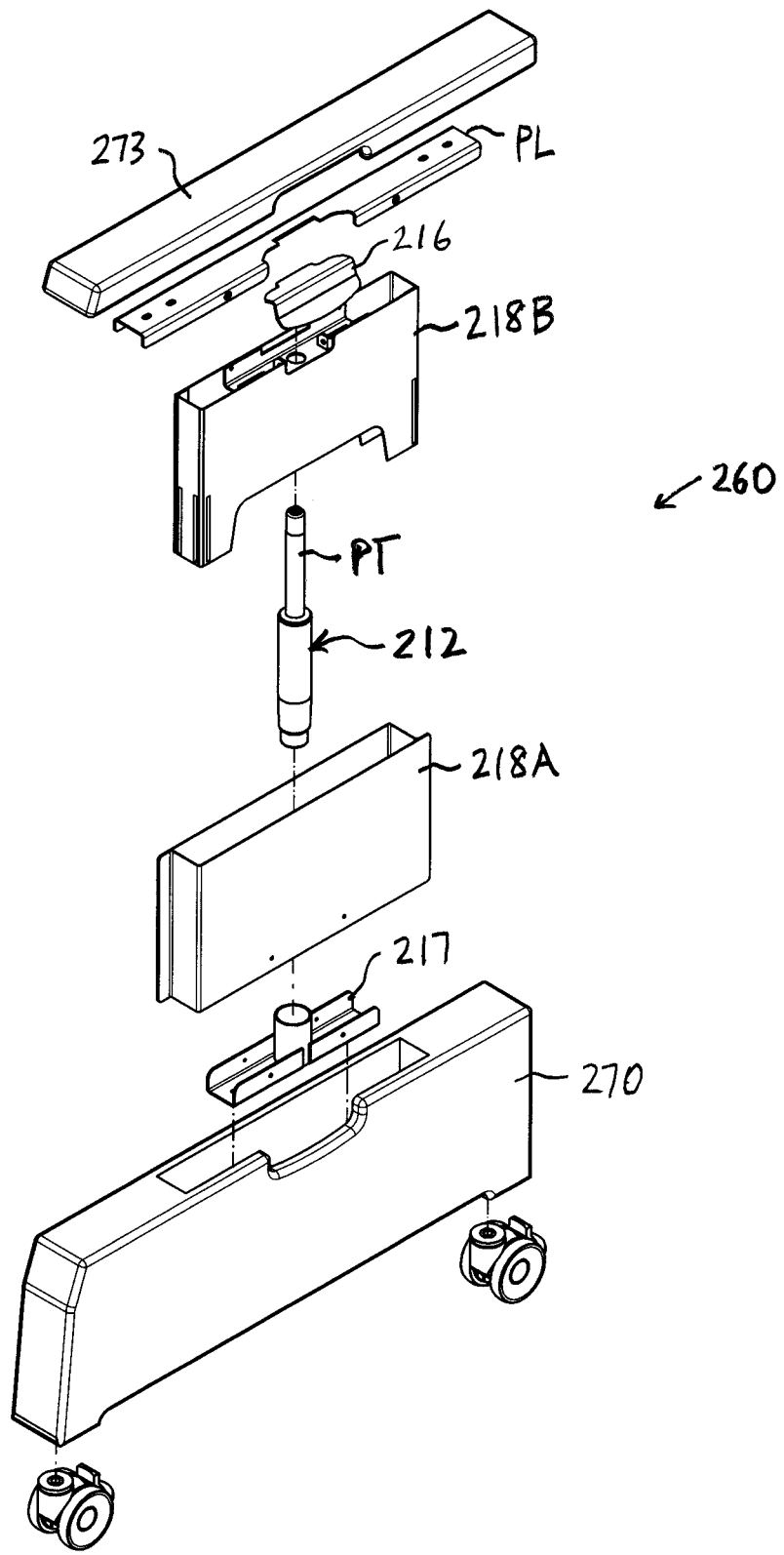
FIG. 26 is an exploded isometric view of the armrest assembly of FIGS. 23A-25B, drawn at a smaller scale.

Preferably, the height adjustment device 212 is mounted in a bracket 217 (FIG. 26) that is secured in the body 270, and sleeves 218A, 218B guide a movable part "PT" of the height adjustment device 212 in its vertical travel relative to the body 270. It is also preferred that the armrest element 273 includes a plate "PL", to which an upper end of the sleeve 218B may be secured (FIG. 26).

From the foregoing, it can be seen that the armrest assemblies 258, 260 have the advantage that, regardless of whether the armrest element 273 is in the engaged position or the elevated position or in one of the intermediate positions therebetween, the overall horizontal width "WH" of each of the armrest assemblies 258, 260 is the same. (It will be understood that the overall horizontal width "WH" does not include the activation lever 216, which extends a small distance horizontally beyond the body 270 (FIG. 23B).) Those skilled in the art would appreciate that, because the overall horizontal width "WH" is the same regardless of the position of the armrest element 273 relative to the armrest body 270, health care providers can stand relatively close to the patient.

Preferably, when the seat subassembly 238 is in the lowered position thereof and the armrest element 273 is in the engaged position thereof, an upper surface 299 of the armrest element 273 is at least partially horizontally aligned with a portion "SP" of the exterior surface 252 of the cover element 250 (FIG. 21B) that is located above the top side 259 of the seat cushion 240. It will be understood that this enables the patient to be moved laterally (while in a sitting position) onto or from the patent examination system 20 from or onto another supporting device (not shown), e.g., a wheelchair.

The patient examination system 220 preferably also includes a headrest subassembly 291 mounted to the back subassembly 242, for locating a head rest 293 thereof generally proximal to the outer end 210 of the back subassembly 242. As can be seen in FIGS. 27A and 27B, the headrest assembly 291 preferably includes a bracket "N" mounted to the back subassembly 242 and a support post subassembly 295 that is mounted in a bracket "N". The head rest 293 preferably is mounted to a distal end "DE" of the support post subassembly 295. Preferably, the support post subassembly 295 is movable relative to the bracket "N" between a first position thereof (FIG. 27A), in which the head rest is located adjacent to the outer end 210, and a second position thereof (FIG. 27B), in which the head rest is spaced apart from the outer end of the back subassembly 242 by a predetermined distance "DX" (FIG. 27B).

The bracket "N" is configured to permit the support post subassembly 295 to be located as required, for positioning the head rest 293 in a selected position relative to the outer end 210 of the back rest subassembly 242.

In one embodiment, the support post subassembly 295 preferably includes an intermediate bar 297 and first and second pivot pins "2HRP$_1$", "2HRP$_2$", spaced apart from each other by the intermediate bar 297. It will be understood that the intermediate bar 297 is pivotable about the first pivot pin "2HRP$_1$" and the head rest 293 is pivotable about the second pivot pin "2HRP$_2$", to permit adjustment of the position of the head rest 293 relative to the outer end 210 of the back subassembly 242 as required for the patient's comfort. The support post subassembly 295 also includes a post 295A, one end of which is mounted in the bracket "N". The first pivot pin "2HRP$_1$" is mounted at the other end of the post 295A.

It will be appreciated by those skilled in the art that the invention can take many forms, and that such forms are within the scope of the invention as claimed. The scope of the claims should not be limited by the preferred embodiments set forth in the examples, but should be given the broadest interpretation consistent with the description as a whole.

We claim:

1. A patient examination system for locating a patient above a floor supporting the patient examination system, the patient examination system comprising:
   a frame assembly comprising at least one lower element at least partially defining a lower side of the frame assembly located proximal to the floor;
   at least one motion-controlling assembly connected to the frame assembly for moving at least one selected movable portion of the frame assembly relative to the floor;
   said at least one selected movable portion comprising an upper element defining an upper side of the frame assembly located distal to the floor, the upper element being movable by said at least one motion-controlling assembly relative to the lower element;
   a patient support assembly comprising:
      a back subassembly comprising a back cushion;
      a footrest subassembly comprising a footrest cushion with an external side thereof;
      a seat subassembly comprising a seat cushion with a top side thereof, the seat cushion extending between an inner end thereof located adjacent to the back cushion, the inner end being transverse to the top side, and an outer end located proximal to the footrest cushion;
      the footrest cushion extending between an inner end thereof located proximal to the outer end of the seat cushion and an outer end thereof located distal to the outer end of the seat cushion;
      a cover element covering the top side of the seat cushion and the external side of the footrest cushion, the cover element having an exterior surface facing away from the top side and the external side;
      the seat subassembly being secured to the upper element of the frame assembly to locate the top side of the seat cushion distal to the upper element, the frame assembly being configured to move the seat subassembly between a lowered position thereof and a raised position thereof, to at least one intermediate seat position therebetween, and to locate the seat subassembly in at least one Trendelenburg position;
      the back subassembly being connected with the upper element by a back linkage subassembly, the back linkage subassembly being configured to move the back subassembly between an upright position thereof and a horizontal position thereof, to at least one intermediate back position therebetween, and to locate the back subassembly in at least one Trendelenburg position;
      the footrest subassembly being connected to the upper element of the frame assembly by a footrest linkage subassembly, the footrest linkage subassembly supporting the footrest cushion to locate the external side distal to the footrest linkage subassembly, the footrest linkage subassembly being configured to move the footrest subassembly between a retracted position thereof in which the footrest cushion is positioned orthogonally to the floor to partially define a first gap between the seat cushion and the footrest cushion, and an extended position thereof, in which the external side of the footrest cushion is aligned with the top side of the seat cushion to partially define a second gap between the seat cushion and the footrest cushion;

the cover element extending between a first end thereof attached to the inner end of the seat cushion at a location thereon spaced apart from the top side and a second end thereof attached to the outer end of the footrest cushion, the cover element extending continuously over the top side of the seat cushion and the external side of the footrest cushion to bridge the first gap when the footrest subassembly is in the retracted position, and to bridge the second gap when the footrest subassembly is in the extended position thereof, the cover element being sized to cover the top side of the seat cushion and the external side of the footrest cushion;

a foot support subassembly, located at a front end of the frame assembly; and the foot support subassembly comprising a support frame secured to the frame assembly and a pair of step elements mounted to the support frame, the step elements being movable between respective closed positions thereof, in which the patient is partially supportable by the step elements, and open positions thereof, in which the patient, is not supportable by the step elements.

2. A patient examination system for locating a patient above a floor supporting the patient examination system, the patient examination system comprising:

a frame assembly comprising at least one lower element at least partially defining a lower side of the frame assembly located proximal to the floor;

at least one motion-controlling assembly connected to the frame assembly for moving at least one selected movable portion of the frame assembly relative to the floor;

said at least one selected movable portion comprising an upper element defining an upper side of the frame assembly located distal to the floor, the upper element being movable by said at least one motion-controlling assembly relative to the lower element;

a patient support assembly comprising:

a back subassembly comprising a back cushion;

a footrest subassembly comprising a footrest cushion with an external side thereof;

a seat subassembly comprising a seat cushion with a top side thereof, the seat cushion extending between an inner end thereof located adjacent to the back cushion, the inner end being transverse to the top side, and an outer end located proximal to the footrest cushion;

the footrest cushion extending between an inner end thereof located proximal to the outer end of the seat cushion and an outer end thereof located distal to the outer end of the seat cushion;

a cover element covering the top side of the seat cushion and the external side of the footrest cushion, the cover element having an exterior surface facing away from the top side and the external side;

the seat subassembly being secured to the upper element of the frame assembly to locate the top side of the seat cushion distal to the upper element, the frame assembly being configured to move the seat subassembly between a lowered position thereof and a raised position thereof, to at least one intermediate seat position therebetween, and to locate the seat subassembly in at least one Trendelenburg position;

the back subassembly being connected with the upper element by a back linkage subassembly, the back linkage subassembly being configured to move the back subassembly between an upright position thereof and a horizontal position thereof, to at least one intermediate back position therebetween, and to locate the back subassembly in at least one Trendelenburg position;

the footrest subassembly being connected to the upper element of the frame assembly by a footrest linkage subassembly, the footrest linkage subassembly supporting the footrest cushion to locate the external side distal to the footrest linkage subassembly, the footrest linkage subassembly being configured to move the footrest subassembly between a retracted position thereof in which the footrest cushion is positioned orthogonally to the floor to partially define a first cap between the seat cushion and the footrest cushion, and an extended position thereof, in which the external side of the footrest cushion is aligned with the top side of the seat cushion to partially define a second gap between the seat cushion and the footrest cushion;

the cover element extending between a first end thereof attached to the inner end of the seat cushion at a location thereon spaced apart from the top side and a second end thereof attached to the outer end of the footrest cushion, the cover element extending continuously over the top side of the seat cushion and the external side of the footrest cushion to bridge the first gap when the footrest subassembly is in the retracted position, and to bridge the second gap when the footrest subassembly is in the extended position thereof, the cover element being sized to cover the top side of the seat cushion and the external side of the footrest cushion:

the cover element comprising:

an inner layer for engagement with the top side of the seat cushion and the external side of the footrest cushion;

an outer layer for engagement with the patient, the outer layer being formed for resisting sliding movement of the patient thereon; and a middle layer located between the inner and outer layers, the middle layer comprising a resilient material.

* * * * *